(12) United States Patent
Lavely et al.

(10) Patent No.: US 10,468,230 B2
(45) Date of Patent: Nov. 5, 2019

(54) NONDESTRUCTIVE SAMPLE IMAGING

(71) Applicant: BAE Systems Information and Electronic Systems Integration Inc., Nashua, NH (US)

(72) Inventors: Eugene M. Lavely, Concord, MA (US); Adam J. Marcinuk, Lyndeborough, NH (US); Amrita V. Masurkar, Burlington, MA (US); Paul R. Moffitt, Hollis, NH (US); Michael S. Richman, Carlisle, MA (US); Jonathan R. Takahashi, Pelham, NH (US); Jonathan K. Tong, Cambridge, MA (US); Chris L. Willis, Hollis, NH (US)

(73) Assignee: BAE Systems Information and Electronic Systems Integration Inc., Nashua, NH (US)

(*) Notice: Subject to any disclaimer, the term of this patent is extended or adjusted under 35 U.S.C. 154(b) by 0 days.

(21) Appl. No.: 15/949,166

(22) Filed: Apr. 10, 2018

(65) Prior Publication Data

US 2019/0311881 A1    Oct. 10, 2019

(51) Int. Cl.
 *H01H 37/28* (2006.01)
 *G01N 23/22* (2018.01)
 (Continued)

(52) U.S. Cl.
 CPC ............ *H01J 37/244* (2013.01); *H01J 37/20* (2013.01); *H01J 37/222* (2013.01);
 (Continued)

(58) Field of Classification Search
 CPC ..... H01J 2237/2445; H01J 2237/24415; H01J 2237/2442; H01J 2237/063;
 (Continued)

(56) References Cited

U.S. PATENT DOCUMENTS 4,169,228 A * 9/1979 Briska .................. G01N 23/223
378/45
6,031,611 A    2/2000 Rosakis et al.
(Continued)

FOREIGN PATENT DOCUMENTS

EP    2599103    3/2017

OTHER PUBLICATIONS

Nghia T. Vo, Michael Drakopoulos, Robert C. Atwood, and Christina Reinhard. Reliable method for calculating the center of rotation in parallel-beam tomography. Optics express, 22(16):19078-19086, 2014.
(Continued)

*Primary Examiner* — David A Vanore
(74) *Attorney, Agent, or Firm* — Finch & Maloney PLLC; Scott J. Asmus

(57) ABSTRACT

A system and method for imaging a sample having a complex structure (such as an integrated circuit) implements two modes of operation utilizing a common electron beam generator that produces an electron beam within a chamber. In the first mode, the electron beam interacts directly with the sample, and backscattered electrons, secondary electrons, and backward propagating fluorescent X-rays are measured. In the second mode, the electron beam interrogates the sample via X-rays generated by the electron beam within a target that is positioned between the electron beam generator and the sample. Transmitted X-rays are measured by a detector within the vacuum chamber. The sample is placed on a movable platform to precisely position the sample with respect to the electron beam. Interferometric and/or capacitive sensors are used to measure the position of the sample and movable platform to provide high accuracy metadata for performing high resolution three-dimensional sample reconstruction.

26 Claims, 24 Drawing Sheets

(51) Int. Cl.
  *G21K 7/00* (2006.01)
  *H01J 37/244* (2006.01)
  *H01J 37/28* (2006.01)
  *H01J 37/22* (2006.01)
  *H01J 37/20* (2006.01)
(52) U.S. Cl.
  CPC ............ *H01J 37/226* (2013.01); *H01J 37/28* (2013.01); *H01J 2237/20214* (2013.01); *H01J 2237/20221* (2013.01); *H01J 2237/20278* (2013.01); *H01J 2237/20292* (2013.01); *H01J 2237/226* (2013.01); *H01J 2237/2445* (2013.01); *H01J 2237/2448* (2013.01); *H01J 2237/24475* (2013.01); *H01J 2237/2611* (2013.01); *H01J 2237/2804* (2013.01); *H01J 2237/2806* (2013.01); *H01J 2237/2807* (2013.01)
(58) Field of Classification Search
  CPC ..... H01J 2237/24475; H01J 2237/2448; H01J 2237/24485; H01J 2237/2602; G01N 23/223; G01N 2223/076; G01N 23/2076; G01N 23/083; G01N 23/085; G01N 23/22; G01N 23/225; G21K 7/00
  USPC ........ 378/45, 10, 143, 44, 50; 250/310, 305, 250/307, 311, 370.07
  See application file for complete search history.

(56) References Cited

U.S. PATENT DOCUMENTS

| | | | | |
|---|---|---|---|---|
| 7,245,696 | B2* | 7/2007 | Yun | B82Y 10/00 378/44 |
| 7,990,543 | B1* | 8/2011 | Mello | G01B 11/2441 356/512 |
| 9,448,190 | B2* | 9/2016 | Yun | G01N 23/2076 |
| 9,594,036 | B2* | 3/2017 | Yun | G01N 23/223 |
| 9,646,732 | B2* | 5/2017 | Adler | G21K 7/00 |
| 9,823,203 | B2* | 11/2017 | Yun | H01J 35/08 |
| 9,984,852 | B1* | 5/2018 | Luiten | H01J 37/20 |
| 10,033,840 | B2* | 7/2018 | Vange | B60C 1/0016 |
| 2003/0106378 | A1* | 6/2003 | Giannakopoulos | G01B 11/16 73/788 |
| 2003/0194053 | A1* | 10/2003 | Schramm | G01N 23/223 378/45 |
| 2010/0045659 | A1* | 2/2010 | Yagi | G01N 23/22 345/418 |
| 2012/0326032 | A1* | 12/2012 | Benner | H01J 37/244 250/310 |
| 2015/0213995 | A1* | 7/2015 | Muray | H01J 37/04 250/305 |
| 2015/0276952 | A1* | 10/2015 | Morita | G01T 7/005 250/370.07 |
| 2015/0303021 | A1* | 10/2015 | Parker | H01J 35/08 378/10 |
| 2016/0027609 | A1* | 1/2016 | Sharma | H01J 37/226 250/307 |
| 2017/0178980 | A1* | 6/2017 | Owen | G01B 11/2441 |
| 2017/0200524 | A1 | 7/2017 | Adler | |
| 2017/0269011 | A1* | 9/2017 | Statham | G01N 23/2252 |
| 2018/0151326 | A1* | 5/2018 | Kieft | H01J 37/045 |
| 2018/0358199 | A1* | 12/2018 | Kumamoto | H01J 37/244 |
| 2019/0017948 | A1* | 1/2019 | Anan | G01N 23/223 |

OTHER PUBLICATIONS

Tilman Donath, Felix Beckmann, and Andreas Schreyer. Automated determination of the center of rotation in tomography data. J. Opt. Soc. Am., 23(5):1048-1057, 2006.

IC Noyan, SK Kaldor, P-C Wang, and J. Jordan-Sweet. A cost-effective method for minimizing the sphere-of-confusion error of x-ray microdiffractometers. Review of scientific instruments, 70(2):1300-1304, 1999.

Weihe Xu, Kenneth Lauer, Yong Chu, and Evgeny Nazaretski. A high-precision instrument for mapping of rotational errors in rotary stages. Journal of synchrotron radiation, 21(6):1367-1369, 2014.

Marcel Beister, Daniel Kolditz, and Willi A. Kalender. Iterative reconstruction methods in x-ray ct. Physica medica, 28(2):94-108, 2012.

David S. Rigie and Patrick J. La Rivière. Joint reconstruction of multi-channel, spectral ct data via constrained total nuclear variation minimization. Physics in medicine and biology, 60(5):1741, 2015.

Paulo RS Mendonca, Peter Lamb, and Dushyant V. Sahani. A flexible method for multi-material decomposition of dual-energy ct images. IEEE transactions on medical imaging, 33(1):99-116, 2014.

Kenneth Lange, Richard Carson, et al. Em reconstruction algorithms for emission and transmission tomography. J Comput Assist Tomogr, 8(2):306-16, 1984.

SH Manglos, GM Gagne, A Krol, FD Thomas, and R. Narayanaswamy. Transmission maximum-likelihood reconstruction with ordered subsets for cone beam ct. Physics in Medicine and Biology, 40(7):1225, 1995.

Chris Kamphuis and Freek J. Beekman. Accelerated iterative transmission ct reconstruction using an ordered subsets convex algorithm. IEEE Transactions on Medical Imaging, 17(6):1101-1105, 1998.

Hongqing Zhu, Huazhong Shu, Jian Zhou, and Limin Luo. A weighted least squares pet image reconstruction method using iterative coordinate descent algorithms. In Nuclear Science Symposium Conference Record, 2004 IEEE, vol. 6, pp. 3380-3384. IEEE, 2004.

Soo-Jin Lee. Accelerated coordinate descent methods for bayesian reconstruction using ordered subsets of projection data. In International Symposium on Optical Science and Technology, pp. 170-181. International Society for Optics and Photonics, 2000.

Peter J. Green. Bayesian reconstructions from emission tomography data using a modified em algorithm. IEEE transactions on medical imaging, 9(1):84-93, 1990.

Peter J. Green. On use of the em for penalized likelihood estimation. Journal of the Royal Statistical Society. Series B (Methodological), pp. 443-452, 1990.

Jean-Baptiste Thibault, Ken D. Sauer, Charles A. Bouman, and Jiang Hsieh. A three-dimensional statistical approach to improved image quality for multi-slice helical ct. Medical physics, 34(11):4526-4544, 2007.

Charles A. Bouman and Ken Sauer. A unified approach to statistical tomography using coordinate descent optimization. IEEE Transactions on image processing, 5(3): 480-492, 1996.

Ken Sauer and Charles Bouman. A local update strategy for iterative reconstruction from projections. IEEE Transactions on Signal Processing, 41(2):534-548, 1993.

Freek J. Beekman and Chris Kamphuis. Ordered subset reconstruction for x-ray ct. Physics in medicine and biology, 46(7):1835, 2001.

Yong Long and Jeffrey A. Fessler. Multi-material decomposition using statistical image reconstruction in x-ray ct. Proc. 2nd Intl. Mtg. on image formation in X-ray CT, pp. 413-416, 2012.

Sangtae Ahn, Jeffrey A. Fessler, Doron Blatt, and Alfred O. Hero. Convergent in-cremental optimization transfer algorithms: Application to tomography. IEEE Transactions on Medical Imaging, 25(3):283-296, 2006.

Zhou Yu, Jean-Baptiste Thibault, Charles A. Bouman, Ken D. Sauer, and Jiang Hsieh. Fast model-based x-ray ct reconstruction using spatially nonhomogeneous icd optimization. IEEE Transactions on image processing, 20(1):161-175, 2011.

Donghwan Kim, Debashish Pal, Jean-Baptiste Thibault, and Jeffrey A. Fessler. Accelerating ordered subsets image reconstruction for x-ray ct using spatially nonuniform optimization transfer. IEEE transactions on medical imaging, 32(11)1965-1978, 2013.

H. Malcolm Hudson and Richard S. Larkin. Accelerated image reconstruction using ordered subsets of projection data. IEEE transactions on medical imaging, 13(4):601-609, 1994.

Yong Long and Jeffrey A. Fessler. Multi-material decomposition using statistical image reconstruction for spectral ct. IEEE transactions on medical imaging, 33(8): 1614-1626, 2014.

(56) References Cited

OTHER PUBLICATIONS

Sascha Moehrs, Michel Defrise, Nicola Belcari, Alberto Del Guerra, Antonietta Bartoli, Serena Fabbri, and Gianluigi Zanetti. Multi-ray-based system matrix generation for 3d pet reconstruction. Physics in medicine and biology, 53(23):6925, 2008.
H. Heinrich, P. Ziegenhein, CP Kamerling, H. Froening, and U. Oelfke. Gpu-accelerated ray-tracing for real-time treatment planning. In Journal of Physics: Conference Series, vol. 489, p. 012050. IOP Publishing, 2014.
Peille et al., "Performance assessment of different pulse reconstruction algorithms for the ATHENA X-ray Integral Field Unit," Proc. SPIE 9905, Space Telescopes and Instrumentation 2016: Ultraviolet to Gamma Ray, 99055W (Jul. 11, 2016).
Fang Xu. Fast implementation of iterative reconstruction with exact ray-driven projector on gpus. Tsinghua Science & Technology, 15(1):30-35, 2010.
WJ Palenstijn, KJ Batenburg, and J. Sijbers. Performance improvements for iterative electron tomography reconstruction using graphics processing units (gpus). Journal of structural biology, 176(2):250-253, 2011.
Richard Gordon, Robert Bender, and Gabor T. Herman. Algebraic reconstruction techniques (art) for three-dimensional electron microscopy and x-ray photography. Journal of theoretical Biology, 29(3):471IN1477-476IN2481, 1970.
Anders H. Andersen and Avinash C. Kak. Simultaneous algebraic reconstruction technique (sart): a superior implementation of the art algorithm. Ultrasonic imaging, 6(1):81-94, 1984.
Fang Xu, Wei Xu, Mel Jones, Bettina Keszthelyi, John Sedat, David Agard, and Klaus Mueller. On the efficiency of iterative ordered subset reconstruction algorithms for acceleration on gpus. Computer methods and programs in biomedicine, 98(3):261-270, 2010.
Floro et al., "Curvature-Based Techniques for Real-Time Stress Measurement During Thin-Film Growth", Chapter 7 (p. 191) in "In Situ Real-Time Characterization of Thin Films", edited by Orlando Auciello and Alan R. Krauss, ISBN 0-471-24141-5, John Wiley & Sons, Inc. (2001).
Michal A. Brown, Tae-Soon Park, Ares Rosakis, Ersan Ustundag, Young Huang, Nobumichi Tamura, and Bryan Valek. A comparison of x-ray microdiffraction and coherent gradient sensing in measuring discontinuous curvatures in thin film: substrate systems. Journal of applied mechanics, 73(5):723-729, 2006.
T-S Park, S. Suresh, AJ Rosakis, and J. Ryu. Measurement of full-field curvature and geometrical instability of thin film-substrate systems through cgs interferometry. Journal of the Mechanics and Physics of Solids, 51(11):2191-2211, 2003.
Hansuk Lee, Ares J. Rosakis, and LB Freund. Full-field optical measurement of curvatures in ultra-thin-film-substrate systems in the range of geometrically nonlinear deformations. Journal of Applied Physics, 89(11):6116-6129, 2001.
AJ Rosakis, RP Singh, Y. Tsuji, E. Kolawa, and NR Moore. Full field measurements of curvature using coherent gradient sensing: application to thin film characterization. Thin Solid Films, 325(1):42-54, 1998.
Xue Feng, Yonggang Huang, Hanqing Jiang, Due Ngo, and Ares J. Rosakis. The effect of thin film/substrate radii on the stoney formula for thin film/substrate subjected to nonuniform axisymmetric misfit strain and temperature. Journal of Mechanics of Materials and Structures, 1(6):1041-1053, 2006.
Yasumasa Okada and Yozo Tokumaru. Precise determination of lattice parameter and thermal expansion coefficient of silicon between 300 and 1500 k. Journal of applied physics, 56(2):314-320, 1984.
Simos, Nick & Chu, Yong & Broadbent, A & Nazaretski, E & Margulies, Lawrence & Dyling, O & Shen, Q & Fallier, Martin. Achieving Vibration Stability of the NSLS-II Hard X-ray Nanoprobe Beamline. AIP Conference Proceedings, 1365 (2011).
Yong S. Chu. Preliminary Design Report for the Hard X-ray (HXN) Nanoprobe Beamline. NSLS-II Project, Brookhaven National Laboratory, 2010.

Yong Chu, Hanfei Yan, Evgeny Nazaretski, Sebastian Kalbfleisch, Xiaojing Huang, Kenneth Lauer, and Nathalie Bouet. Hard X-ray nanoprobe facility at the National Synchroton Light Source II. SPIE Newsroom, DOI: 10.1117/2.1201508.006068, 2015.
En-Te Hwu, Evgeny Nazaretski, Yong S. Chu, Huang-Han Chen, Yu-Sheng Chen, Weihe Xu, and Yeukuang Hwu. Design and characterization of a compact nano-positioning system for a portable transmission X-ray microscope. Review of Scientific Instruments, 84(12):123702, 2013.
Jungdae Kim, K Lauer, H. Yan, YS Chu, and E. Nazaretski. Compact prototype apparatus for reducing the circle of confusion down to 40 nm for x-ray nanotomography. Review of Scientific Instruments, 84(3):035006, 2013.
E. Nazaretski, Jungdae Kim, H. Yan, K. Lauer, D. Eom, D. Shu, J. Maser, Z. Pešic', U. Wagner, C. Rau, et al. Performance and characterization of the prototype nm-scale spatial resolution scanning multilayer Laue lenses microscope. Review of Scientific Instruments, 84(3):033701, 2013.
E. Nazaretski, X. Huang, H. Yan, K. Lauer, R. Conley, N. Bouet, J. Zhou, W. Xu, D. Eom, D. Legnini, et al. Design and performance of a scanning ptychography microscope. Review of Scientific Instruments, 85(3):033707, 2014.
E. Nazaretski, K. Lauer, H. Yan, N. Bouet, J. Zhou, R. Conley, X. Huang, W. Xu, M. Lu, K. Gofron, et al. Pushing the limits: an instrument for hard X-ray imaging below 20 nm. Journal of synchrotron radiation, 22(2):336-341, 2015.
E. Nazaretski, H. Yan, K. Lauer, X. Huang, W. Xu, S. Kalbfleisch, Hui Yan, Li Li, N Bouet, J. Zhou, et al. Nm-scale spatial resolution X-ray imaging with MLL nanofocusing optics: Instrumentational requirements and challenges. In AIP Conference Proceedings, vol. 1764, p. 040001. AIP Publishing, 2016.
Deming Shu, Evgeny Nazaretski, Jungdae Kim, Hanfei Yan, Kenneth Lauer, Brian Mullany, Dennis Kuhne, Jörg Maser, and Yong S. Chu. Optomechanical design of a multilayer Laue lens test bed for 10-nm focusing of hard X-rays. In Journal of Physics: Conference Series, vol. 463, p. 012029. IOP Publishing, 2013.
Andrea Somogyi, Kadda Medjoubi, Gil Baranton, Vincent Le Roux, Marc Ribbens, François Polack, Pascal Philippot, and J-P Samama. Optical design and multi-length-scale scanning spectro-microscopy possibilities at the Nanoscopium beamline of synchrotron soleil. Journal of synchrotron radiation, 22(4):1118-1129, 2015.
Matt Malloy, Brad Thiel, Benjamin D. Bunday, Stefan Wurm, Maseeh Mukhtar, Kathy Quoi, Thomas Kemen, Dirk Zeidler, Anna Lena Eberle, Tomasz Garbowski, Gregor Dellemann, Jan Hendrik Peters, "Massively parallel E-beam inspection: enabling next-generation patterned defect inspection for wafer and mask manufacturing," Proc. SPIE 9423, Alternative Lithographic Technologies VII, 942319 (Mar. 19, 2015).
Shammi Rahangdale, Yan Ren, CW Hagen, and P Kruit. Multi-beam scanning electron microscopy (mbsem) at 0.5 tb/s?. 14th International Congress for Stereology and Image Analysis, 2015.
Sin Cheng Siah, R Jaramillo, Rupak Chakraborty, Peter T Erslev, Cheng-Jun Sun, Tsu- Chien Weng, Michael F Toney, Glenn Teeter, and Tonio Buonassisi. X-ray absorption spectroscopy study of structure and stability of disordered (Cu2SnS3)1−x(ZnS)x alloys. Photovoltaics, IEEE Journal of, 5(1)372-377, 2015.
Qifeng Zhang, Evan Uchaker, Stephanie L Candelaria, and Guozhong Cao. Nanomaterials for energy conversion and storage. Chemical Society Reviews, 42(7):3127-3171, 2013.
Leslie J Allen, Adrian J D'Alfonso, Bert Freitag, and Dmitri O Klenov. Chemical mapping at atomic resolution using energy-dispersive x-ray spectroscopy. MRS bulletin, 37(01):47-52, 2012.
P Schlossmacher, DO Klenov, B Freitag, and HS Von Harrach. Enhanced detection sensitivity with a new windowless xeds system for aem based on silicon drift detector technology. Microscopy today, 18(04):14-20, 2010.
David B Williams, Adam J Papworth, and Masashi Watanabe. High resolution x-ray mapping in the stem. Journal of Electron Microscopy, 51(supplement):S113-S126, 2002.
Nestor J Zaluzec. Analytical formulae for calculation of x-ray detector solid angles in the scanning and scanning/transmission analytical electron microscope. Microscopy and Microanalysis, 20(04):1318-1326, 2014.

(56) References Cited

OTHER PUBLICATIONS

M Haider, S Uhlemann, and J Zach. Upper limits for the residual aberrations of a high-resolution aberration-corrected stem. Ultramicroscopy, 81(3):163-175, 2000.

Kayla X. Nguyen, Meagan E. Holtz, Justin Richmond-Decker and David A. Muller. Spatial resolution in scanning electron microscopy without a specimen vacuum chamber. Microscopy and Microanalysis, 22. 754-767, 2016.

Xueju Wang, Zhipeng Pan, Feifei Fan, Jiangwei Wang, Yang Liu, Scott X Mao, Ting Zhu, and Shuman Xia. Nanoscale deformation analysis with high-resolution transmission electron microscopy and digital image correlation. Journal of Applied Mechanics, 82(12):121001, 2015.

Ilya D Feranchuk, A Ulyanenkov, J Harada, and JCH Spence. Parametric x-ray radiation and coherent bremsstrahlung from nonrelativistic electrons in crystals. Physical Review E, 62(3):4225, 2000.

OL Krivanek, N Dellby, and MF Murfitt. Aberration-corrected scanning transmission electron microscopy of semiconductors. In Journal of Physics: Conference Series, vol. 326, p. 012005. IOP Publishing, 2011.

OL Krivanek, GJ Corbin, N Dellby, BF Elston, RJ Keyse, MF Murfitt, CS Own, ZS Szilagyi, and JW Woodruff. An electron microscope for the aberration-corrected era. Ultramicroscopy, 108(3):179-195, 2008.

Huolin L Xin and David A Muller. Aberration-corrected adf-stem depth sectioning and prospects for reliable 3d imaging in s/tem. Journal of electron microscopy, 58(3): 157-165, 2009.

Michael Bajura, Greg Boverman, John Tan, Gene Wagenbreth, Craig Milo Rogers, Michael Feser, Juana Rudati, Andrei Tkachuk, Stephen Aylward, and Patrick Reynolds. Imaging integrated circuits with x-ray microscopy. In Proc. 36th GO- MACTech Conf, pp. 1-4, 2011.

X-ray nanotomography imaging for circuit integrity. https://www-ssrl.slac.stanford.edu/content/science/highlight/2011-09-26/x-ray-nanotomography-imaging-circuit-integrity, 2011.

Eldad Haber and Michal Holtzman Gazit. Model fusion and joint inversion. Surveys in Geophysics, 34(5):675-695, 2013.

Bicer T., Gursoy D., Kettimuthu R., De Carlo F., Agrawal G., Foster I.T. (2015) Rapid Tomographic Image Reconstruction via Large-Scale Parallelization. In: Träff J., Hunold S., Versaci F. (eds) Euro-Par 2015: Parallel Processing. Euro-Par 2015. Lecture Notes in Computer Science, vol. 9233. Springer, Berlin, Heidelberg (2015).

Hong et al., "A New Workflow for x-ray fluorescence tomography: MAPSToTomoPy", Proc SPIE Int Soc Opt Eng. Aug. 9, 2015; 9592 (2015).

Di, Zichao, Leyffer, Sven and Wild, Stefan M. Optimization-based approach for joint x-ray fluorescence and transmission tomographic inversion. Siam J. Imaging Sciences, 9(1):1-23, 2016.

Ullom, JN and Doriese, WB and Fischer, DA and Fowler, JW and Hilton, GC and Jaye, C and Reintsema, CD and Swetz, DS and Schmidt, DR. Transition-edge sensor microcalorimeters for x-ray beamline science. Synchrotron Radiation News, 27(4): 24-27, 2014.

Mimura, Hidekazu and Handa, Soichiro and Kimura, Takashi and Yumoto, Hi- rokatsu and Yamakawa, Daisuke and Yokoyama, Hikaru and Matsuyama, Satoshi and Inagaki, Kouji and Yamamura, Kazuya and Sano, Yasuhisa and others. Breaking the 10 nm barrier in hard-x-ray focusing. Nature Physics, 6(2)122-125, 2010.

Edwards, Paul R and Martin, Robert W. Cathodoluminescence nano-characterization of semiconductors. Semiconductor Science and Technology, 26(6):064005, 2011.

Ashwin C Atre, Benjamin JM Brenny, Toon Coenen, Aitzol García-Etxarri, Albert Polman, and Jennifer A. Dionne. Nanoscale optical tomography with cathodoluminescence spectroscopy. Nature Nanotechnology, vol. 10, pp. 429-436, 2015.

Thonke, K and Tischer, I and Hooker, M and Schirra, M and Fujan, K and Wiedenmann, M and Schneider, R and Frey, M and Feneberg, M. Nanoscale characterisation of semiconductors by cathodoluminescence. In IOP Conference Series: Materials Science and Engineering, vol. 55, p. 012018. IOP Publishing, 2014.

R. Chivas and S. Silverman, "Adaptive grinding and polishing of packaged integrated circuits," 2014 IEEE International Reliability Physics Symposium, Waikoloa, HI, pp. FA.4.1-FA.4.6 (2014).

Chivas, Robert D. Adaptive grinding and polishing of silicon integrated circuits to ultrathin remaining thickness. In 41st International Symposium for Testing and Failure Analysis. Asm, 2015.

Manske, Eberhard and Jäger, Gerd and Hausotte, Tino and Füßl, Roland. Recent developments and challenges of nanopositioning and nanomeasuring technology. Measurement Science and Technology, 23(7):074001, 2012.

Saeed Olyaee and Samaneh Hamedi (Apr. 1, 2010). Nano-Metrology Based on the Laser Interferometers, Advances in Measurement Systems Milind Sharma, IntechOpen, DOI: 10.5772/8740. Available from: https://www.intechopen.com/books/advances-in-measurement-systems/nano-metrology-based-on-the-laser-interferometers (2010).

Xu, Feng and Helfen, Lukas and Suhonen, Heikki and Elgrabli, Dan and Bayat, Sam and Reischig, Péter and Baumbach, Tilo and Cloetens, Peter. Correlative nanoscale 3D imaging of structure and composition in extended objects. PLoS ONE, 7(11), 2012.

Brownlow, Les and Mayo, Sheridan and Miller, Peter and Sheffield-Parker, Julie. Towards 50-nanometre resolution with an sem-hosted x-ray microscope. Microscopy and Analysis, 112:13, 2006.

Schropp, A and Boye, P and Goldschmidt, A and Hönig, S and Hoppe, R and Patommel, J and Rakete, C and Samberg, D and Stephan, S and Schöder, S and Burghammer, M and Schroer, CG. Non-destructive and quantitative Imaging of a nano-structured microchip by ptychographic hard x-ray scanning microscopy. Journal of microscopy, 241(1):9-12, 2011.

Bleuet, Pierre and Cloetens, Peter and Gergaud, Patrice and Mariolle, Denis and Chevalier, Nicolas and Tucoulou, Rémi and Susini, Jean and Chabli, Amal. A hard x-ray nanoprobe for scanning and projection nanotomography. Review of scientific instruments, 80(5):056101, 2009.

Withers, Philip J. X-ray nanotomography. Materials today, 10(12):26-34, 2007.

S. C. Mayo, P. R. Miller, S. W. Wilkins, T. J. Davis, D. Gao, T. E. Gureyev, David Paganin, D. J. Parry, A. Pogany, and A. W. Stevenson. Quantitative x-ray projection microscopy: phase-contrast and multi-spectral imaging. Journal of microscopy, 207(2): 79-96, 2002.

SC Mayo, PR Miller, J Sheffield-Parker, Tim Gureyev, and SW Wilkins. Attainment of <60 nm resolution in phase-contrast x-ray microscopy using an add-on to an sem. In 8th International Conference on X-ray Microscopy, IPAP Conference Series, pp. 343-345, 2005.

S Mayo, T Davis, Timur Gureyev, P Miller, David Paganin, A Pogany, A Stevenson, and S Wilkins. X-ray phase-contrast microscopy and microtomography. Optics Express, 11(19):2289-2302, 2003.

John Amanatides, Andrew Woo, et al. A fast voxel traversal algorithm for ray tracing. In Eurographics, vol. 87, pp. 3-10, 1987.

Burnett, TL and McDonald, SA and Gholinia, A and Geurts, R and Janus, M and Slater, T and Haigh, SJ and Omek, C and Almuaili, F and Engelberg, DL and Thompson, GE and Withers, PJ. Correlative tomography. Scientific reports, 4, 2014.

Bradley K Alpert, W Bertrand Doriese, Joseph W Fowler, and Joel N Ullom. Predicted energy resolution of a running-sum algorithm for microcalorimeters. Journal of Low Temperature Physics, 167(5-6):582-587, 2012.

Filip Jacobs, Erik Sundermann, Bjorn De Sutter, Mark Christiaens, and Ignace Lemahieu. A fast algorithm to calculate the exact radiological path through a pixel or voxel space. Journal of computing and information technology, 6(1):89-34, 1998.

Robert L Siddon. Fast calculation of the exact radiological path for a three-dimensional ct array. Medical physics, 12(2):252-255, 1985.

JW Fowler, BK Alpert, WB Doriese, DA Fischer, Chemo Jaye, Young-Il Joe, GC O'Neil, DS Swetz, and JN Ullom. Microcalorimeter spectroscopy at high pulse rates: A multi-pulse fitting technique. The Astrophysical Journal Supplement Series, 219(2):35, 2015.

(56) References Cited

OTHER PUBLICATIONS

Johan Nuyts, Bruno De Man, Jeffrey A Fessler, Wojciech Zbijewski, and Freek J Beekman. Modelling the physics in the iterative reconstruction for transmission computed tomography. Physics in medicine and biology, 58(12):R63, 2013.

M Feser, C Jacobsen, P Rehak, and G DeGeronimo. Scanning transmission x-ray microscopy with a segmented detector. In Journal de Physique IV (Proceedings), vol. 104, pp. 529-534. EDP sciences, 2003.

Hakan Erdogan and Jeffrey A Fessler. Monotonic algorithms for transmission tomography. IEEE transactions on medical imaging, 18(9):801-814, 1999.

Bruno Golosio, Alexandre Simionovici, Andrea Somogyi, Laurence Lemelle, Marina Chukalina, and Antonio Brunetti. Internal elemental microanalysis combining x-ray fluorescence, compton and transmission tomography. Journal of applied Physics, 94(1): 145-156, 2003.

J Maser, B Lai, W Yun, SD Shastri, Z Cai, W Rodrigues, S Xua, and E Trackhtenberg. Near-field stacking of zone plates in the x-ray range. In Proc. of SPIE, vol. 4783, pp. 74-81, 2002.

Alvaro R De Pierro. A modified expectation maximization algorithm for penalized likelihood estimation in emission tomography. IEEE transactions on medical imaging, 14(1):132-137, 1995.

Ming Lu. Nanofabrication of Fresnel zone plates for soft X-ray imaging at carbon edge. Stony Brook University Dissertation, 2006.

Ji-Ho Chang, John MM Anderson, and John R Votaw. Regularized image reconstruction algorithms for positron emission tomography. IEEE transactions on medical imaging, 23(9):1165-1175, 2004.

Quantitative x ray analysis system. User's Manual and Guide to X Ray Fluorescence Technique. International Atomic Energy Agency, Feb. 2009, http://www-pub.iaea.org/MTCD/publications/PDF/IAEA-CMS-1_CD_web/PDF/CMS_21.pdf/. [Online; accessed Oct. 22, 2017].

VD Saveliev, L Feng, CR Tull, S Barkan, M Takahashi, and E Damron. Single- and four-element large area silicon drift detector x-ray spectrometers for xrf applications. SII Nano Technology USA Inc., http://www.dxcicdd.com/10/PDF/High%20Performance%20Spectrometers_DXC2010.pdf/. [Online; accessed Oct. 22, 2017].

LA Feldkamp, LC Davis, and JW Kress. Practical cone-beam algorithm. J. Opt. Soc. Am, 1 (6):612-619, 1984.

Fessler, "Statistical Image Reconstruction Methods for Transmission Tomography", downloaded from http://web.eecs.umich.edu/~fessler/book/fessler-00-sir,updated.pdf, Apr. 20, 2016.

Konstantins Jefimovs, Joan Vila-Comamala, Tero Pilvi, Jörg Raabe, Mikko Ritala, and Christian David. Zone-doubling technique to produce ultrahigh-resolution x-ray optics. Physical review letters, 99(26):264801, 2007.

Kazuto Yamauchi, Kazuya Yamamura, Hidekazu Mimura, Yasuhisa Sano, Akira Saito, Alexei Souvorov, Makina Yabashi, Kenji Tamasaku, Tetsuya Ishikawa, and Yuzo Mori. Nearly diffraction-limited line focusing of a hard-x-ray beam with an elliptically figured mirror. Journal of synchrotron radiation, 9(5):313-316, 2002.

Emanuel Levitan and Gabor T Herman. A maximum a posteriori probability expec- tation maximization algorithm for image reconstruction in emission tomography. IEEE Transactions on Medical Imaging, 6(3):185-192, 1987.

Björn Cederström, Mats Lundqvist, and Carolina Ribbing. Multi-prism x-ray lens. Applied physics letters, 81(8):1399-1401, 2002.

Yu I Dudchik, NN Kolchevsky, FF Komarov, Y Kohmura, M Awaji, Y Suzuki, and T Ishikava. Glass capillary x-ray lens: fabrication technique and ray tracing calcu- lations. Nuclear Instruments and Methods in Physics Research Section A: Accelerators, Spectrometers, Detectors and Associated Equipment, 454(2):512-519, 2000.

Joan Vila-Comamala, Sergey Gorelick, Elina Färm, Cameron M Kewish, Ana Diaz, Ray Barrett, Vitaliy A Guzenko, Mikko Ritala, and Christian David. Ultra-high resolution zone-doubled diffractive x-ray optics for the multi-kev regime. Optics express, 19(1):175-184, 2011.

Jeffrey A Fessler. Mean and variance of implicitly defined biased estimators (such as penalized maximum likelihood): Applications to tomography. IEEE Transactions on Image Processing, 5(3):493-506, 1996.

Patrick J La Rivière, David Billmire, Phillip Vargas, Mark Rivers, and Stephen R Sutton. Penalized-likelihood image reconstruction for x-ray fluorescence computed tomography. Optical Engineering, 45(7):077005, 2006.

Lin Fu, Tzu-Cheng Lee, Soo Mee Kim, Adam M Alessio, Paul E Kinahan, Zhiqian Chang, Ken Sauer, Mannudeep K Kalra, and Bruno De Man. Comparison between pre-log and post-log statistical models in ultra-low-dose ct reconstruction. IEEE transactions on medical imaging, 36(3):707-720, 2017.

Zhiqian Chang, Ruoqiao Zhang, Jean-Baptiste Thibault, Debashish Pal, Lin Fu, Ken Sauer, and Charles Bouman. Modeling and pre-treatment of photon-starved ct data for iterative reconstruction. IEEE transactions on medical Imaging, 36(1):277-287, 2017.

Stuart Geman and Donald Geman. Stochastic relaxation, gibbs distributions, and the bayesian restoration of images. IEEE Transactions on pattern analysis and machine intelligence, (6):721-741, 1984.

David A Chesler, Stephen J Riederer, and Norbert J Pelc. Noise due to photon counting statistics in computed x-ray tomography. Journal of computer assisted tomography, 1(1):64-74, 1977.

Lawrence A Shepp and Benjamin F Logan. The fourier reconstruction of a head section. IEEE Transactions on Nuclear Science, 21(3):21-43, 1974.

Fein, Geogg, "IARPA seeks enhanced method for integrated circuit validation", Jane's International Defence Review (ihs.com), Jan. 18, 2017.

Rowe, Martin, "Fake ICs: Another weapon in their detection", EDN Network, retrieved from https://www.edn.com/design/test-and-measurement/4458370/Fake-ICs-Another-weapon-in-their-detection (May 22, 2017).

Shimadzu, "Electron Probe Microanalyzer EPMA-8050G", retrieved from https://mahzadkala.com/wp-content/uploads/2015/09/EPMA-8050G.pdf on Jul. 16, 2018.

Zeiss, "ZEISS X-ray Tomography Solutions", retrieved from https://www.zeiss.com/microscopy/int/products/x-ray-microscopy.html on Jul. 16, 2018.

Yanxia Zhang. A 100-electron-beam source from a high brightness Schottky emitter for fast patterning applications. TU Delft, Delft University of Technology, pp. 1-70, 2008.

Yanxia Zhang. A 100-electron-beam source from a high brightness Schottky emitter for fast patterning applications. TU Delft, Delft University of Technology, pp. 71-147, 2008.

Y. Takeichi, N. Inami, H. Suga, T. Ueno, S. Kishimoto, Y. Takahashi, and K. Ono. Development of a compact scanning transmission X-ray microscope. In Journal of Physics: Conference Series, vol. 502, p. 012009. IOP Publishing, 2014.

Armin Hornung, Kai M. Wurm, Maren Bennewitz, Cyrill Stachniss, and Wolfram Burgard. Octomap: An efficient probabilistic 3d mapping framework based on octrees. Autonomous Robots, 34(3):189-206, 2013.

Tony F. Chan, Hongwei Li, Marius Lysaker, and Xue-Cheng Tai. Level Set Method for Positron Emission Tomography. International journal of biomedical imaging, Hindawi Publishing Corporation, vol. 2007, Article ID 26950, 2007.

Hakan Erdogan and Jeffrey A. Fessler. Ordered subsets algorithms for transmission tomography. Physics in medicine and biology, 44(11):2835, 1999.

Jeffrey A. Fessler, Edward P. Ficaro, Neal H. Clinthorne, and Kenneth Lange. Grouped-Coordinate Ascent Algorithms for Penalized-Likelihood Transmission Image Reconstruction. Medical Imaging, IEEE Transactions on, 16(2):166-175, 1997.

Meng Wu and Jeffrey A. Fessler. Gpu Acceleration of 3d Forward and Backward Projection Using Separable Footprints for X-Ray CT Image Reconstruction. In Proc. Intl. Mtg. Fully 3D Image Recon. Rad. Nuc. Med., pp. 56-9, 2011.

Christian G. Schroer. Reconstructing x-ray fluorescence microtomograms. Applied Physics Letters, 79(12):1912-1914, 2001.

(56) References Cited

OTHER PUBLICATIONS

Madison G. McGaffin and Jeffrey A. Fessler. Fast Gpu-Driven Model-Based X-Ray CT Image Reconstruction via Alternating Dual Updates. In Proc. Intl. Mtg. Fully 3D Image Recon. Rad. Nuc. Med., pp. 312-315, 2015.
Madison Gray McGaffin and Jeffrey A. Fessler. Edge-Preserving Image Denoising via Group Coordinate Descent on the GPU. Image Processing, IEEE Transactions on, 24 (4):1273-1281, 2015.
Raymond F. Egerton, Feng Wang, and Peter A. Crozier. Beam-Induced Damage to Thin Specimens in an Intense Electron Probe. Microscopy and Microanalysis, 12(01): 65-71, 2006.
Daniel P. Wilt, Richard C. Meitzler, and John P. DeVale. Metrics for TRUST in Integrated Circuits. Technical report, DTIC Document, GOMACTech 2008 Proceedings, 2008.
Cyril Crassin, Fabrice Neyret, Sylvain Lefebvre, and Elmar Eisemann. Gigavoxels: Ray-guided streaming for efficient and detailed voxel rendering. In Proceedings of the 2009 symposium on Interactive 3D graphics and games, pp. 15-22. ACM SIGGRAPH Symposium on Interactive 3D Graphics and Games (I3D), 2009.
Jinyi Qi and Richard M. Leahy. Iterative reconstruction techniques in emission computed tomography. Physics in medicine and biology, 51(15): R541, 2006.
Xiaojing Huang, Raymond Conley, Nathalie Bouet, Juan Zhou, Albert Macrander, Jorg Maser, Hanfei Yan, Evgeny Nazaretski, Kenneth Lauer, Ross Harder, et al. Achieving hard x-ray nanofocusing using a wedged multilayer laue lens. Optics express, 23(10):12496-12507, 2015.
Hanfei Yan, Evgeny Nazaretski, Kenneth Lauer, Xiaojing Huang, Ulrich Wagner, Christoph Rau, Mohammed Yusuf, Ian Robinson, Sebastian Kalbfleisch, Li Li, et al. Multimodality hard-x-ray imaging of a chromosome with nanoscale spatial resolution. Scientific Reports, 6:20112, 2016.
Star Cryoelectronics MICA-1600 X-Ray Spectrometer. http://starcryo.com/ microcal-x-ray-spectrometers/. [Online; accessed Mar. 10, 2016].
Workshop of Industrial Research at NSLS-II: A Report from the Organizing Committee. NSLS-II Project, Brookhaven National Library, 2014.
Ullom, Joel N and Bennett, Douglas A. Review of superconducting transition-edge sensors for x-ray and gamma-ray spectroscopy. Superconductor Science and Technology, 28(8):84003-84038, 2015.
JP Hays-Wehle, DR Schmidt, JN Ullom, and DS Swetz. Thermal conductance engineering for high-speed TES microcalorimeters. Journal of Low Temperature Physics, pp. 492-497, 2015.
Doriese et al., "Developments in Time-Division Multiplexing of X-ray Transition-Edge Sensors", Journal of Low Temperature Physics, vol. 184, Issue 1-2, pp. 389-395 (2016).
MRJ Palosaari, KM Kinnunen, J Julin, M Laitinen, M Napari, T Sajavaara, WB Doriese, J Fowler, C Reintsema, D Swetz, et al. Transition-edge sensors for particle induced x-ray emission measurements. Journal of Low Temperature Physics, 176(3-4):285-290, 2014.
DA Bennett, RD Horansky, DR Schmidt, AS Hoover, R Winkler, BK Alpert, JA Beall, WB Doriese, JW Fowler, CP Fitzgerald, et al. A high resolution gamma-ray spectrometer based on superconducting microcalorimeters. Review of Scientific Instruments, 83 (9):093113, 2012.
DS Swetz, DA Bennett, KD Irwin, DR Schmidt, and JN Ullom. Current distribution and transition width in superconducting transition-edge sensors. Applied Physics Letters, 101(24):242603, 2012.
Jens Uhlig, Wilfred Fullagar, JN Ullom, WB Doriese, JW Fowler, DS Swetz, N Gador, SE Canton, K Kinnunen, IJ Maasilta, et al. Table-top ultrafast x-ray microcalorimeter spectrometry for molecular structure. Physical review letters, 110(13):138302, 2013.
Daniel F. Yu and Jeffrey A. Fessler. Edge-preserving tomographic reconstruction with nonlocal regularization. Medical Imaging, IEEE Transactions on, 21(2):159-173, 2002.
Emil Y Sidky, Chien-Min Kao, and Xiaochuan Pan. Accurate image reconstruction from few-views and limited-angle data in divergent-beam ct. Journal of X-ray Science and Technology, 14(2):119-139, 2006.
Martin Storath, Andreas Weinmann, Jürgen Frikel, and Michael Unser. Joint image reconstruction and segmentation using the potts model. Inverse Problems, 31(2): 025003, 2015.
John P Hogan, Robert A Gonsalves, and Allen S Krieger. Fluorescent computer tomography: a model for correction of x-ray absorption. IEEE Transactions on Nuclear Science, 38(6):1721-1727, 1991.
M Holler, A Diaz, M Guizar-Sicairos, P Karvinen, Elina Färm, Emma Härkönen, Mikko Ritala, A Menzel, J Raabe, and O Bunk. X-ray ptychographic computed tomography at 16 nm isotropic 3d resolution. Scientific Reports 4, 2014.
Martin Dierolf, Andreas Menzel, Pierre Thibault, Philipp Schneider, Cameron M Kewish, Roger Wepf, Oliver Bunk, and Franz Pfeiffer. Ptychographic x-ray computed tomography at the nanoscale. Nature, 467(7314):436-439, 2010.
Rina Foygel Barber, Emil Y Sidky, Taly Gilat Schmidt, and Xiaochuan Pan. An algorithm for constrained one-step inversion of spectral ct data. arXiv preprint arXiv:1511.03384, 2015.
Martin D de Jonge and Stefan Vogt. Hard x-ray fluorescence tomography—an emerging tool for structural visualization. Current opinion in structural biology, 20(5):606-614, 2010.
Ruoqiao Zhang, Jean-Baptiste Thibault, Charles A Bouman, Ken D Sauer, and Jiang Hsieh. A model-based iterative algorithm for dual-energy x-ray CT reconstruction. In Proc. Int. Cont. Image Form. in X-ray CT, pp. 439-443, 2012.
Carsten O Schirra, Ewald Roessl, Thomas Koehler, Bernhard Brendel, Axel Thran, David Z Pan, Mark A Anastasio, and Roland Proksa. Statistical reconstruction of material decomposed data in spectral CT. Medical Imaging, IEEE Transactions on, 32 (7):1249-1257, 2013.
Xu, Jiaofeng, "Modeling and Development of Iterative Reconstruction Algorithms in Emerging X-ray Imaging Technologies", All Theses and Dissertations (ETDs). 1270, available at https://openscholarship.wustl.edu/etd/1270 (2014).
JK Lim, P Frigola, G Travish, JB Rosenzweig, SG Anderson, WJ Brown, JS Jacob, CL Robbins, and AM Tremaine. An adjustable, short focal length permanent-magnet quadrupole based electron beam final focus system. Physical Review Special Topics—Accelerators and Beams, 8(7):072401, 2005.
Mohammadi-Gheidari et al., "Electron optics of multi-beam scanning electron microscope", Nuclear Instruments and Methods in Physics Research A 645, 60-67 (2011).
A. L. Eberle, S. Mikula, R. Schalek, J. W. Lichtman, M. L. Knothetate, and D. Zeidler. High-resolution, high-throughput imaging with a multi-beam scanning electron microscope. J. Microscopy, 259:114-120, 2015.
Anna Lena Keller, Dirk Zeidler, Thomas Kemen, "High throughput data acquisition with a multi-beam SEM," Proc. SPIE 9236, Scanning Microscopies 2014, 92360B (Sep. 16, 2014).
P. C. Post, A. Mohammadi-Gheidari, C. W. Hagen, and P. Kruit. Parallel electron-beam-induced deposition using a multi-beam scanning electron microscope. Journal of Vacuum Science & Technology B, 29(6):06F310, 2011.
Yanxia Zhang and Pieter Kruit. Design of a high brightness multi-electron-beam source. Physics Procedia, 1(1):553-563, 2008.

* cited by examiner

NONDESTRUCTIVE SAMPLE IMAGING

STATEMENT OF GOVERNMENT INTEREST

The invention was made with United States Government support under contract FA8650-17-C-9114 awarded by the United States Air Force, and the United States Government has certain rights in this invention.

FIELD OF THE DISCLOSURE

This disclosure relates to systems and methods for nondestructively imaging a sample having a three-dimensional (3D) structure.

BACKGROUND

In certain situations, it can be important to accurately image a sample having a 3D structure with sub-micron or nanoscale features. One example of a 3D structure is an integrated circuit (IC) which refers to a broad category of electronic circuits residing on "chips" that may be further developed as circuit cards and boards. ICs are used in a wide variety of applications where the integrity of the IC is important and where it is necessary to obtain accurate verification of the contents of the IC, or perform a reliability analysis through physical inspection. The integrity and reliability are particularly critical, for example, for ICs used in military applications. Counterfeit or otherwise fake ICs are an increasingly serious problem, particularly when the counterfeit or otherwise fake IC performs at a substandard level in a critical application. Additionally, with ever-advancing technology nodes and decreasing critical dimensions, the potential for failure due to manufacturing variability and manufacturing defects increases correspondingly. To this end, ensuring accurate, reliable, and legitimate IC structure can be critical to ensure precise operation of certain systems, devices, and components. The ability to characterize manufacturing variability and to image and estimate the physical effect of IC degradation processes can potentially provide valuable feedback to IC designers and foundries.

BRIEF DESCRIPTION OF THE DRAWINGS

Features of embodiments of the claimed subject matter will become apparent as the following Detailed Description proceeds, and upon reference to the Drawings, wherein like numerals depict like parts.

Figure 1:
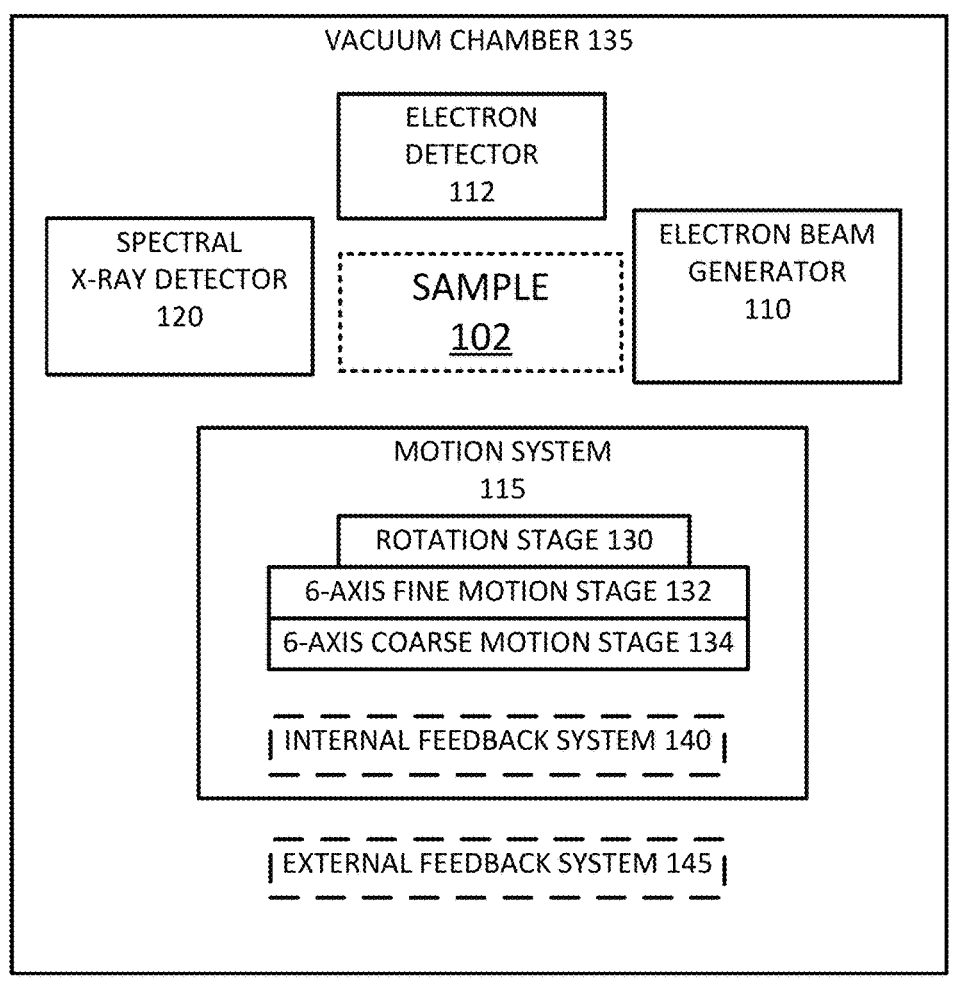
FIG. 1 is an overview block diagram illustrating an example system for implementing one or more embodiments of the present disclosure for imaging a sample having a complex structure, such as an IC.

Although the following Detailed Description will proceed with reference being made to illustrative embodiments, many alternatives, modifications, and variations thereof will be apparent in light of the present disclosure.

DETAILED DESCRIPTION

In accordance with one or more embodiments of the present disclosure, a system and various methods are provided for imaging a sample having a complex or otherwise 3D structure, such as an IC. The system and method achieve high resolution imaging of samples having complex structures within a reasonable amount of time (for example, within about one month or less for a typical IC die). In general, the systems and methods disclosed herein are capable of resolving the smallest features of the sample being imaged, such as individual transistors of an IC sample. While the size of these features will depend on the particular lithography techniques used to fabricate an integrated circuit, in certain embodiments the minimum resolvable feature size is between 1 nm and 100 nm, between 5 nm and 75 nm, between 8 nm and 50 nm, or between 10 nm and 45 nm. In some specific implementations features of size 10 nm, 14 nm, 22 nm, or 45 nm can be resolved. In one example, the system effectively and efficiently operates with at least 10 nm resolution. Such a system performs non-destructive testing and can be employed in an automated fashion as part of a manufacture, reliability, and/or inspection process. In accordance with an embodiment, the system is a tabletop system, meaning it is small enough to be placed, for example, on a table or support platform within a single room. The system has two modes of operation and includes a motion system for securely receiving, mounting, positioning, translating, and rotating a sample to be imaged. Both modes of operation use an electron beam generator (such as an electron column from a scanning electron microscope (SEM) and the resulting electron beam (also referred to as an "e-beam") as a primary particle (or excitation) source for imaging the sample. In the first mode (E-mode) of operation, the collected X-rays, back-scattered electrons (BSE), and secondary electrons (SE) are used to perform a chemical and structural analysis, and in the second mode (X-mode) of operation, the collected X-rays are used to perform an element density or attenuation reconstruction analysis of the sample. The E-mode of operation is for imaging the IC front-end (device layer) and potentially some low-metal i.e., M1, M2 layers, and the X-mode of operation is for imaging the IC back-end (metal layers) and potentially some features of the device layer. The electron beam in the E-mode of operation interacts with the sample directly, such that BSE, SE, and fluorescent X-rays are measured by appropriate detectors, in accordance with an embodiment of the present disclosure. The X-mode of operation uses a target (for example, a thin-film of metallic material such as gold, or a patterned thin-film with multiple materials) in which primary particles from the electron beam induce X-ray emission of characteristic lines via fluorescence as well as Bremsstrahlung radiation. These X-rays are measured by appropriate detector(s), in accordance with an embodiment of the present disclosure. The sample can be placed on a motion and metadata collection system to further improve accuracy in imaging of the sample so that a desired area of the sample is at a precise location with respect to the electron beam, and placed to provide appropriate X-ray and geometric data in a tomographic series for inversion of the sample using suitable algorithms and geometric sampling diversity. Interferometric and distance sensors (sometimes called interferometers or interferometric sensors) and capacitive distance sensors (sometimes called capacitive sensors) can be used to provide the aforementioned metadata to perform position estimation and tracking of the motion system moveable elements and that of the sample, as will be appreciated in light of the present disclosure. Various error correction techniques are disclosed to enhance the structure estimation, as will be appreciated in light of the present disclosure.

One existing device for imaging a sample having a complex structure, such as an IC, is the synchrotron, which supports multiple relevant techniques such as transmission tomography, X-ray fluorescence tomography, and coherent diffraction imaging (CDI). However, there are several non-trivial issues that arise from using a synchrotron for this purpose. Synchrotron storage rings are massive devices that can have a circumference of about one mile. A synchrotron and associated beamlines and end-stations are also expensive (typically requiring a national facility) and generally require a long period of time (e.g., 6 months or longer) to image an entire IC die. Access is on a competitive basis and there can be a long wait period due to limited availability. Most synchrotron techniques also disadvantageously typically require X-ray focusing optics to perform imaging of the sample, which can limit sample size and reduce efficiency in photon flux. Another existing technique for imaging a sample involves iterative use of a SEM and sample delayering. This can be performed with lab equipment in a single room, but requires destructive processing, whereby layers are iteratively imaged and removed, for example with chemical-mechanical polishing (CMP), until the entire chip has been imaged. This is time consuming, and once a layer is destroyed, it can no longer be re-imaged.

Thus, and in accordance with one or more embodiments of the present disclosure, non-destructive techniques are disclosed for imaging a sample having a complex structure. The techniques can be embodied, for instance, in a system having a relatively small footprint (as compared with a synchrotron), for example which can fit within a single room having a perimeter of tens of feet, thereby providing a tabletop or otherwise relatively small imaging system. The techniques also provide a significantly less expensive system that does not require X-ray lenses for imaging the complex samples, according to some embodiments. The technique uses a small x-ray focal spot size for achieving high-resolution imaging, which is achieved with a "target" design rather than with a lens or other focusing optics. The techniques further allow for imaging to be completed in a relatively short period of time (e.g., one month or considerably less depending upon the specifics of the sample and the desired output). It will be appreciated in light of the present disclosure that although shown and described with respect to imaging an IC structure, the techniques herein can be likewise applicable to non-destructively imaging other complex 3D structures as well, including energy conversion and storage structures (e.g., batteries), nanoelectronics structures, and biological tissues with appropriate preparation (e.g., brain matter).

General Overview

Disclosed herein are systems and methods for imaging a sample, such as an IC. The system includes a sample holder (and a sample/target assembly), a motion system, an electron beam generator, an electron detector (such as a BSE or SE detector), a first energy-resolving (or spectral energy) detector, and a second spectral energy detector, in accordance with an embodiment of the present disclosure. The first and second detectors may be, for instance, spectral energy detectors such as silicon drift detectors (SDDs), and/or superconducting sensor technology such as the transition edge sensor (TES) for extremely high spectral resolution (providing such benefits as enhanced SNR and ability to separately detect and resolve individual spectral lines). In a first mode of operation for the system, which may be referred to herein as "E-mode", BSE and SE are collected to provide structural and/or chemical information about the front-end of the IC. In addition, structural and chemical analysis of the IC front-end is achieved with X-ray fluorescence measurements resulting from electron beam induced interaction within the sample and measured by one or both of the first and second spectral energy detectors. In a second mode of operation of the system, which may be referred to herein as "X-mode", fluorescent X-rays generated by electron beam interaction with a manufactured target are used to perform transmission absorption tomography for estimation of an attenuation model at a given X-ray energy or spectral computed tomography using multiple X-ray energies for estimation of an atomic element density model, and are measured using one or both of the first and second detectors, in accordance with an embodiment of the present disclosure. While use of two separate X-ray detectors may enhance data collection efficiency, in certain embodiments a single X-ray detector is used. In E-mode of such embodiments, a SDD associated with the SEM can be used instead of a dedicated X-ray detector.

In some embodiments, interferometric sensors and capacitive sensors are included in the system to acquire measurements (metadata) for performing position estimation of one or more of the platform components to improve resolution and accuracy of the sample estimation from the system. The sensors and target/sensor assembly can include, for example, (1) an interferometer tower proximal to prepared and highly reflective surfaces on the motion system, and providing a stable reference position with which to precisely measure and track interferometrically the position of the motion system within a given coordinate system, or (2) capacitive sensors proximal to the motion system to detect movement and accurately measure distance. Any motion and/or drift of the electron beam can thus be taken into account and compensated for when generating a 3D reconstruction of the IC. In some embodiments, the motion system provides thirteen degrees-of-freedom by including a rotation stage (one degree-of-freedom), a fine six-axis motion stage (six degrees-of-freedom), and a coarse six-axis motion stage (six degrees-of-freedom). As used herein, a "degree-of-freedom" refers to a parameter of a system that may vary independently of other parameters, such as the various axes of motion referred to above, and may be referred to as "DoF" or "DOF".

In accordance with an embodiment of the present disclosure, the E-mode of operation is particularly well-suited for imaging individual components of transistors, including the channel, the gate, and the source and drain contacts and together composing the front-end-of-the-line (FEOL). The spectral X-ray detector is used in the E-mode to measure characteristic X-rays from the dopants, contacts, and oxides, etc., as will be appreciated, and which can be achieved using low spectral resolution X-ray detector technology such as SDDs or higher resolution superconducting technologies. The BSE detector and SE detector measure BSE and SE that are generated at various depths of the IC and the data thus collected can be processed to form images of IC features at corresponding depths, as will be appreciated in light of the present disclosure. In accordance with an embodiment of the present disclosure, the X-mode of operation is particularly useful for identifying metal traces (e.g., aluminum, copper, tungsten) and the other back-end-of-the-line (BEOL) structures of the IC stack.

The system and various methods disclosed herein provide both output data (such as X-ray fluorescence images, BSE images, and SE images, etc.) as well as metadata, which is information about the state of the system or a part of the system itself (such as interferometric data, the location of the electron beam generator, location of the motion system, etc.). For instance, the laser interferometric sensors and capacitive sensors provide metadata measurements for estimation of the motion system. The acquired metadata can be filtered to smooth the outputs using any suitable filtering techniques. The acquired images can be rectified (by projection onto a common image plane) and correlated to a reference image to computing drive and estimate center of rotation. By gathering both the data and metadata, accuracy of IC imaging is further enhanced. The spatial origin volume for characteristic X-rays generated in this way are spatially attributed by virtue of the energy sensitive detectors used in the system.

System Architecture

FIG. 1 is an overview block diagram of an example system for implementing one or more embodiments of the present disclosure for imaging a sample having a 3D structure, such as an IC. The system 100 is for imaging a sample 102 and includes an electron beam generator 110, an electron detector 112, a spectral X-ray detector 120, and a motion system 115. The electron beam generator 110, electron detector 112, spectral X-ray detector 120, and motion system 115 are within a vacuum chamber 135. As used herein, the term "vacuum chamber" refers to an enclosure from which gases are at least partially removed, thus resulting in a reduced-pressure environment. The motion system 115 in this example provides up to thirteen degrees-of-freedom, greater than 1 cm of linear travel in six axes, sub-nanometer resolution in six axes, the ability to move point-to-point or raster scan with an average velocity of at least 0.5 mm/sec, at least 1.0 mm/sec, or at least 2.0 mm/sec in various embodiments. The motion also provides the ability to scan in any plane rotated about the vertical axis within a range of at least ±45 degrees. This design is suitable for two-dimensional E-mode image scanning, and 3D X-mode tomography, and does not preclude introduction of additional degrees-of-freedom. Mechanical translation stages having a larger range of motion tend to be less precise, accurate, and repeatable. Thus, the motion system 115 disclosed herein has sufficient movement yet provides high resolution, precision, and accuracy, to perform the motion necessary for imaging.

To achieve motion requirements and accuracy requirements, the motion system 115 includes a rotation stage 130, a fine motion stage 132, and a coarse motion stage 134, as shown in FIG. 1. The fine motion stage 132 utilizes a monolithic device connected by integrated flexures that are driven by piezoelectric crystal devices. Capacitive sensors provide feedback for the fine motion stage 132. Integral flexures within the fine motion stage 132 provide frictionless motion and six degrees-of-freedom, and the piezoelectric crystal devices have high stiffness, can be made to grow or shrink with high precision, and include embedded capacitive sensors to provide sufficiently resolute feedback. The coarse motion stage 134 utilizes multiple single axis stages connected in a variety of geometries and combinations, such as the hexapod configuration shown and described herein. Other configurations will be apparent. Although the coarse motion stage 134 has a greater range of travel as compared to the fine motion stage 132, its motion is less resolute, less accurate, and less repeatable than a piezoelectric-driven flexure stage. By placing the fine motion system upon the coarse motion system, this provides the long travel afforded by the coarse motion system, with the high accuracy afforded by the fine motion system. Further, combining the motion stages with the rotation stage 130 allows for rotation in all planes. It will be appreciated that in some embodiments, the rotation stage 130 may be omitted, and the motion system 115 will thus just include the fine motion stage 132 and the coarse motion stage 134. A coarse motion hexapod configuration for the course motion stage 134, as will be appreciated in light of the present disclosure, has the advantage of providing a symmetrical, stiff, approximately cylindrical six degree-of-freedom system resulting in a powerful, rigid base structure. Placing a smaller, lighter, piezoelectric-driven monolithic fine motion stage 132 on top of a hexapod yields a fine motion system with long travel, a low center of gravity, high stiffness, and high speed scanning over small areas. Thus, a large range of motion is provided without sacrificing accuracy or precision. In addition, adding the rotation stage 130 between the fine motion stage 132 and the sample 102 can advantageously increase depth resolution in certain implementations. Because the rotation stage 130 is a long travel device it induces more error than the fine motion stage 132. Furthermore, because the sample 102 is positioned some distance above the plane of the rotating platform of the rotation stage 130, Abbé errors, also sometimes called sine errors, may occur. To recover from this non-optimal rotary motion, a reference cylinder having a flat mirror on one end can be used, as will be explained in turn.

The system 100 also provides various levels of feedback to correct any errors that may arise in the processing of data. The system 100 can include an internal feedback system 140, which is internal to the motion system 115 itself. All coarse axes have an internal encoder (not shown) that provides position feedback, as will be appreciated. The rotation stage axis has an internal encoder that provides position feedback, and all fine motion axes have internal capacitive sensor feedback. Each axis uses its intrinsic internal feedback device to be driven in closed loop control, as will be appreciated in light of the present disclosure. Internal feedback refers to feedback from distance sensing transducers located inside a stage and along a single axis and are internal to the motion system 115. Internal feedback errors compound as one axis is moved by other axes, so in certain implementations an external feedback system 145 is provided as well.

The external feedback system 145 is external to the motion system 115, but is also contained within the vacuum chamber 135. The external feedback system 145 can include interferometric sensors and capacitive sensors that are configured to externally monitor the position of the motion system 115, and to provide feedback to a motion system controller to correct any errors in the positioning of the motion system 115. The external feedback can be supplied by an array of sensors attached to a metering structure (for example, an interferometer tower, as described herein) that supports and surrounds the entire motion system 115 with distance sensors held with high dimensional stability. The external feedback sensors monitor the position and orientation of the sample 102 itself or an object in rigid contact with the sample 102 itself located as close to the sample 102 as possible. The external feedback system 145 described herein can improved the accuracy of the sample position feedback compared to a system having only internal feedback devices. An additional level of feedback can be added as well, as will be described in turn.

The system 100 can further include a vision feedback system 150, which may operate in real-time or at a later time in an open loop correction or analysis. The vision feedback system 150 can be a custom machine vision algorithm that acquires data gathered by the system 100 and identifies particular features within the sample 102 to aid in error correction for the system 100 and further analysis of the sample 102. For example, edge detection, feature recognition, mapping, contrast, etc., could be used to identify features of the sample 102 and provide a third layer of feedback for the system 100. In one embodiment the vision feedback system 150 resides within the chamber 135. For example, in certain embodiments a SEM provides functionality associated with the vision system.

The system 100 implements a stitching technique, whereby a plurality of areas of interest of the complex 3D structure are imaged and their geometric information is stored, as will be appreciated in light of the present disclosure. Then, the images of the areas of interest are stitched together to form a full two-dimensional geometry map of the sample 102. The stitching technique is used in order to overcome the travel and accuracy limitations described herein. Placing the fine motion system on top of the coarse motion system overcomes these limitations in travel and accuracy.

Figure 2:
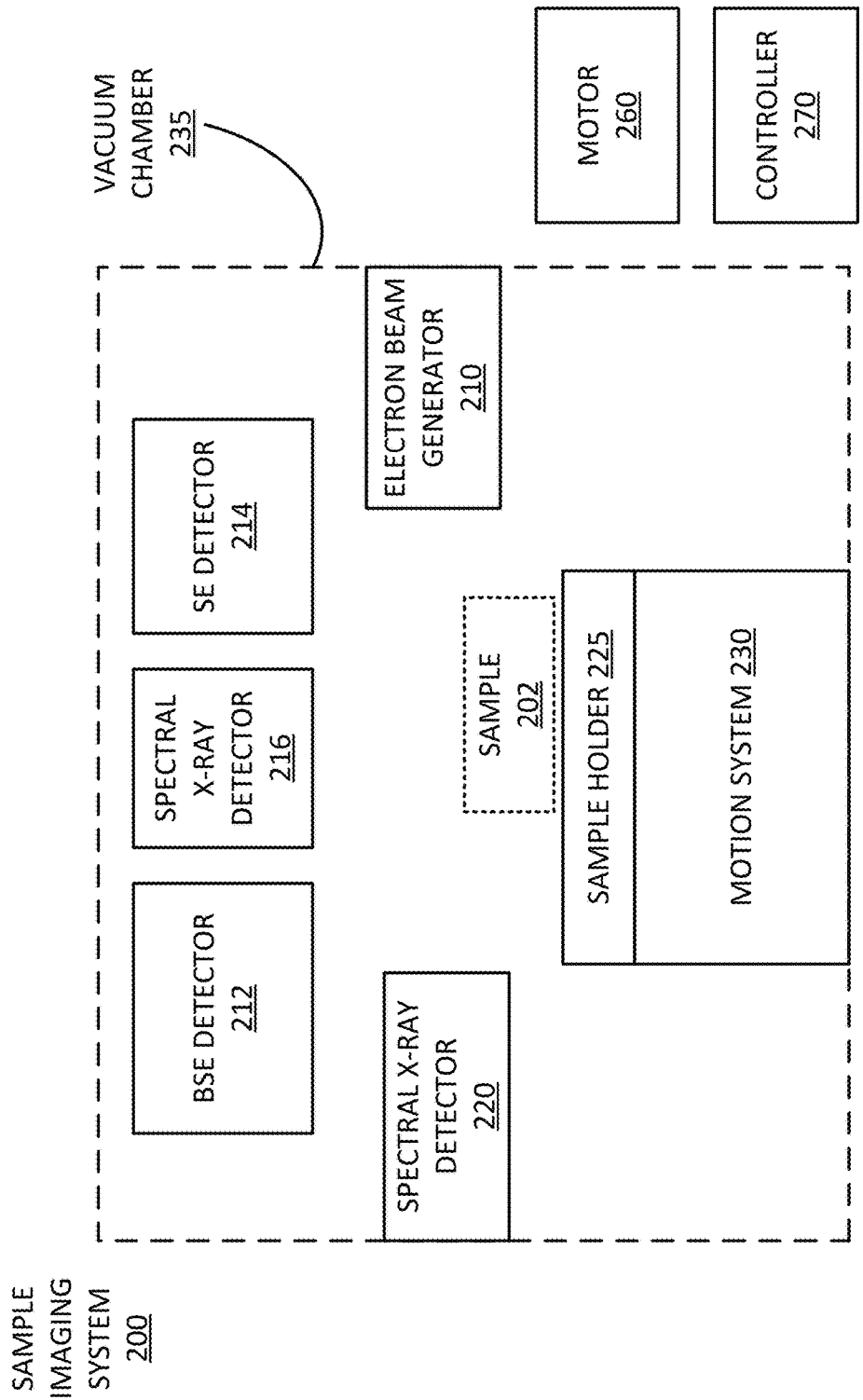
FIG. 2 is a block diagram illustrating an example system within a vacuum chamber for implementing one or more embodiments of the present disclosure for imaging a sample having a complex structure, such as an IC.

FIG. 2 is a block diagram illustrating an example system for implementing one or more embodiments of the present disclosure for imaging a sample. The example sample imaging system 200 for imaging a sample 202 operates in two modes of operation, including a first "E-mode" of operation and a second "X-mode" of operation. As will be appreciated in light of the present disclosure, the E-mode can be useful for inferring front-end structures (location of transistors, gates, contacts, and doping). The E-mode of operation is, for example, useful for acquiring information about the first metal layer (referred to as Metal 0, or M0), which is typically made of tungsten or tungsten alloys. The X-mode is also useful for gathering IC composition data, particularly from back-end metal layers and dielectrics. The data acquired in E-mode provides a map of the device layer of the IC, and depending on the features defined therein, can be used to guide the overall data acquisition plan in the X-mode of operation as well as to select a small region for particularly intense data collection (e.g., high dwell time, high spatial density for high accuracy reconstruction to derive model priors that are used in reconstruction in the remainder of the IC). Both modes of operation use an electron beam generator 210 and the electron beam it produces as a source for electron scattering or electron-induced fluorescence. The E-mode directly interacts with the sample 202 via electrons scattering and measures BSE, SE, and X-rays by appropriate detectors, in accordance with an embodiment of the present disclosure. The X-mode interrogates the sample 202 via X-rays generated in a target positioned between the sample 202 and the electron beam generator source, in accordance with an embodiment of the present disclosure.

The system 200 includes the electron beam generator 210, a BSE detector 212, a SE detector 214, one or more energy-sensitive (spectral) X-ray detectors 216, 220, a sample holder 225, and a motion system 230, contained within a vacuum chamber 235, in accordance with an embodiment of the present disclosure. The sample holder 225 also serves as a holder for the target/sample assembly. Although BSE and SE are detected, it will be appreciated in light of the present disclosure that any electron detector could be used to gather information about the structure of the sample 202. Moreover, it will be appreciated that while the present disclosure emphasizes same-side electron detection (i.e., back-scatter mode), this does not preclude the use of an electron detector including a pixelated array electron detector in a transmission mode, aligned along the optical axis of the electron beam, or otherwise. Any electron detector or appropriate detector can be implemented that uses information generated by an electron beam. For example, an array of a plurality of SDDs or of TESs can be used to speed up any chemical mapping analysis that is performed on the data. Alternatively, electron detector arrays similar to those used in transmission electron microscopes (TEMs) can be configured on the backside (opposite beam side) of the sample 202. Such detectors would dominantly be used for a prepared sample rather than a target/sample assembly, though a target/sample assembly is not precluded. Other detectors will be apparent in light of the present disclosure.

Figure 16:
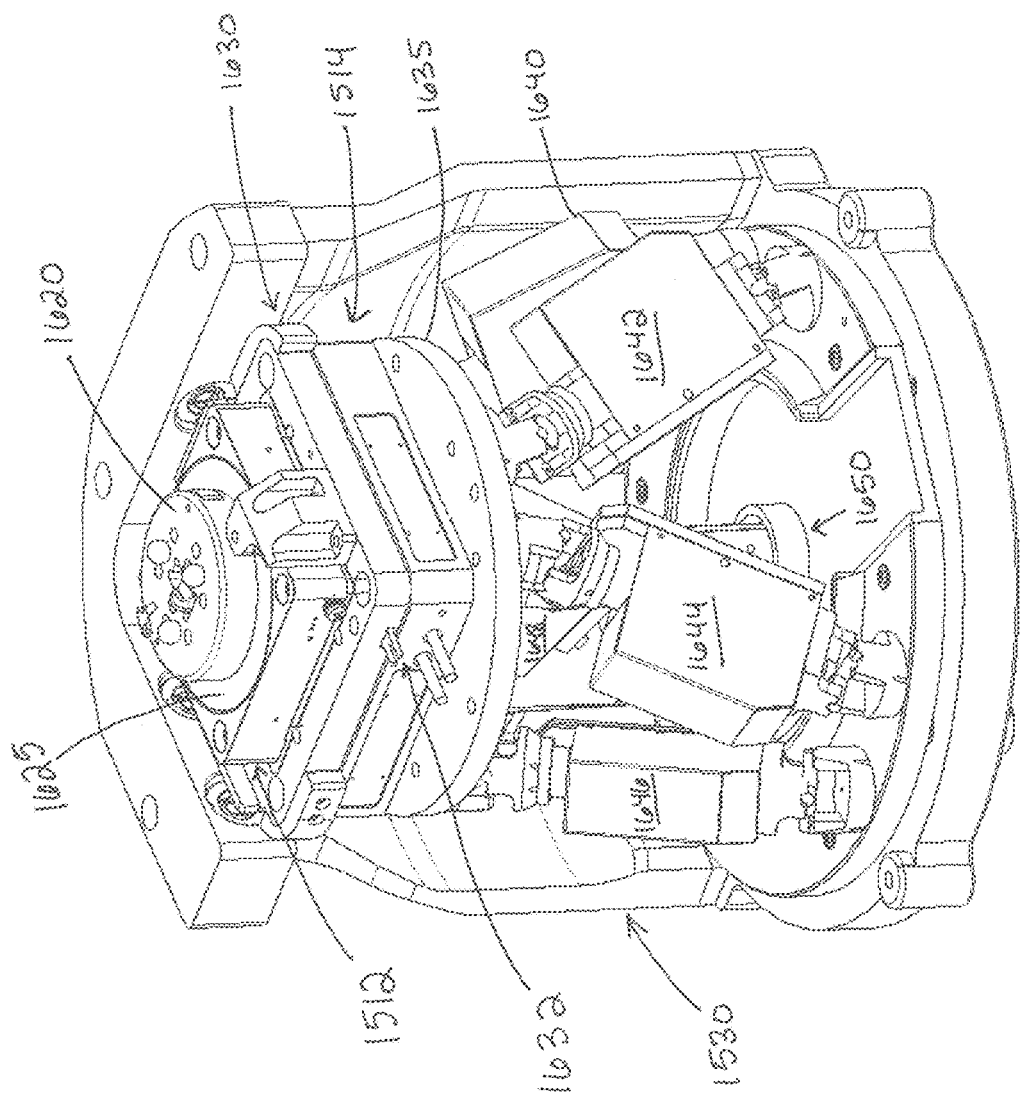
FIG. 16 is a perspective partial cut-out view of the motion system illustrating the method of mounting in the vacuum chamber, according to an embodiment of the present disclosure.
Figure 17:
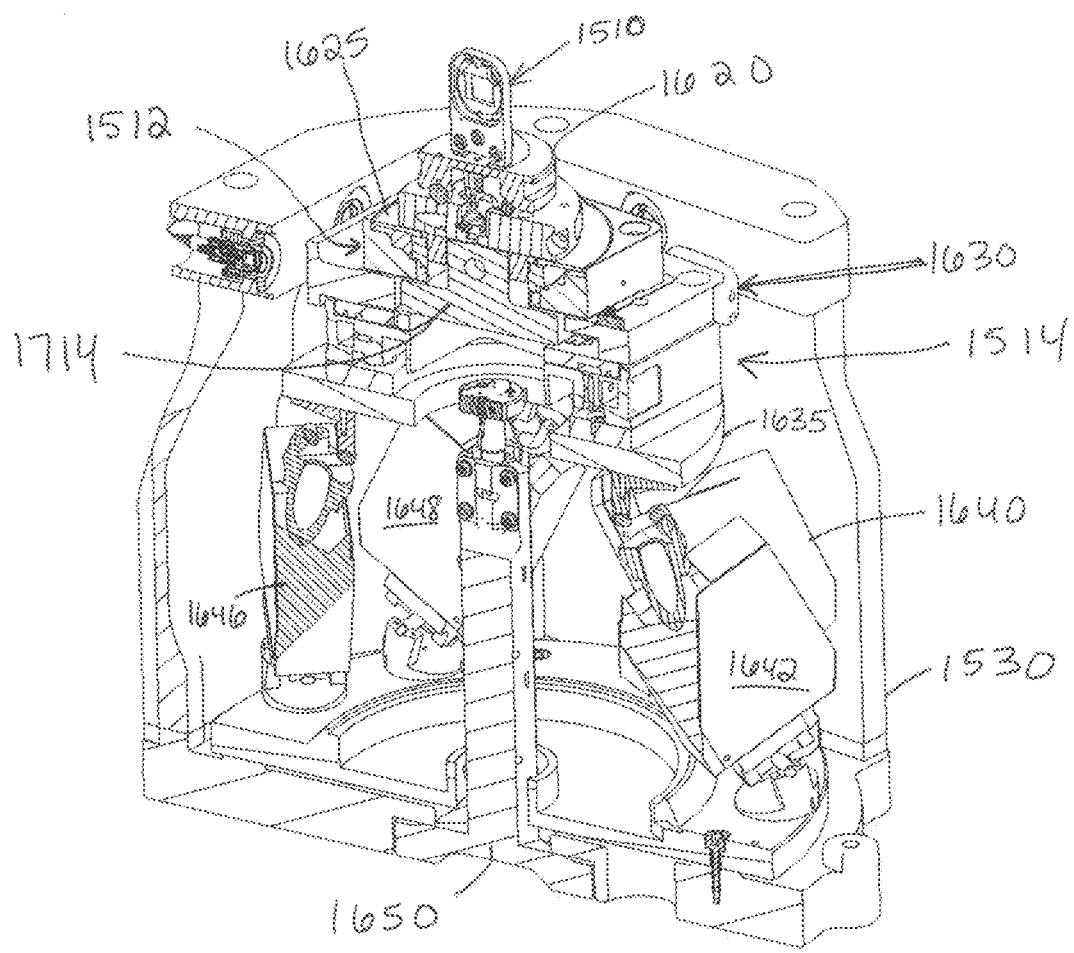
FIG. 17 is a perspective view illustrating the internal components of the motion system and various sensors, according to an embodiment of the present disclosure.
Figure 18:
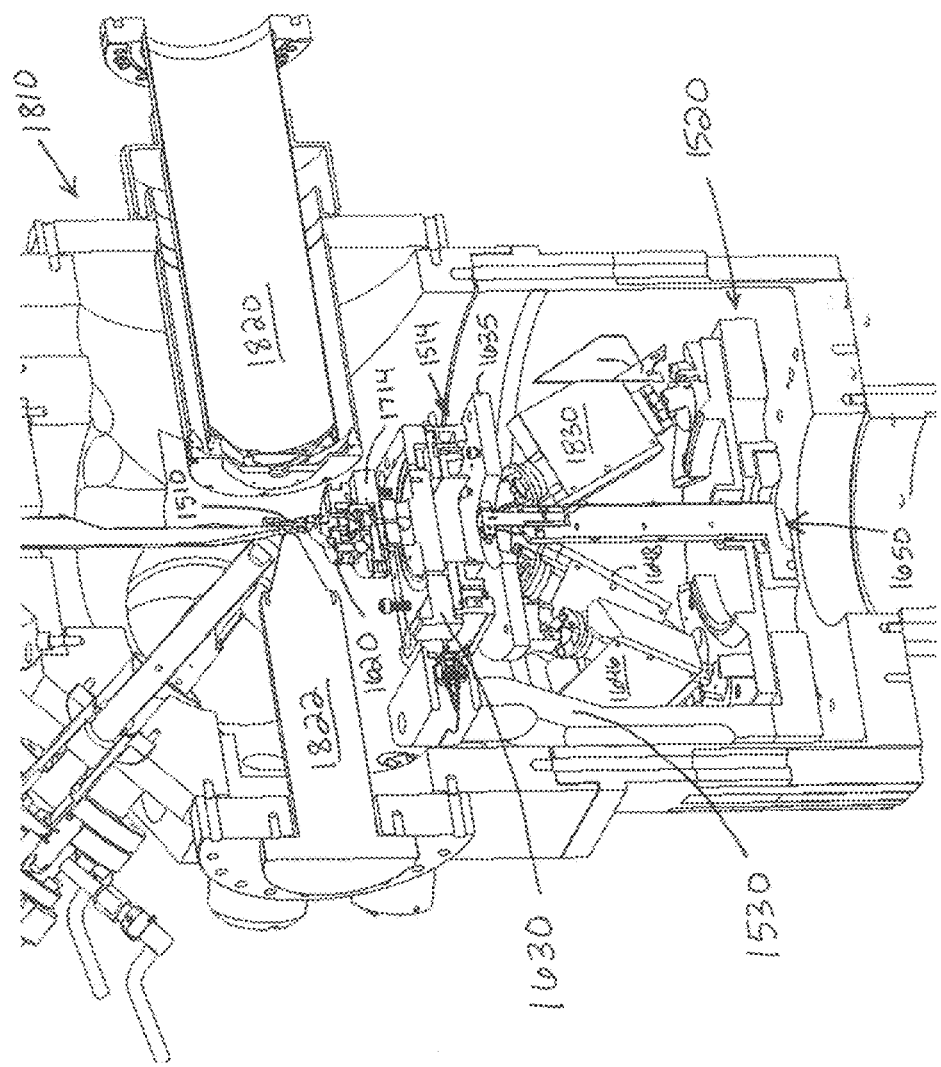
FIG. 18 is a perspective view illustrating the motion system, sample holder, and method of attachment to the motion system, according to an embodiment of the present disclosure.

The motion system 230 provides thirteen degrees-of-freedom of movement for the sample 202, as will be appreciated in light of the present disclosure. Refer, for example, to FIGS. 15-23 for details regarding the motion system. The system 200 can also include a motor 260 for the motion system 230 and a controller 270 for sending and receiving data to and from the various detectors and components within the system 200. It will be appreciated that the present disclosure provides only one example arrangement for the motion system 230, and the support for the motion system 230 is highly variable to achieve both translational movement, and also rotation, to precisely locate the sample 202 with respect to the electron beam. Further, the combined fine motion and coarse motion provides the large range of motion needed without sacrificing accuracy and repeatability. It will also be appreciated that the motors 260 may additionally or alternatively comprise actuators that control the fine motion stage of the motion system, for example as shown in FIGS. 16-18.

The electron beam generator 210 can be an electron column for a SEM, or any other appropriate device that generates a highly collimated, narrowly focused beam of electrons. The electron beam generates X-ray fluorescence, BSE, and SE directly from the sample 202 for E-mode imaging, and generates X-ray fluorescence within an engineered target for X-mode imaging. SE and BSE from the target are also produced by the electron beam during X-mode imaging and are used as feedback to stage and electron beam control. In an embodiment of the present disclosure, the electron beam generator 210 and associated detector 220 can be mounted horizontally with respect to each other. In such embodiments the optical axis of the electron beam generator 210 is coincident with the axis of the detector 220.

The electron beam should be stable to reduce positional uncertainties during measurement. A beam can drift (spatially) at a rate of up to 0.3 µm per hour. To image one sample, the electron beam generator 210 may be operational for extended periods of time. Thus, significant drift can occur during imaging of a single sample 202. As will be appreciated in light of the present disclosure, to accommodate for this drift, periodic corrections using real-time acquired metadata may be performed to ensure the system operates within the required bounds on positional uncertainties. Refer, for example, to FIGS. 26-29 showing various error correction techniques.

In some embodiments, the detector 216 and detector 220 each comprise TES detector technology, while in other embodiments one of the detector 216 and detector 220 comprises a SDD while the other comprises a TES detector assembly. In some embodiments, both detectors 216 and 220 can be SDD. It will be appreciated that each detector can comprise an array including two or more detectors in close proximity.

Although not shown in FIG. 1, the controller 270 can include a processor for performing the processing herein, and may also be coupled to additional processors for performing additional processing of the data acquired herein. The controller 270 can include multiple processors in a computer cluster, and it will be appreciated that although described as a single "processor" herein, this could include one or more processors or processing elements for carrying out the example methods herein.

In the E-mode of operation, electrons from the electron beam penetrate an IC sample 202 to various depths, and the BSE and SE are detected, respectively, by the BSE detector 212 and the SE detector 214, as will be appreciated in light of the present disclosure. Also in the E-mode of operation, detector 216 or detector 220 is used to measure X-rays that are transmitted on the same side as the electron beam generator 210.

In the X-mode of operation, fluorescent X-rays generated by the electron beam from the electron beam generator 210 on a manufactured target (not shown) are used to perform transmission absorption tomography (or spectral computed tomography), using a detector 220, as will be appreciated in light of the present disclosure. The characteristic X-rays generated in the target are generated in an isotropic production process (fluorescence), and propagate in all directions including toward the detectors 216, 220. During the X-mode of operation, the detector 220 is used to collect information about absorption properties (or atomic element densities) of the IC sample 202, and the detector 216 is used to collect metadata from the target as well as information about the target.

Prior to imaging the sample 202, the underlying silicon substrate is either nearly or completely removed. Extreme thinning of the IC sample 202 is performed to minimize electron volume scattering prior to interrogation of dopants and transistor structures. Through extreme thinning, all (or most) of the underlying substrate is removed, revealing the device layer and leaving metal contact layers intact, and allowing the beam to reach these layers with sufficient brilliance. By thinning the underlying silicon substrate, attenuation of the transmitted X-ray signal in X-mode is also reduced, which is helpful for maximizing signal-to-noise ratio (SNR) or characteristic lines in the spectral X-ray detectors and thereby reducing necessary data acquisition time. The narrow full-width, half-maximum (FWHM) of the TES detectors also improve SNR relative to conventional energy-sensitive X-ray detectors.

Figure 3:
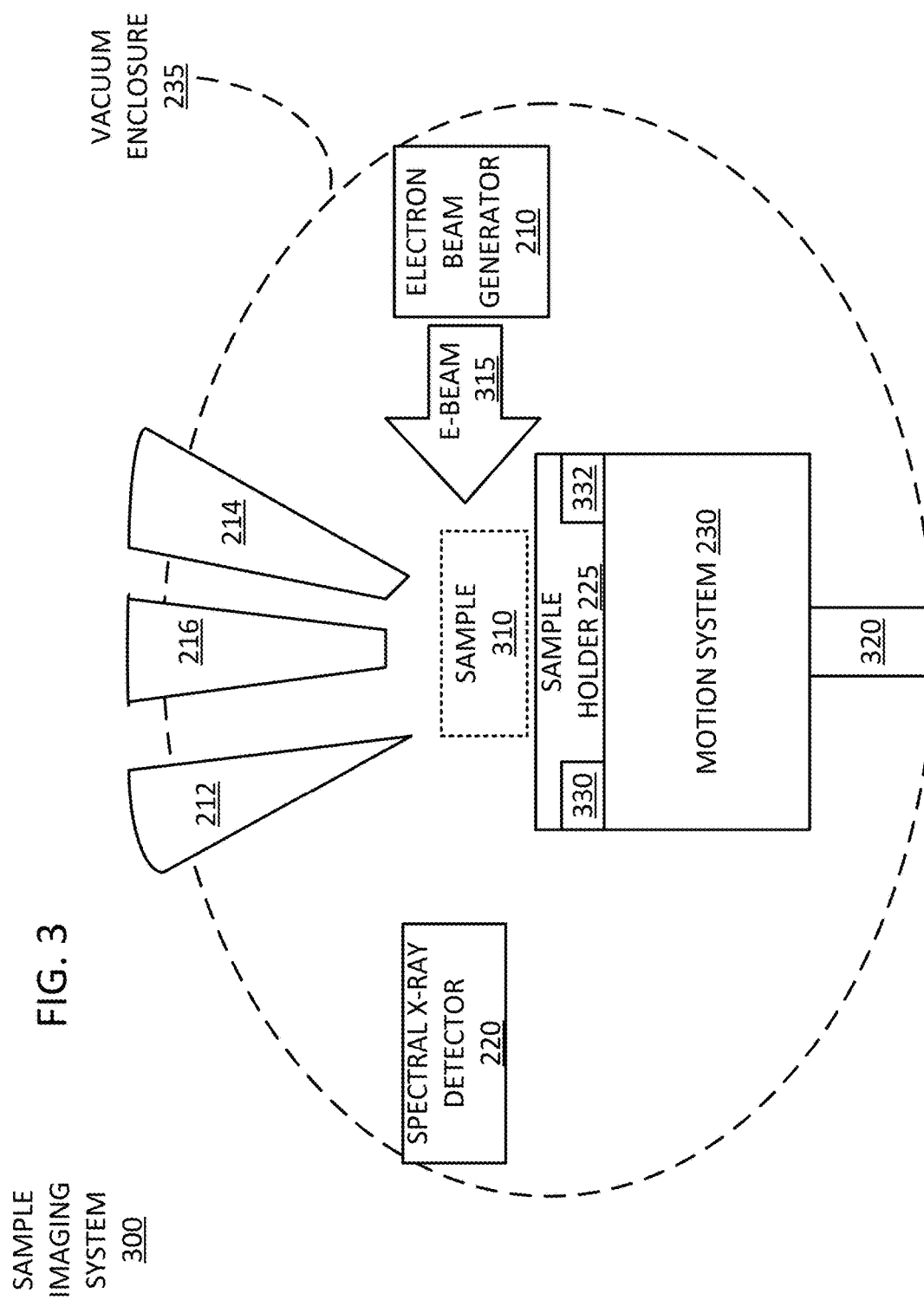
FIG. 3 is a block diagram illustrating an example system for imaging a sample, in a first mode (E-mode) of operation, in accordance with an embodiment of the present disclosure.

FIG. 3 is a block diagram illustrating an example system for imaging a sample in a first mode (E-mode) of operation, in accordance with an embodiment of the present disclosure. It will be appreciated in light of the present disclosure that the arrangement of components shown in FIG. 3 is only one possible example, and other arrangements may be implemented. As shown, the example system 300 includes the electron beam generator 210, the BSE detector 212, the SE detector 214, the detector 216, the detector 220, a sample holder 225, and a motion system 230, contained within the vacuum chamber 235, in accordance with an embodiment of the present disclosure. The electron beam generator 210 generates an electron beam 315 that produces BSE and SE originating from various depths within the IC sample 310. The system 300 can also include at least one interferometric system 320 and one or more capacitive sensors 330, 332 that account for movement of the motion system 230. The interferometric system 320 can include an interferometer tower having an optical light source and one or more reflective targets on the motion system 230 with which the interferometric system 320 determines the position of the motion system 230. A sample 310 is shown on the sample holder 225. A motor 260 (shown in FIG. 2) provides the motion system 230 the ability to move the sample 310 with respect to the electron beam 315.

Figure 26:
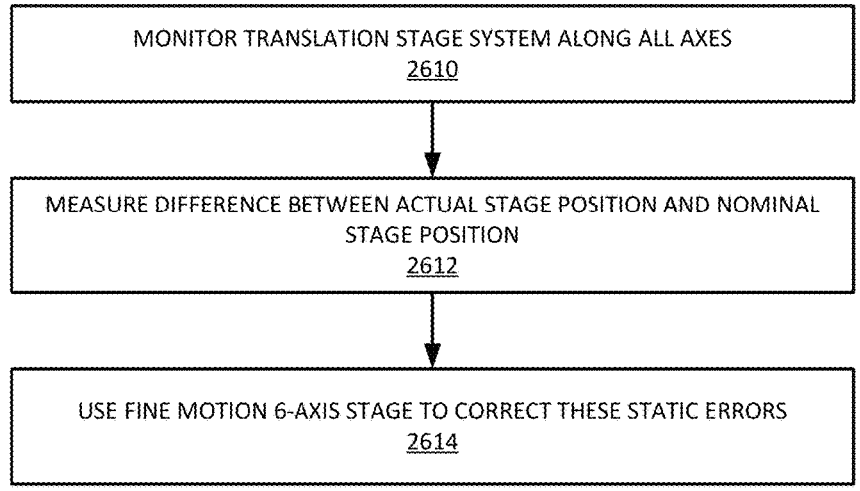
FIG. 26 is a flowchart illustrating a method for performing closed loop correction of the fine stage of the motion system, according to an embodiment of the present disclosure.

An interferometric system 320 can provide external feedback to the system 300. The aforementioned interferometer tower can include one or more optical light sources within the tower 320 that communicate with a reflective element (such as a mirror) on the motion system 230 to determine the position of the motion system 230. The measured location of the motion system 230 can be compared with the predicted position of the motion system 230. The difference between the measured location and the predicted position is another example of metadata that can be provided to the controller to determine the state of the system 300, and account for any factors affecting accurate imaging (or model-based reconstruction) of the sample 310. Refer, for example, to FIG. 26 for an example method using the interferometric sensors to correct discrepancies and errors in determining the position of the motion system 230.

During the E-mode of operation, individual fluorescent X-ray photons may be summed over all detector elements in a given detector, for example when the given detector is a TES array having multiple individual sensors. This is because the probe beam itself provides the imaging resolution, and spatial attribution of the summed X-rays derives from the beam footprint. In principle, model-based deconvolution may be performed to enhance resolution of recorded images using prior knowledge of the beam point spread function (PSF), and various statistical criteria for image restoration. The same technique can be used to restore low SNR images. A TES camera has a high spectral resolution, and the observed E-mode spectral counts can be automatically associated with a given element. The E-mode scan provides structural information about the IC front-end that potentially informs optimal data acquisition strategy during the X-mode.

The sample holder 225 is on (or can be integrated into) a motion system 230 for securely holding the sample 310 with respect to the electron beam 315 of the electron beam generator 210. The motion system 230 is for moving the sample 310 so that a particular area of the sample 310 is precisely located within the footprint of the electron beam 315 of the electron beam generator 210.

Figure 4:
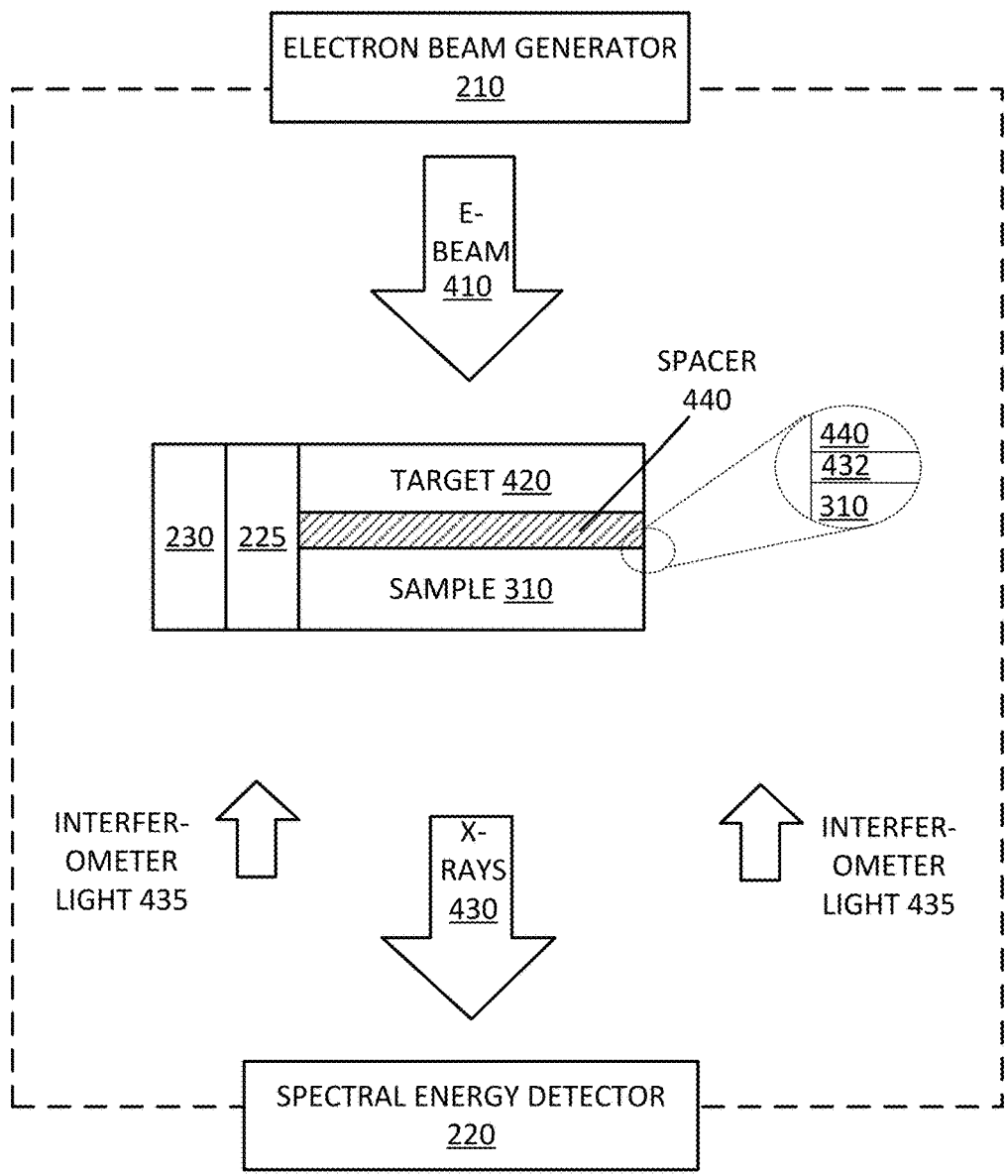
FIG. 4 is a block diagram illustrating an example system for imaging an IC sample in a second mode of operation (X-mode), in accordance with an embodiment of the present disclosure.

FIG. 4 is a block diagram illustrating an example system for imaging an IC sample 310 in a second mode (X-mode) of operation, in accordance with an embodiment of the present disclosure. During the X-mode of operation, an electron beam 410 from an electron beam generator 210 is directed toward a target 420 positioned between the sample 310 and the electron beam generator 210. The interferometric system provides position estimation of the motion system 230 and the sample holder 225 using light 435 generated by the aforementioned optical light source. Electron beam induced ionization within the target 420 yields fluorescent X-rays 430 that can be measured by both detector 220 and detector 216. During X-mode, the transmission tomography measurements are conducted on a coarser (for example 100 nm to 200 nm) grid of dwell locations, where each scan results in a large number of independent measurements across a particular detector. Alternatively, the system can operate in a "fly-scan" mode in which the sample 310 is continuously moved in a predetermined pattern with respect to the incident electron beam 410. Alternatively, a fly-scan mode can be achieved through implementation of scanning via electronic control of the electron beam, for example using small-area scanning or line scanning in combination with a "kinematic scan" by virtue of sample motion via stage control.

In some embodiments, a spacer 440 may be provided between the target 420 and the sample 310. In a "conformal" design, the target material is deposited directly onto the sample 310 and coats conformally the sample surface. The spacer 440 can be a material (such as aluminum) having a thickness of approximately 0.2 to approximately 5.0 microns. In one particular embodiment the spacer has a thickness of approximately 1.0 micron. The spacer 440 can be coated directly over the sample 310 after E-mode measurements are made and the target 420 is subsequently deposited directly onto the spacer 420. The spacer 440 is intended to have a uniform thickness, as varying thickness in the target 420 can cause errors in estimating the 3D reconstruction of the sample 310. However, in principle, the tomographic algorithms can include the target and spacer composition and geometry as a subset of the model parameter space, and whose values can be refined from presumed starting values during the course of the estimation process. The spacer layer helps dissipate heat generated by the electron beam, conducts away charge accumulation, helps absorb electrons (as a barrier to entry into the IC sample 310), provides mechanical stability for the target/sample assembly, and provides favorable geometry for 3D X-ray reconstruction.

In some embodiments, the spacer 440 may be a finite micro-gap between the target 420 and the sample 310. Such an embodiment can be considered a "nested" design, where the target 420 and the sample 310 are physically separate units. The E-mode measurements are performed with the target 420 removed, and the X-mode measurements are performed with the target 420 in place. This option allows for multiple target types as they are not bonded to the sample 310. This embodiment provides flexibility for multiresolution processing and for optimizing data acquisition plans. One drawback is that both the target 420 and the sample 310 can warp over time (on the order of micrometers) and reconstruction requires tracking the thickness of the target 420, adding a further technical complication. It can also be difficult to estimate the separation distance between the target 420 and the sample 310 in the nested design. However, these issues can be addressed with model-based estimation techniques.

In still other embodiments, as shown in the dotted line break-out in FIG. 4, the sample 310 and spacer 440 may have a release layer 432 located between them. This can be referred to as a "flexible membrane" design. In this approach, the target 420 is coated on a thin, compliant membrane. The membrane is held in contact with the sample 310 via the release layer 432. The membrane serves to dissipate and spread heat, and thus this design has the virtue of the sample 310 and target 440 being more removable or separable relative to the conformal design.

Methodology—Imaging

Figure 5:
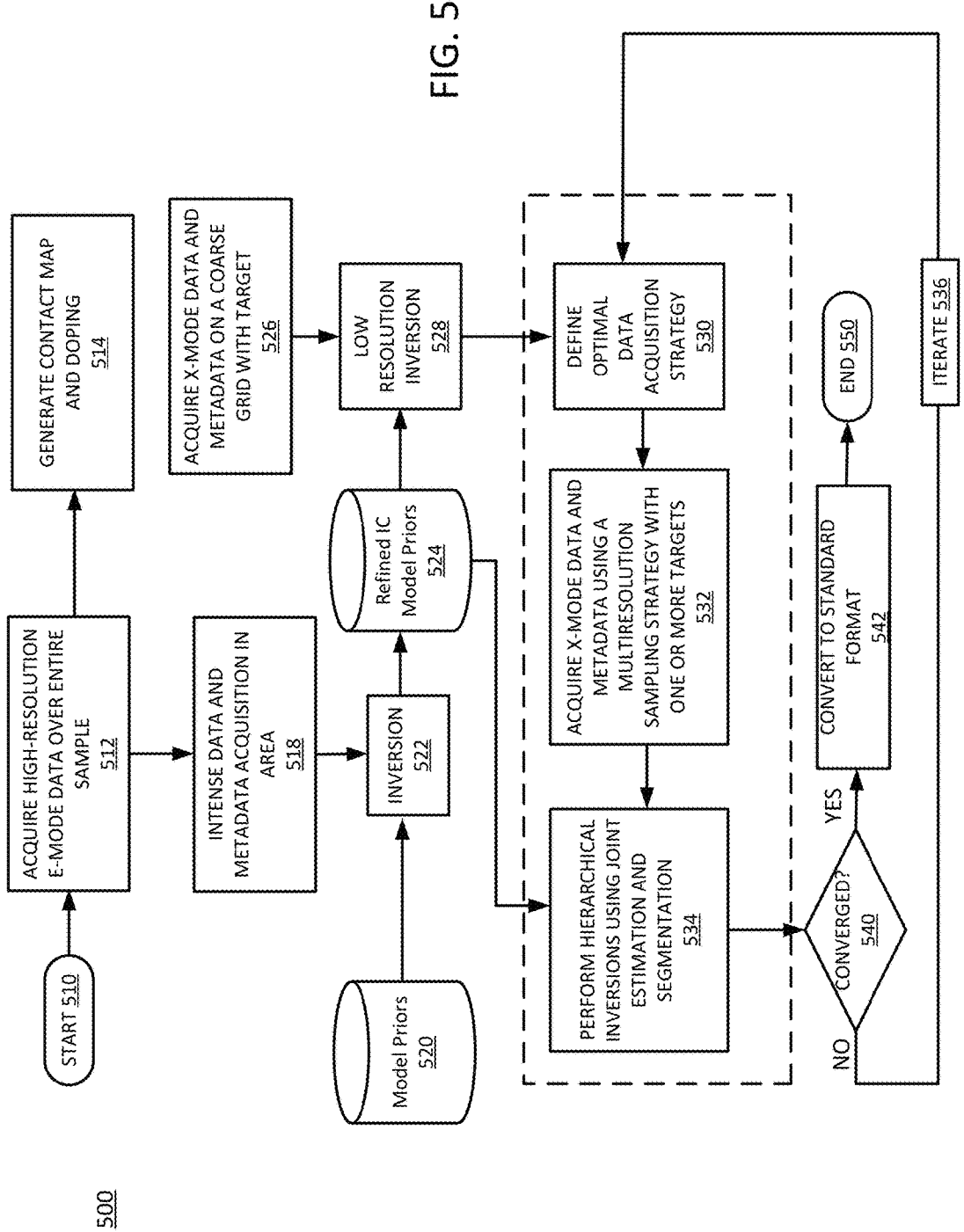
FIG. 5 is a flowchart illustrating an example hierarchical processing method for imaging a sample, according to an embodiment of the present disclosure.
Figure 6:
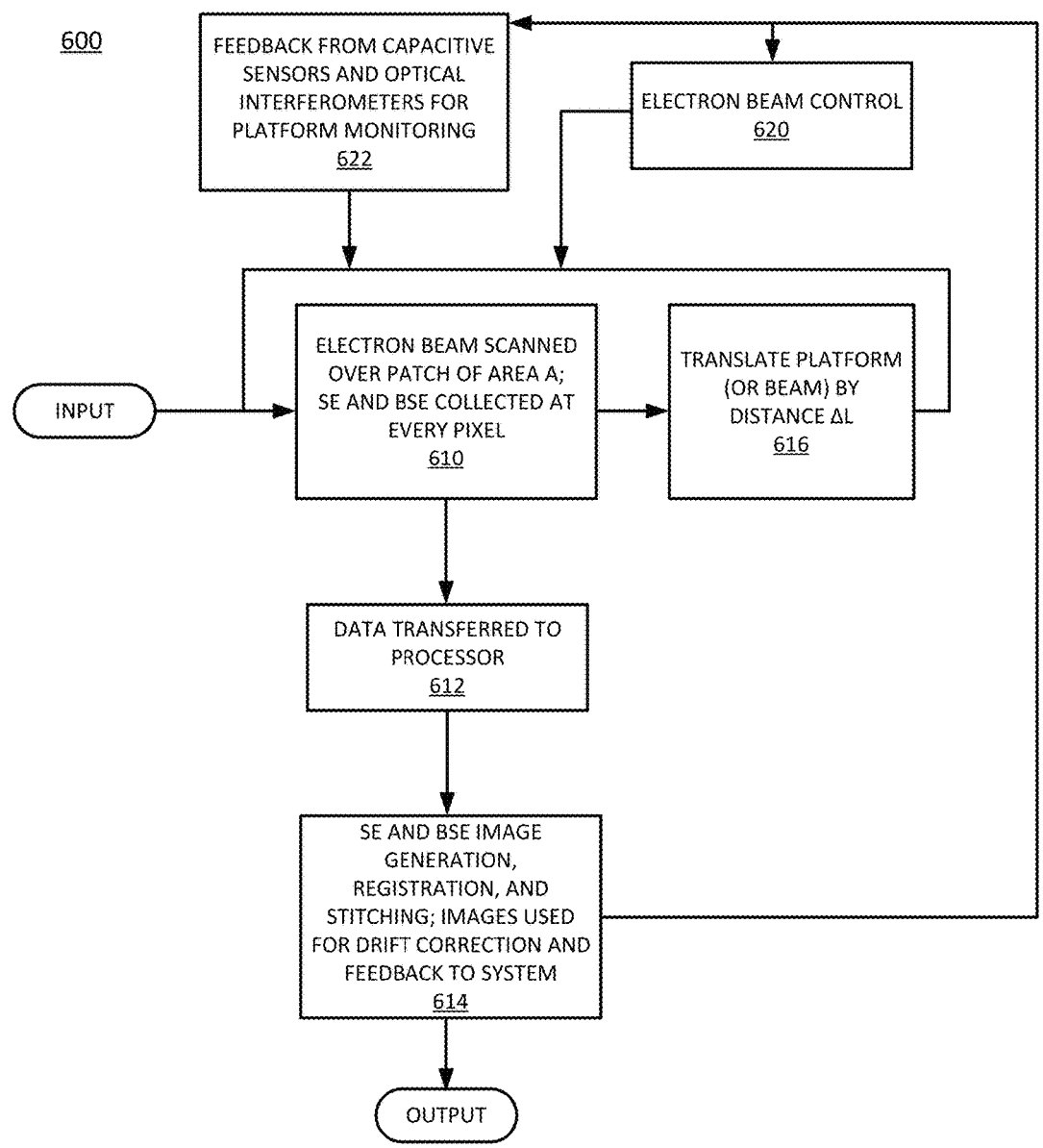
FIG. 6 is a flowchart illustrating an example method for acquiring high resolution data during a first mode of operation, according to an embodiment of the present disclosure.

It will be appreciated in light of the present disclosure that the systems disclosed herein can implement one or more of the following example methods to achieve high resolution imaging of a sample having a complex structure, such as an IC. FIG. 5 is a flowchart illustrating one example method, and FIGS. 6-16 each provide additional details for one or more of the elements of FIG. 5, as will be appreciated in light of the present disclosure. For example, FIG. 6 provides one example method that corresponds to element 512 in FIG. 5.

FIG. 5 is a flowchart illustrating an example hierarchical processing method 500 for imaging a sample, according to an embodiment of the present disclosure. The method 500 is initiated to start at 510. At 512, high resolution data is acquired during the E-mode. In certain embodiments, this corresponds to a data resolution between 5 nm and 80 nm, a data resolution between 7 nm and 60 nm, or a data resolution between 10 nm and 50 nm. In one particular implementation, this corresponds to data at a resolution of 10 nm. More generally, this resolution should correspond to the size of the smallest features (e.g., transistors) of the sample, so that they can be resolved. This can occur over the entire area of the sample. FIG. 6 illustrates one example method of acquiring high resolution data during the E-mode of operation, in accordance with an embodiment of the present disclosure. The BSE data, SE data, and backward propagating X-ray data are collected during E-mode. The high resolution data acquired in E-mode provides information that helps drive optimal data acquisition strategies during the X-mode of operation, as will be appreciated in light of the present disclosure.

Figure 7:
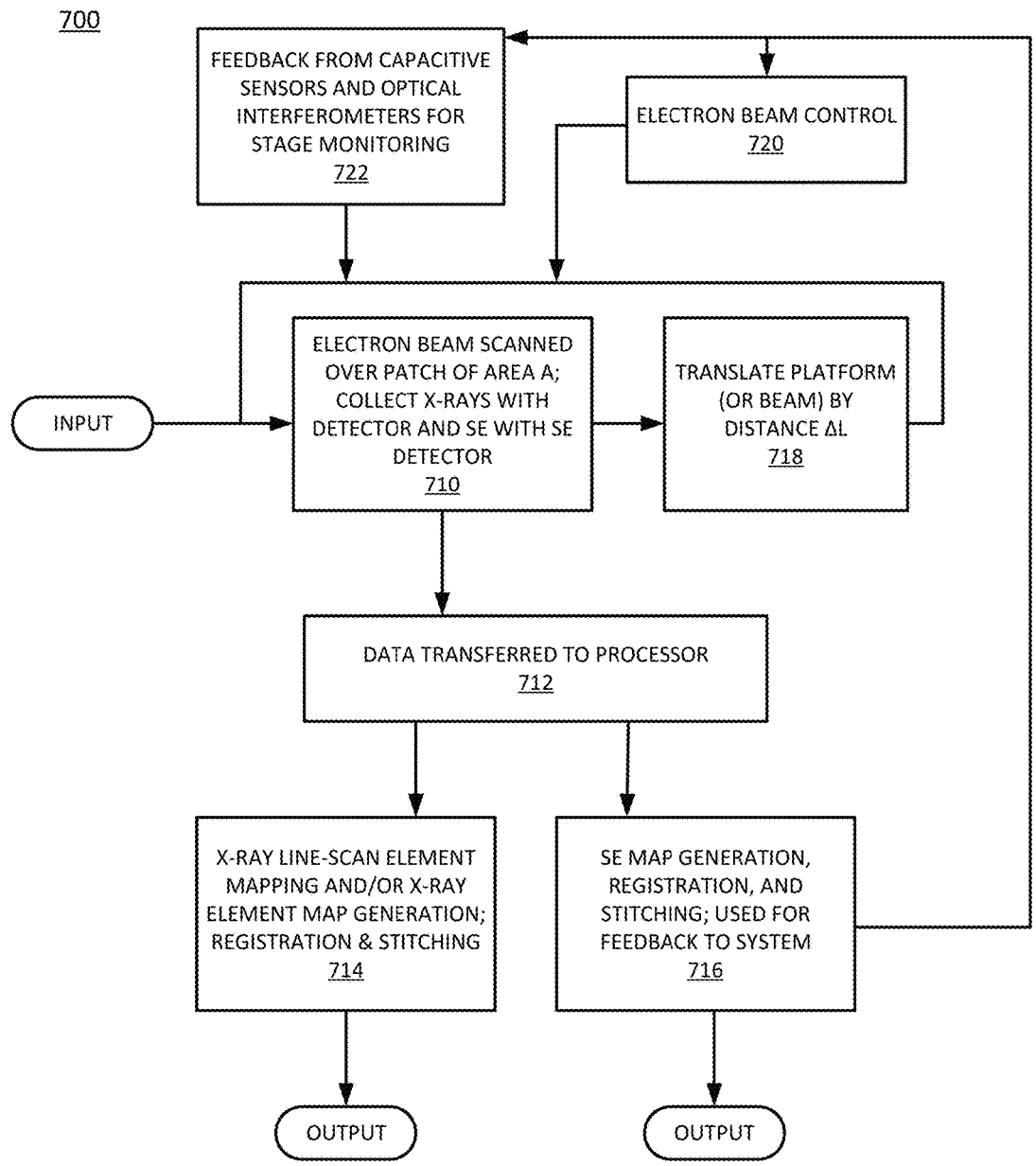
FIG. 7 is a flowchart illustrating an example method for determining resolution contact map and doping from data acquired during the first mode of operation, according to an embodiment of the present disclosure.

At 514, a contact map and doping is generated to a predetermined resolution commensurate with the sample under test. In certain embodiments, this corresponds to a resolution between 5 nm and 80 nm, a resolution between 7 nm and 60 nm, or a resolution between 10 nm and 50 nm. In one particular implementation the contact map and doping are generated to a resolution of 10 nm. More generally, this resolution should correspond to the size of the smallest features of the sample, so that they can be resolved. The chemical maps are generated by collecting backward propagating fluorescent X-rays produced from the IC front-end, and the SE maps are used for feedback to the motion system and the electron beam controller. FIG. 7 illustrates one example method of generating the contact map and doping, in accordance with an embodiment of the present disclosure.

Figure 8:
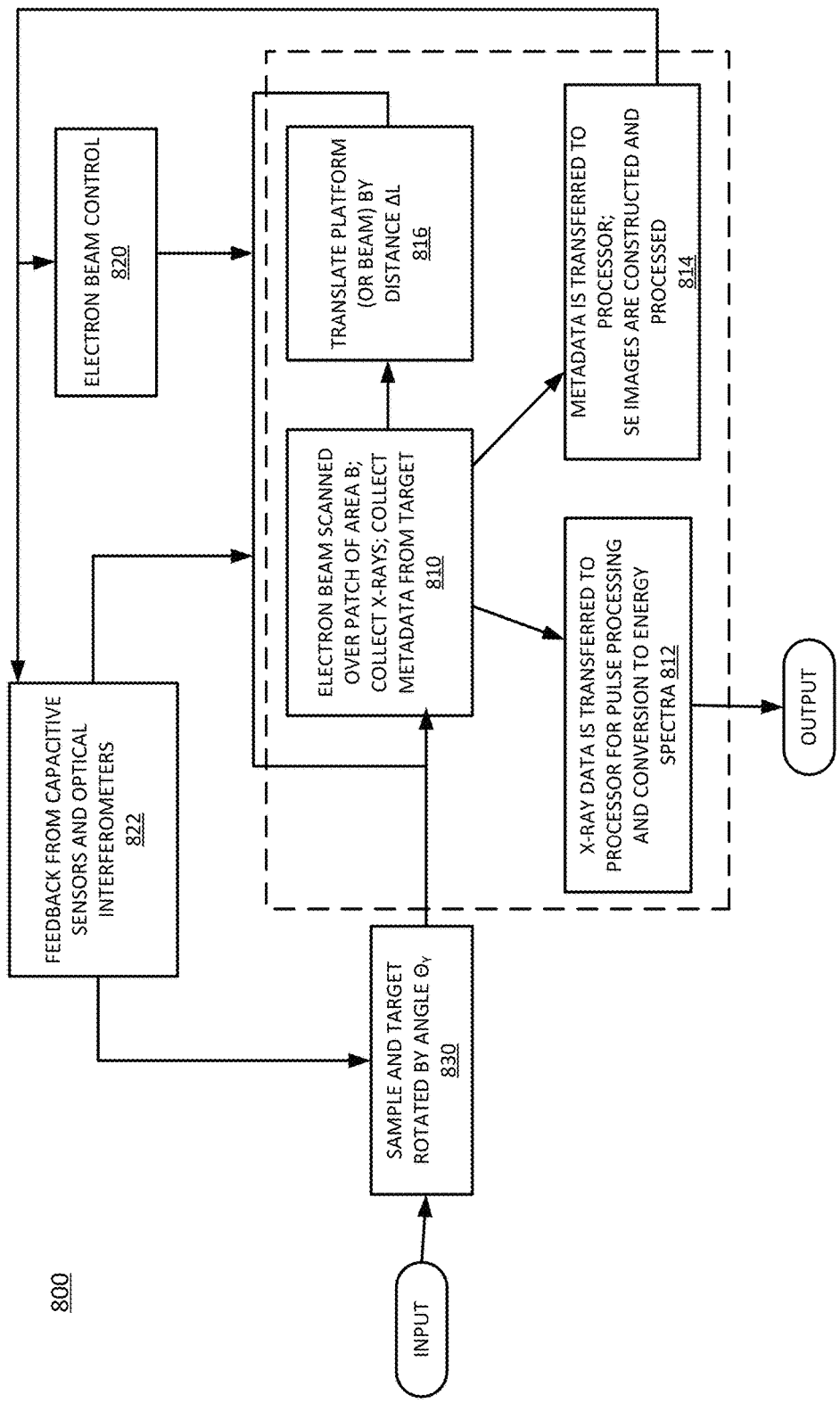
FIG. 8 is a flowchart illustrating an example method for intense data and metadata acquisition in a small and selected area in the second mode of operation, according to an embodiment of the present disclosure.

At 518, intense data and metadata acquisition occurs in the selected area. In one particular implementation, the selected area is 40 μm×40 μm. The intense data and metadata acquisition can use, for example, model priors 520 stored in a database local or external to the imaging system. More generally, the intense data acquisition of the small area (characterized by high-density spatial sampling with the probe beam), use of high-density angular sampling for the case of X-ray tomography, and long dwell-time for the purpose of increasing SNR, can be used to estimate priors for use in estimation of the rest of the IC, and which will be estimated using "less intense" data acquisition. The priors may include the number of layers, typical pitch values for each layer, characteristic dimensions in each layer, chemical compositions present in each layer, and other characteristics as well. FIG. 8 illustrates one example method for intense data and metadata acquisition in the selected area, in accordance with an embodiment of the present disclosure. The model priors 520 are determined from E-mode data collection.

Figure 9:
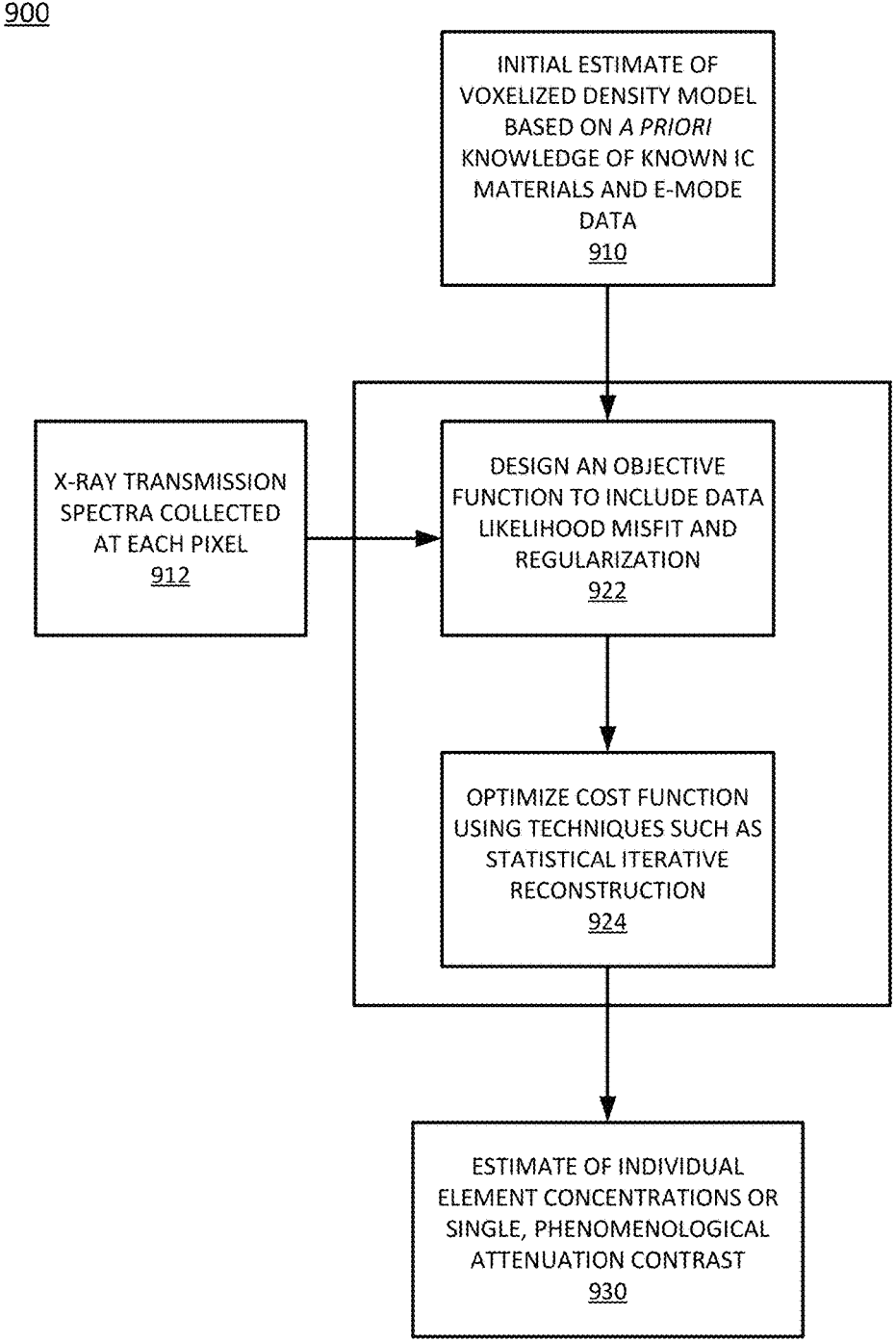
FIG. 9 is a flowchart illustrating an example method for inversion of the data and metadata acquired for the selected area, according to an embodiment of the present disclosure.

At 522, inversion occurs on the data and metadata acquired during both E-mode and X-mode, thus resulting in refined IC model priors 524. FIG. 9 illustrates an example method for inversion, in accordance with an embodiment of the present disclosure. At 526, data and metadata are acquired in X-mode, in accordance with an embodiment of the present disclosure. The data and metadata at 526 are acquired on a coarse grid with, for example, a 200 nm target to achieve high SNR. FIG. 8 illustrates an example method for acquiring the X-mode data and metadata on a coarse grid, in accordance with an embodiment of the present disclosure. Note that 526 and 522 can occur simultaneously, or sequentially one after the other, depending upon the particular application and/or processing capabilities of the controller. The acquired metadata can be filtered to smooth the outputs using any suitable filtering techniques.

Figure 10:
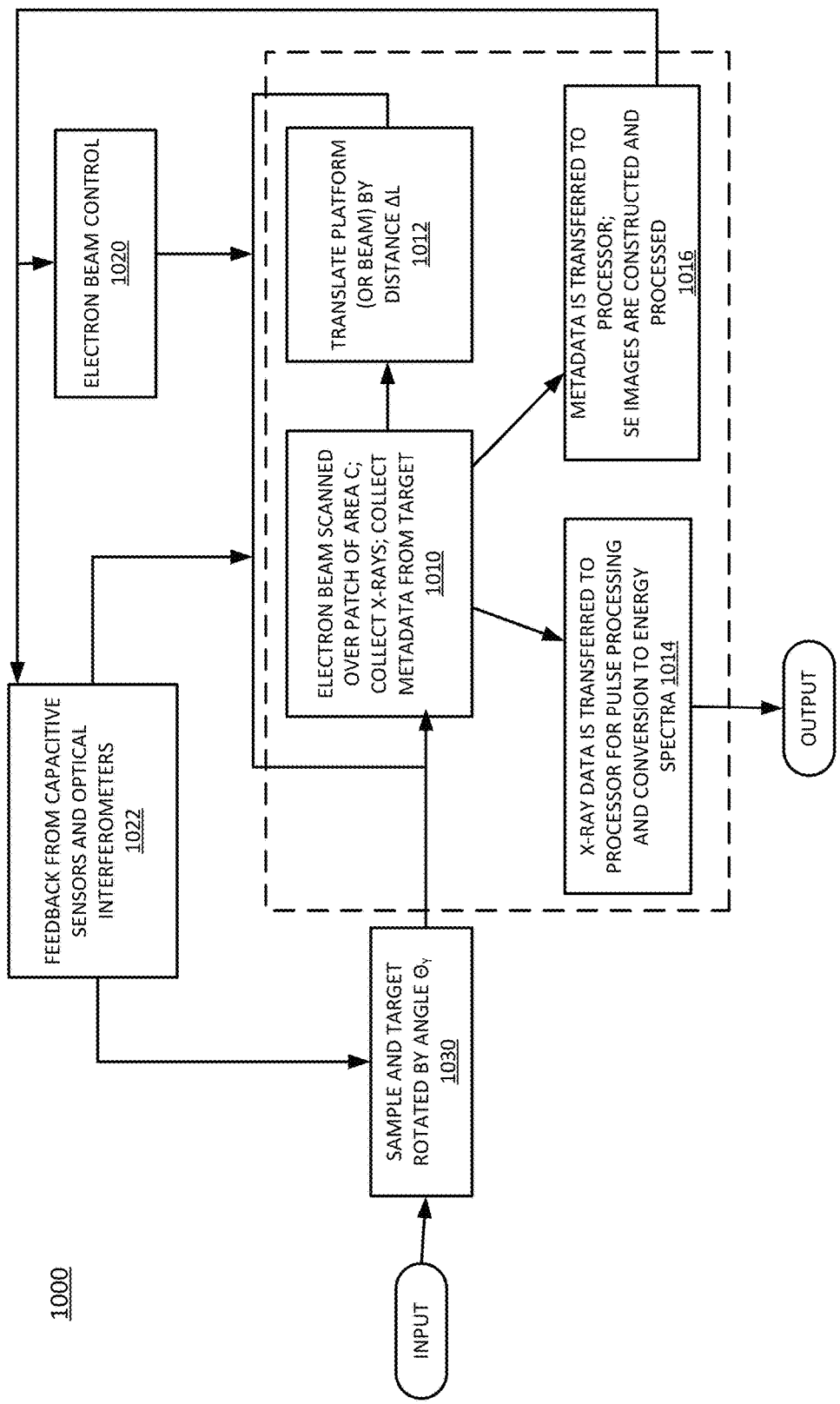
FIG. 10 is a flowchart illustrating an example method for acquiring data and metadata on coarse grid in the second mode of operation, according to an embodiment of the present disclosure.
Figure 11:
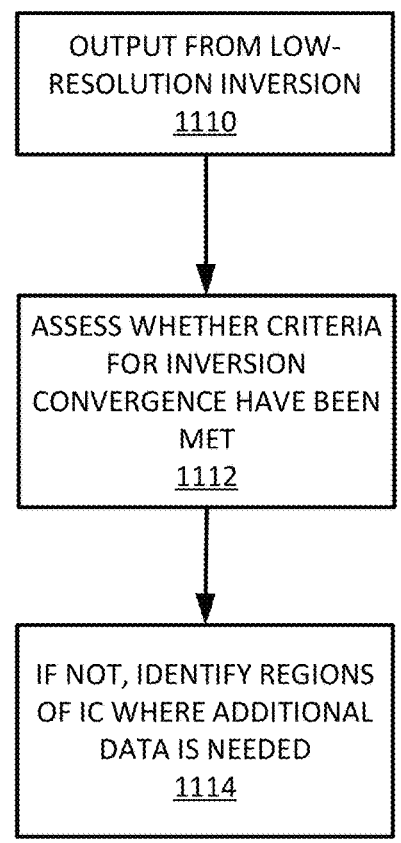
FIG. 11 is a flowchart illustrating an example method for defining optimal data acquisition, according to an embodiment of the present disclosure.
Figure 12:
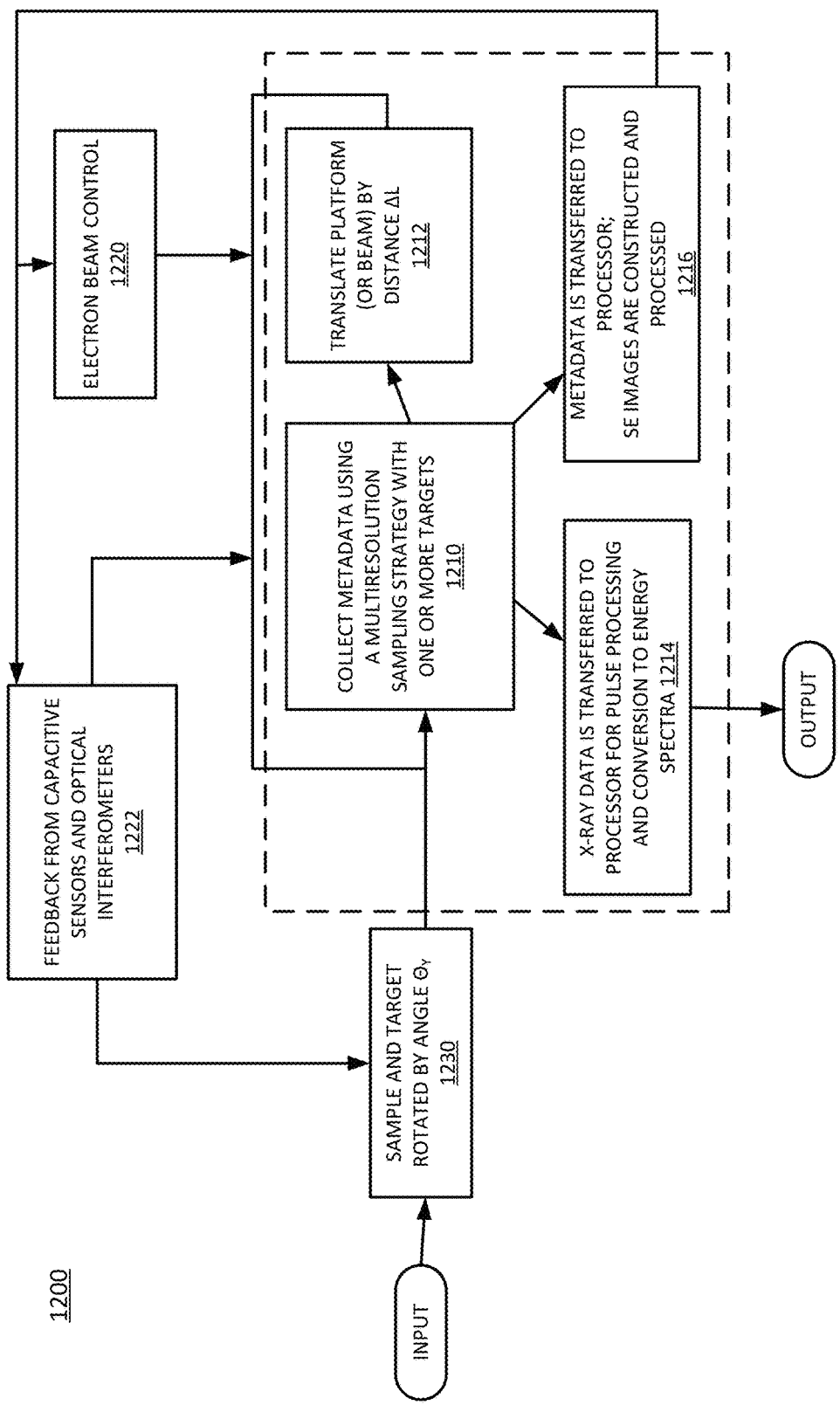
FIG. 12 is a flowchart illustrating an example method for acquiring data and metadata using a multiresolution sampling strategy with one or more targets during the second mode of operation, according to an embodiment of the present disclosure.
Figure 13:
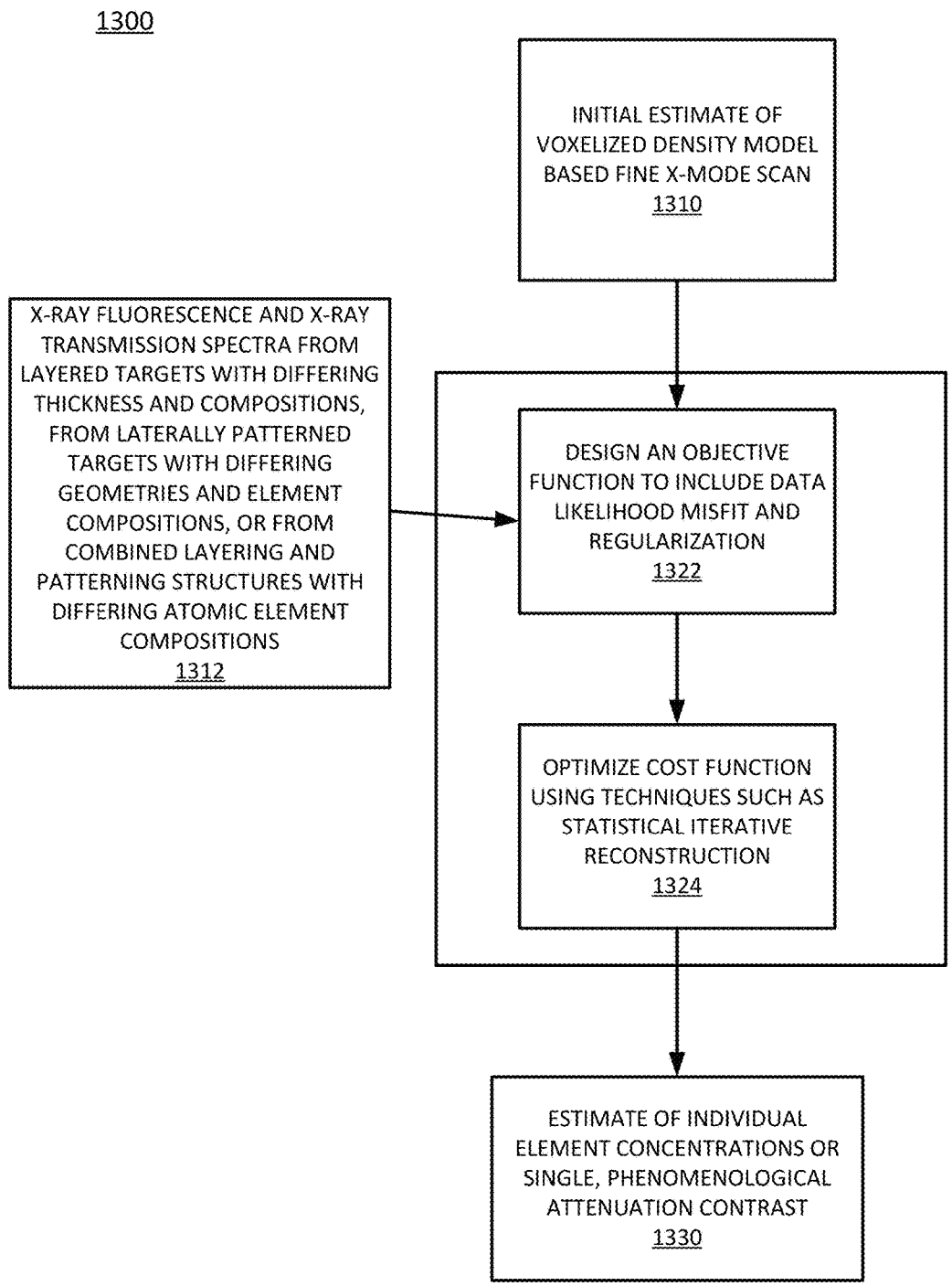
FIG. 13 is a flowchart illustrating an example method for performing multi-scale, hierarchical inversions on the data and metadata, including joint estimation and segmentation, according to an embodiment of the present disclosure.
Figure 14:
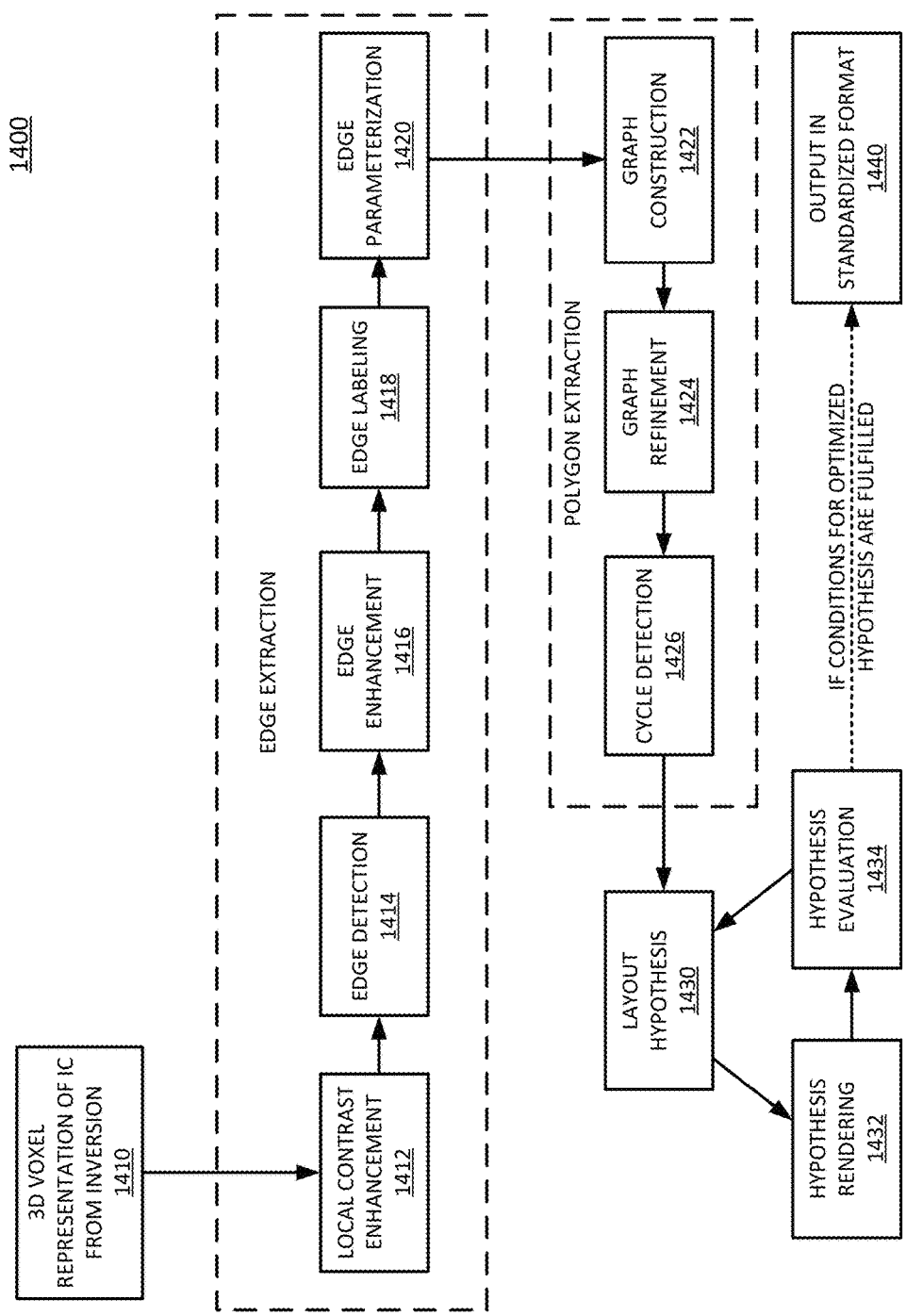
FIG. 14 is a flowchart illustrating an example method for converting to a GDSII format, according to an embodiment of the present disclosure.

At 528, low resolution inversion is performed, in accordance with an embodiment of the present disclosure. FIG. 10 illustrates an example method for performing the low resolution inversion. The low resolution inversion uses X-ray transmission spectra collected from the coarse scan and an initial estimate based on the fine scan. The low resolution inversion at 528 performs a coarse scan of the entire sample to get a sense of the large features and the overall structure. The example method 500 then iterates the data at 536, for example by performing 530, 532, and 534, to determine if the data has converged at 540. At 530, the optimal data acquisition strategy is defined. The output from the low resolution inversion (at 528) is assessed to determine if inversion convergence has been met. FIG. 11 illustrates an example method for defining the optimal data acquisition strategy. At 532, data and metadata are acquired in X-mode using a multiresolution sampling strategy with one or more targets. At 532, data and metadata can be acquired using single or multiple targets. Data is acquired from the detector (for example detector 112 or detector 120) collecting X-rays and the metadata from the target itself is collected by another detector. FIG. 12 illustrates an example method for acquiring data and metadata in X-mode, in accordance with an embodiment of the present disclosure. At 534, multi-scale, hierarchical inversions are performed, in accordance with an embodiment of the present disclosure. These multi-scale inversions may include joint estimation and segmentation. An estimation of element concentration in a 3D voxelized IC model is produced. Inversions may be performed using, for example, statistical iterative reconstruction, using model-based iterative reconstruction (MBIR), or via nonlinear programming methods such interior point optimization. The latter is particularly useful for incorporating constraints and bounds such as model parameter positivity. FIG. 13 illustrates an example method for performing the multi-scale inversion. The inversions at 534 are performed at a higher resolution (as compared to the low resolution inversion at 528) to identify smaller features by analyzing a smaller area of the sample at a time. At 536, the optimal acquisition strategy 530, the acquisition of X-mode data and metadata 532, and the hierarchical inversion 534 are iterated until, at 540, the data is converged. If the data is converged, at 542 the 3D representation from the IC inversion is converted to a standardized format, such as GDSII, which may use binary or ASCII for the data. The GDSII format is a standardized format for describing an IC sample, and provides one possible format. FIG. 14 illustrates an example method for converting the data into a GDSII format. The example method 500 then ends at 550.

FIG. 6 is a flowchart illustrating an example method 600 for acquiring high resolution data during a first mode of operation, according to an embodiment of the present disclosure. The example method 600 corresponds to element 512 in FIG. 5, where high resolution data is acquired in E-mode over the entire sample. At 610, the electron beam is scanned over an area A, which is a particular area of the sample selected for imaging. SE and BSE are collected at every scan point, as will be appreciated in light of the present disclosure. It will be appreciated that either BSE or SE can be detected at different detectors, or both BSE and SE can be detected by the same detector. At 612, the data is transferred to the processor, and at 614 the SE and BSE images are generated, registered, and stitched together with images from previous scan areas. These images are also used for drift correction and feedback to the motion system and to the electron beam controller. Once a scan of the electron beam is complete, at 616 the motion system moves the sample by a predetermined vector position increment ΔL to scan a new area of the sample. The distance ΔL refers to the distance from the center of one area of interest to another, and thus after completion of scanning an area of interest, the beam is moved by the distance ΔL to a new area of interest and scanning begins again. This continues until the entire IC sample has been imaged during the E-mode of operation.

The images generated by the processor at 614 are also used for drift correction and feedback to the motion system and to the electron beam. The images can be used to more accurately determine electron beam control at 620. Specifically, an image is collected, and a timestamp is also collected for that location of the electron beam. The motion system can be translated a small distance and a new image is acquired. There is a predetermined overlap between sequential images, thus the drift of the electron beam can be detected using a custom machine vision recognition technique. The images can also be combined with data from the capacitive sensors and optical interferometers as feedback to the motion system at 622.

FIG. 7 is a flowchart illustrating an example method 700 for determining a high-resolution contact map and doping from data acquired during the first mode of operation, according to an embodiment of the present disclosure. At 710, the electron beam is scanned over an area of interest of the sample having an area A. In this mode, fluorescent X-rays are collected with a detector array, and SE are detected with a SE detector. At 712, the X-ray data and SE data are transferred to the processor. At 714, the X-ray data is used to generate, register, and stitch together an X-ray elemental map. At 716, the SE data is used to generate, register, and stitch together a SE map. At 716, the SE data is also used for feedback to the stage and electron beam. The SE data is provided for electron beam control at 720 and monitoring the motion system at 722. Data from the feedback sensors (for example capacitive sensors and optical interferometric sensors) are also provided to monitor the motion system at 722. Once a scan of the electron beam is complete, at 718 the motion system (or the electron beam itself) is translated or otherwise moved by a predetermined distance ΔL to scan a new area of the sample. This continues until the entire IC sample has been imaged during the E-mode of operation.

FIG. 8 is a flowchart illustrating an example method 800 for intense "fine" data and metadata acquisition in the selected area during the X-mode of operation, according to an embodiment of the present disclosure. At 810, the sample is scanned via stage translation over an area of interest of the sample having a particular area B. The area B would generally be the same as area A in FIG. 7. The area can vary depending on the feature size being imaged. The areas of interest of the sample being imaged are expected to overlap to provide imaging of the sample. The transmitted X-rays are collected with a detector array, such as a TES camera, at 810. And metadata from the target is collected with another detector, such as a spectral energy detector. At 812, the data is transferred to the processor for pulse processing and conversion to energy spectra. At 814, the metadata is transferred to the processor. Also at 814, SE images of the target are constructed and processed for the purposes of electron beam focusing, alignment, astigmatism correction, and stage monitoring, in accordance with an embodiment of the present disclosure. Metadata in the form of X-rays collected from the exposed surface of the target can be used to invert for density modeling of the target that can be later exploited for normalization purposes.

Once a scan of the electron beam is complete, at 816 the motion system (or the electron beam itself) is translated or otherwise moved by a predetermined distance ΔL to scan a new area of the sample. This continues until the entire IC sample has been imaged during the X-mode of operation. At 820, the feedback is provided for electron beam control. The feedback is also provided from capacitive sensors and optical interferometers at 822. The sample and the target are then rotated by an angle at 830. The sample is then scanned over a new area of interest of an area B at 810. This continues until the entire sample is imaged.

FIG. 9 is a flowchart illustrating an example method 900 for inversion of the data and metadata acquired for the selected area, according to an embodiment of the present disclosure. At 910, an initial estimate of a voxelized attenuation or element density model based on a priori knowledge of known IC materials and the E-mode data is performed, in accordance with an embodiment of the present data. At 912, X-ray transmission spectra are collected at each pixel of a detector array. At 922, an objective function is designed to include data likelihood misfit and regularization. At 924, a cost function is optimized using any of various reconstruction techniques. At 930, individual element concentrations or single, phenomenological attenuation contrast is estimated.

FIG. 10 is a flowchart illustrating an example method 1000 for acquiring data and metadata on a coarse grid in the X-mode of operation, according to an embodiment of the present disclosure. At 1010, the sample is scanned via translation of the motion system over an area of interest of the sample having a particular area C. The transmitted X-rays are collected by a detector at 1010, and metadata from the target is collected with another spectral energy detector and an electron detector. At 1014, the data is transferred to the processor for pulse processing and conversion to energy spectra. At 1016, the metadata is transferred to the processor, and SE images are constructed and processed for the purposes of electron beam focusing, alignment, astigmatism correction, motion system monitoring, and electron beam control. Once a scan of the electron beam is complete, at 1012 the motion system (or the electron beam itself) is translated or otherwise moved by a predetermined distance ΔL to scan a new area of the sample. This continues until the entire IC sample has been imaged during the X-mode of operation. At 1020, the feedback from the metadata is provided for electron beam control. At 1022, feedback is also provided from capacitive sensors and optical interferometers. The sample and target are then rotated by an angle at 1030. The sample is then scanned over a new area of interest of an area C at 1010. This continues until the entire sample is imaged.

FIG. 11 is a flowchart illustrating an example method 1100 for defining optical X-ray data acquisition, according to an embodiment of the present disclosure. At 1110, output from the low-resolution inversion is received. At 1112, the processor assesses whether criteria for inversion convergence have been met. If, at 1114, the convergence has not been met, regions of the IC sample are identified where additional data is needed.

FIG. 12 is a flowchart illustrating an example method 1200 for acquiring data and metadata using a multiresolution sampling strategy in the X-mode of operation, according to an embodiment of the present disclosure. At 1210, the sample is scanned via translation of the motion system over an area of interest of the sample having a particular area B. Also at 1210, the transmitted X-rays are collected by a detector, and metadata is collected with another spectral energy detector and a SE detector. Single or multiple targets can be imaged. For example, a relatively thin target can be imaged, removed from the chamber, be subjected to a deposition operation to increase the target thickness, and then be imaged a second time. At 1214, the data is transferred to the processor for pulse processing and conversion to energy spectra. At 1216, the metadata is transferred to the processor, and SE images are constructed and processed for the purposes of electron beam focusing, alignment, astigmatism correction, motion system monitoring, and electron beam control. Once a scan of the electron beam is complete, at 1212 the motion system (or the electron beam itself) is translated or otherwise moved by a predetermined distance ΔL to scan a new area of the sample. This continues until the entire IC sample has been imaged during the X-mode of operation. At 1220, the feedback from the metadata is provided for electron beam control. At 1222, feedback is also provided from capacitive sensors and optical interferometers. The sample and target are then rotated over a sequence of angles at 1230. The target can be a single target that is subjected to sequential deposition and imaging operations, or can a single, multi-layer target of unique elemental composition. The sample is then scanned over a new area of interest Ni of an area B at 1210. This continues until the entire sample is imaged.

FIG. 13 is a flowchart illustrating an example method 1300 for performing multi-scale, hierarchical inversions on the data and metadata acquired for the selected area, including joint estimation and segmentation, according to an embodiment of the present disclosure. At 1310, an initial estimate of a voxelized density model based on a fine X-mode scan is performed. At 1312, X-ray fluorescence and X-ray transmission spectra are collected at each pixel. The X-ray fluorescence and X-ray transmission spectra can be from layered targets with differing thickness and compositions, from laterally patterned targets with differing geometries and element compositions, or from combined layering and patterning structures with different atomic element compositions. At 1322, an objective function is designated to include data likelihood misfit and regularization. At 1324, a cost function is optimized using statistical iterative reconstruction techniques, nonlinear programming techniques, or others. At 1330, individual element concentrations or single, phenomenological attenuation contrast is estimated. Thus, multi-scale inversion is achieved by the example method 1300.

FIG. 14 is a flowchart illustrating an example method 1400 for converting to a GDSII format, according to an embodiment of the present disclosure. It will be appreciated that this is one example method for converting the 3D voxel representation of the IC from the inversion, along with all of the other acquired data and metadata, to generate a standardized format output, such as GDSII. The output in binary format can be used, for example, to compare to the output of the system to the intended structure for the IC, as well as to ensure that the output and the intended output match.

At 1410, the 3D voxel representation of the IC sample from inversion is received. First an edge extraction is performed, including 1412, 1414, 1416, 1418, and 1420. Then a polygon extraction is performed, including 1422, 1424, and 1426. At 1412, a local contrast enhancement is performed. At 1414, an edge detection is performed. At 1416, an edge enhancement is performed. At 1418, an edge labeling is performed, and at 1420, an edge parameterization is performed for each 3D voxel representation of the IC from the inversion.

At 1422, a graph construction is performed. At 1424, a graph refinement is performed. At 1426, a cycle detection is performed. A layout hypothesis is determined at 1430. A hypothesis rendering 1432 and hypothesis evaluation 1434 are iteratively carried out until conditions for an optimized hypothesis are fulfilled. At 1440, the output in binary format is generated.

It will be appreciated in light of the present disclosure that, although described with respect to an IC structure, the system and methods are likewise applicable to other areas of imaging, including but not limited to energy conversion and storage, catalysis, nanoelectronics, earth sciences, environmental sciences, planetary sciences, and life sciences (e.g., brain tissue). For example, in a battery design, there is significant interest in nano-architectured electromechanical structures with high surface to bulk ratio, because these have the potential to significantly improve the performance of existing lithium-ion cells (e.g., higher energy and power densities, faster charging, etc.).

In certain embodiments the imaging techniques disclosed herein can be used to detect counterfeit ICs, inauthentic ICs, or other ICs that do not conform to a trusted standard. Counterfeit or otherwise fake ICs are an increasingly serious problem, particularly when the counterfeit or otherwise fake IC performs at a substandard level in a critical application. Thus, in certain implementations after imaging is complete the binary output can be compared to a binary output corresponding to a trusted standard. Where a counterfeit generated by virtue of a superficial modification, such as by relabeling parts via painting, it may be possible to detect a counterfeit via two-dimensional imaging, thus rendering it unnecessary to generate a complete 3D reconstruction of the sample in question. On the other hand, in some cases a 3D reconstruction may be used to detect more subtle alterations that are introduced into a sample via counterfeiting. Such alternations may not be visible via two-dimensional imaging, but may nevertheless impact overall circuit operation. For example, if a counterfeiter uses a less robust lithography process that produces a nominally equivalent IC, this could result in earlier than expected circuit failures. In some cases discrepancies resulting from less robust lithography can be detected using 3D imaging since certain IC features will be too thin, misshapen, or have some other anomalous appearance that would indicate that a different manufacturing technique had been used. Imaging techniques that provide 10 nm resolution, such as certain of the techniques disclosed herein, can be used to provide sufficiently high-resolution 3D imaging to detect such anomalous structures.

It will also be appreciated that the preceding are example methods, which may be modified, changed, or otherwise revised in accordance with the present disclosure, and also other methods can be implemented by the systems herein. Likewise, the example methods may be implemented by any appropriate system for imaging a sample that is within the scope of the present disclosure.

Motion System Architecture

Figure 15:
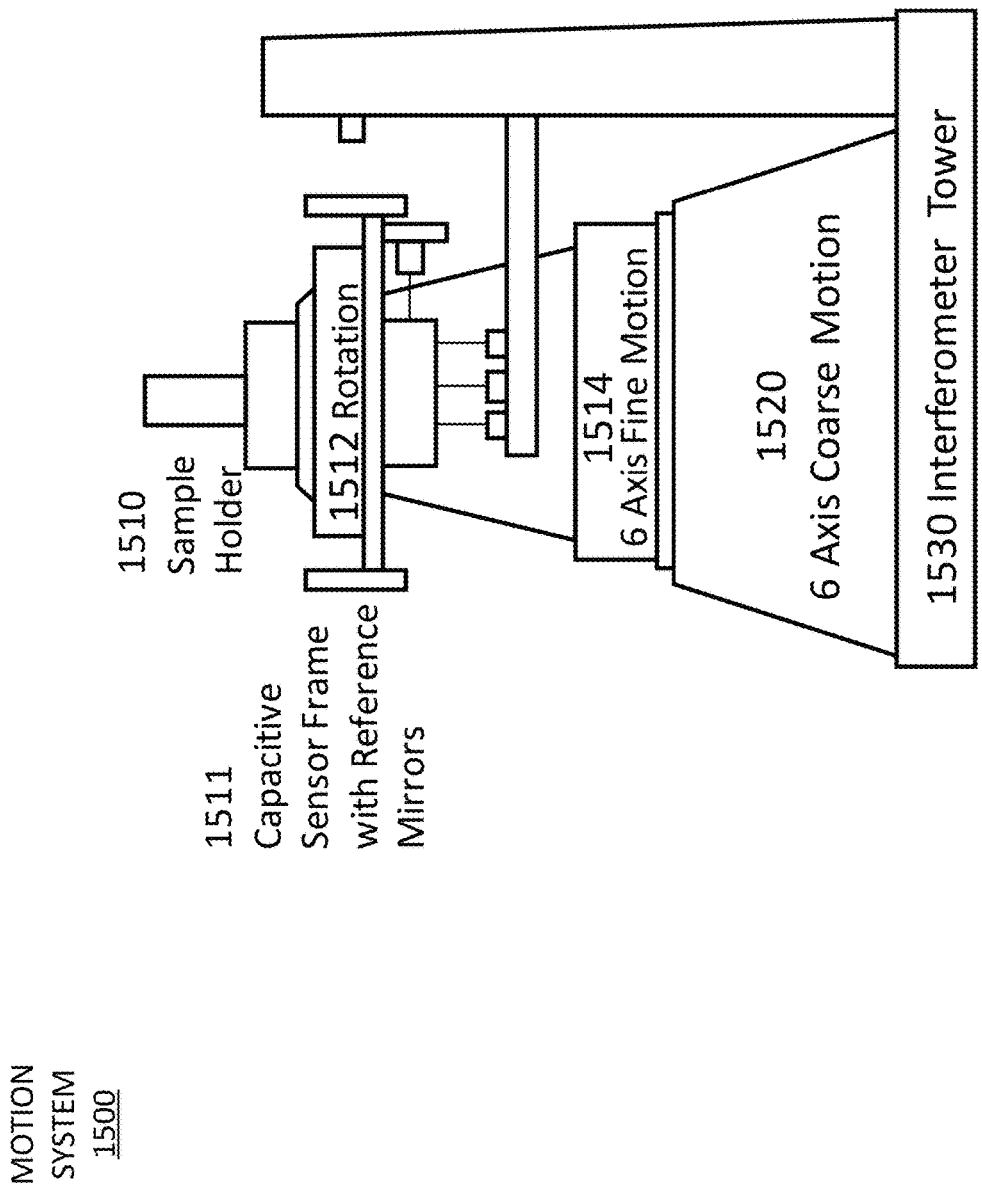
FIG. 15 is a block diagram illustrating a motion system, according to an embodiment of the present disclosure.

FIG. 15 is a schematic block diagram illustrating a motion system 1500 according to an embodiment of the present disclosure. The motion system 1500 includes a sample holder 1510, a rotation stage 1512, a mirrored reference frame 1511, a fine motion 6-axis stage 1514, and a coarse motion 6-axis hexapod 1520. Each of the coarse axes has encoder position feedback; the rotation stage axes have encoder feedback; and each of the fine motion axes have capacitive sensor feedback. Each of the thirteen axes uses its intrinsic feedback device to be driven in closed loop control. The motion system 1500 further includes a metering structure, herein referred to as the interferometer tower 1530, having three distance sensors in a horizontal plane proximate a top portion of the interferometer tower 1530 as well as three distance sensors directed vertically up along the center axis of the motion system 1500. As will be appreciated in light of the present disclosure, the motion system 1500 provides for thirteen degrees-of-freedom for highly accurate placement of the sample with respect to an electron beam generator (not shown in FIG. 15). For example, in certain embodiments the closed loop real time control techniques disclosed herein achieve between 1 nm and 20 nm accuracy depending upon the features of the sample under test. Then the vision recognition software enhances stage accuracy to between 0.5 nm and 10 nm, again depending upon the features of the sample under test.

Figure 19:
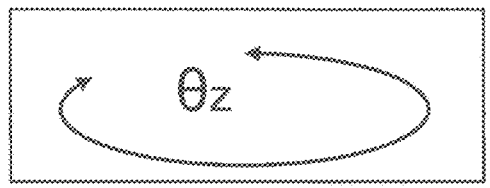
FIGS. 19-21 are graphical diagrams illustrating the various degrees-of-freedom afforded by the motion system, according to an embodiment of the present disclosure.
Figure 20:
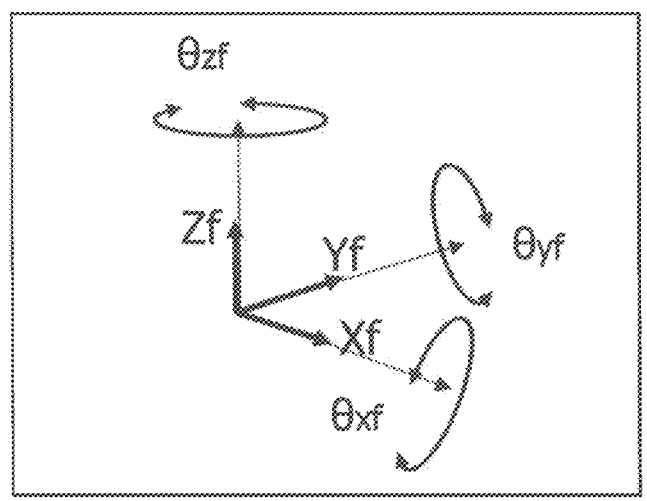
Figure 21:
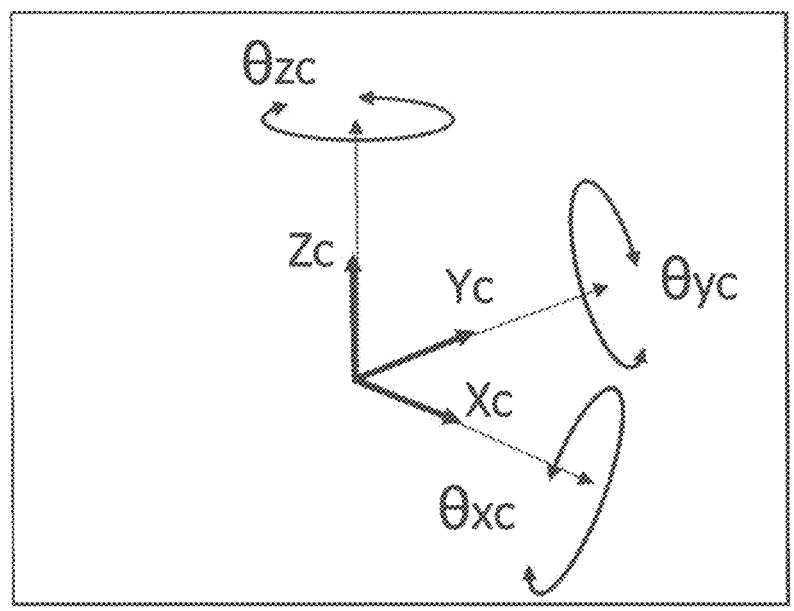

The rotation stage 1512 can provide a first degree-of-freedom for the motion system 1500. Refer, for example, to FIG. 19 for a graphical diagram illustrating the degree-of-freedom afforded by the rotation stage 1512. The fine motion 6-axis stage 1514 provides a second, third, fourth, fifth, sixth, and seventh degree-of-freedom for the motion system 1500. Refer, for example, to FIG. 20 for a graphical diagram illustrating the six degrees-of-freedom afforded by the fine motion 6-axis stage 1514. The second degree-of-freedom can be the X-axis of movement, the third degree-of-freedom can be the Y-axis of movement, the fourth degree-of-freedom can be the Z-axis of movement, the fifth degree-of-freedom can be rotation along the X-axis of movement, the sixth degree-of-freedom can be rotation along the Y-axis of movement, and the seventh degree-of-freedom can be rotation along the Z-axis of movement of the fine motion 6-axis stage 1514, thereby providing six additional degrees-of-freedom for the motion system 1500. The coarse motion 6-axis hexapod 1520 provides an eighth, ninth, tenth, eleventh, twelfth, and thirteenth degree-of-freedom for the motion system 1500. Refer, for example, to FIG. 21 for a graphical diagram illustrating the six degrees-of-freedom afforded by the coarse motion 6-axis hexapod 1520. The eighth degree-of-freedom can be the X-axis of movement, the ninth degree-of-freedom can be the Y-axis of movement, the tenth degree-of-freedom can be the Z-axis of movement, the eleventh degree-of-freedom can be rotation along the X-axis of coarse movement, the twelfth degree-of-freedom can be rotation along the Y-axis of coarse movement, and the thirteenth degree-of-freedom can be rotation along the Z-axis of coarse movement. Accordingly, the motion system 1500 provides for thirteen total degrees-of-freedom to provide for accurate placement of the sample with respect to the electron beam generator.

Figure 22:
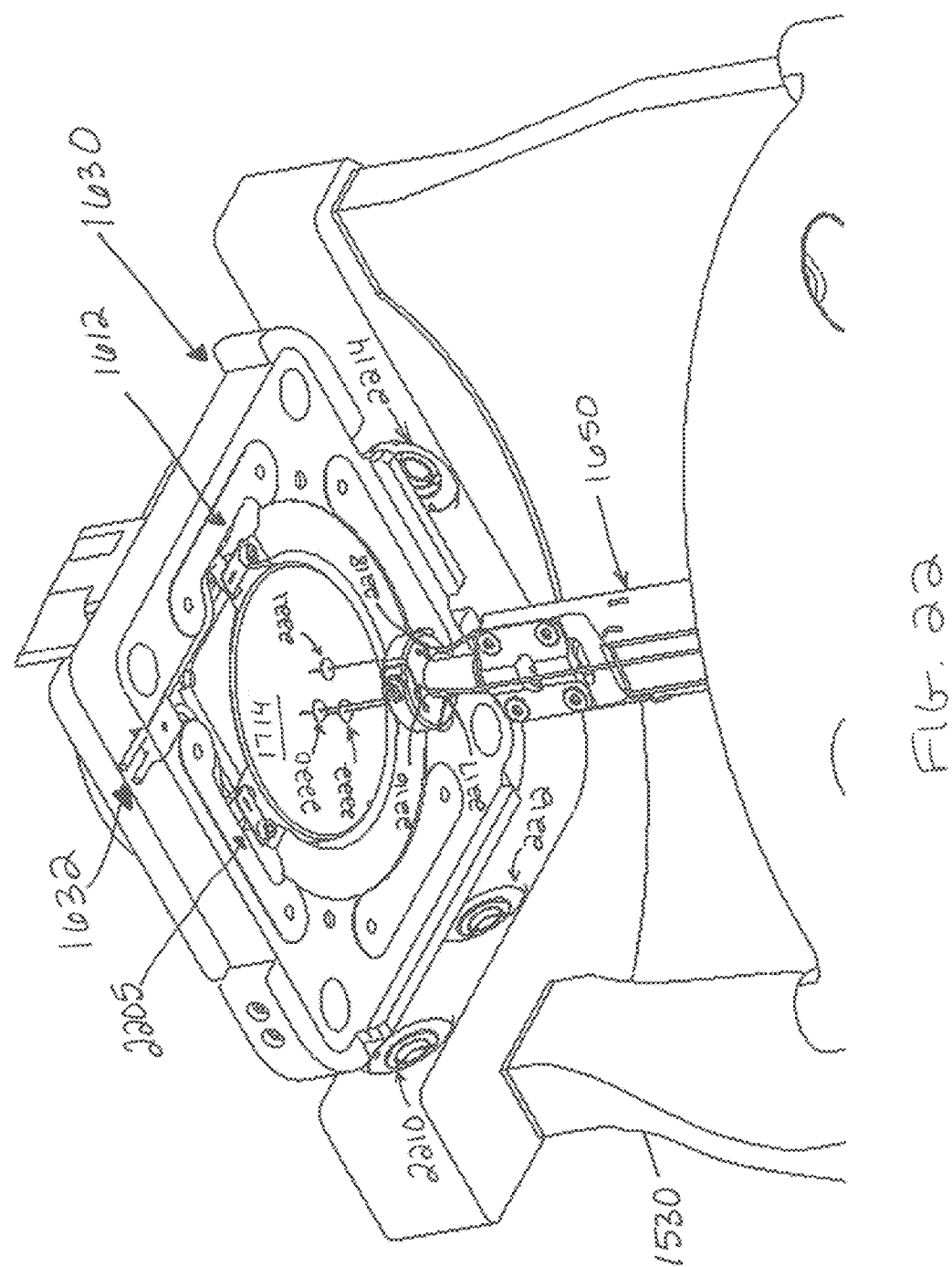
FIG. 22 is a perspective view illustrating a bottom surface of the capacitive sensor housing and the reference cylinder of the motion system, according to an embodiment of the present disclosure.
Figure 23:
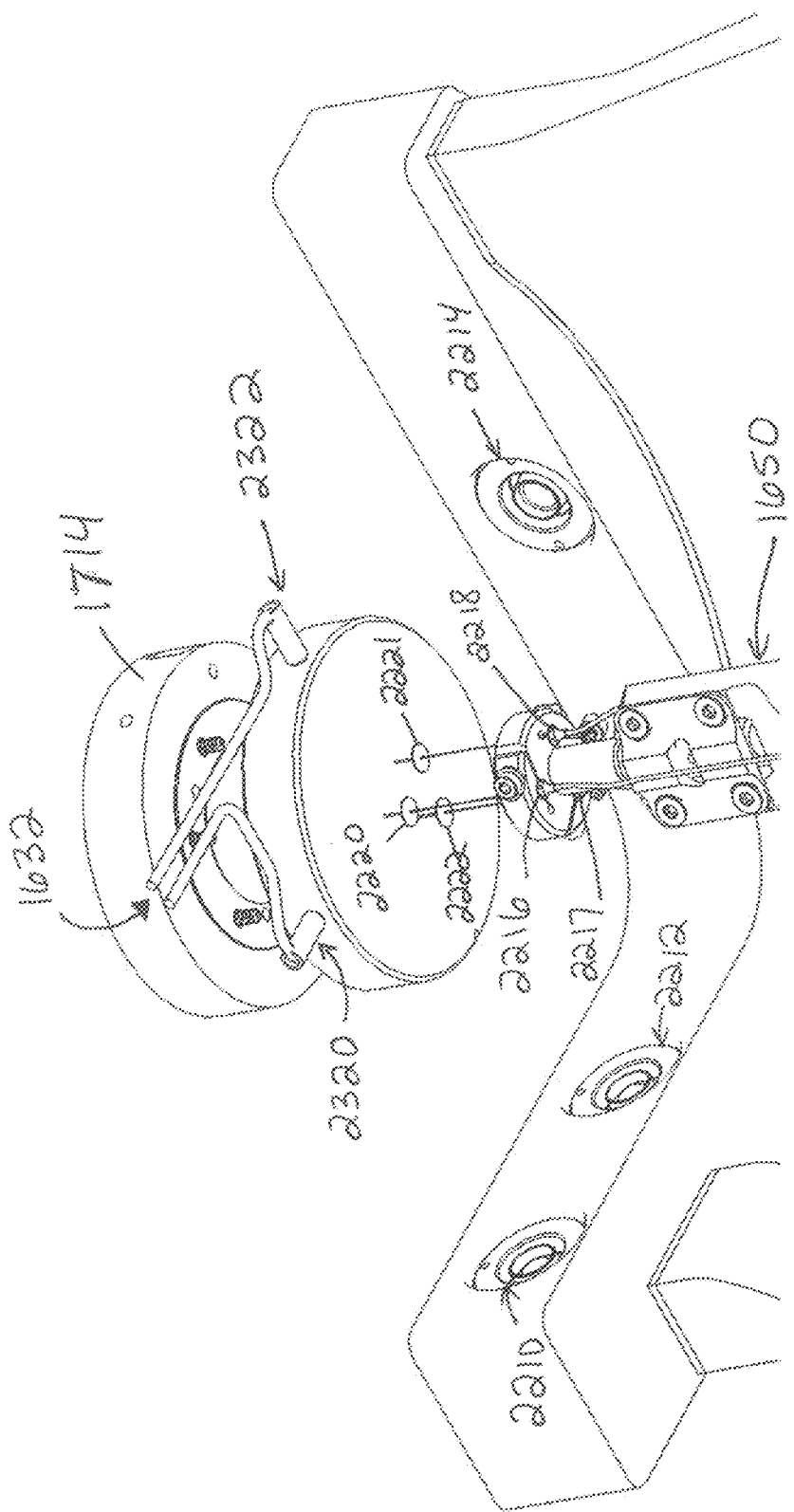
FIG. 23 is a perspective view illustrating a bottom surface of the reference cylinder and showing the interferometric sensors and capacitive sensors, with the capacitive sensor mount removed for illustrative purposes, according to an embodiment of the present disclosure.

FIG. 16 is a perspective view illustrating the internal components of the translation state system, according to an embodiment of the present disclosure. As shown, the sample holder mount 1620 is for mounting the sample holder (not shown) to the motion system. The rotor 1625 of the rotation stage 1512 is shown. The sample holder mount 1620 is positioned laterally above the rotor 1625 within the housing. The rotation stage 1512 is positioned laterally above a capacitive sensor housing 1630. The output 1632 of the capacitive sensors (not shown) provides a connection point for appropriate circuitry or interconnections to gather information from the capacitive sensors of the capacitive sensor housing 1630. The capacitive sensor housing 1630 is positioned laterally above the fine motion 6-axis stage 1514. The fine motion 6-axis stage 1514 is mounted on a base 1635. The base 1635 also provides an anchor point for the hexapod motors 1640, 1642, 1644, 1646, and 1648. A sixth hexapod motor is anchored to the base 1635, which is not visible in FIG. 16 (refer to FIG. 18 showing the hexapod motor 1830). The motion system includes an interferometer tower 1530 having a plurality of feedback sensors proximate a top portion of the motion system. The motion system also includes an interior, central interferometer tower 1650 that verifies the position of the rotation stage 1512, as will be appreciated in light of the present disclosure. Refer to FIGS. 22 and 23 for detailed views of the interferometric sensors of the interferometer tower 1530 and the central interferometer tower 1650.

The interferometer tower 1650 can serve as a global reference for the system, and is constructed using a low coefficient of thermal expansion (CTE) material such as Invar or Zerodur. As such, the dimensional stability of the interferometer tower 1650 is improved thus ensuring the interferometers are thermally stable at a much longer time scale compared to other system components.

FIG. 17 is a perspective partial cut-out view of the motion system illustrating the housing and internal components, according to an embodiment of the present disclosure. As shown, the motion system includes the sample holder 1510, the rotation stage 1512, the fine motion 6-axis stage 1514, and the coarse motion 6-axis hexapod 1520. Also shown in FIG. 17 is the capacitive sensor housing 1630. The capacitive sensors within the capacitive sensor housing 1630 are used to verify the position of the motion system. A reference cylinder 1714 is also shown in FIG. 17, which is used to verify the position of the rotation stage 1512. The rotation stage 1512 is within the vacuum chamber, positioned laterally above the fine motion 6-axis stage 1514. The fine motion s-axis stage 1514 is within the vacuum chamber, positioned laterally above the coarse motion 6-axis hexapod 1520. The coarse motion 6-axis hexapod 1520 is laterally below the rotation stage 1512 and the fine motion 6-axis stage 1514.

FIG. 18 is a cross-sectional view illustrating the motion system, vacuum chamber, and various sensors, according to an embodiment of the present disclosure. As shown, a vacuum chamber 1810, which may also be referred to herein as a housing, has the components of the sample imaging system contained therein. The vacuum chamber 1810 typically includes various components for creating an ultra-high vacuum (UHV) therein. The vacuum components can include a vacuum automation system controlled through a dedicated vacuum control board, vacuum automation software, one dry pump, one ion pump mounted on the main chamber, one turbo molecular pump mounted on an airlock, and one ion pump mounted in the airlock. The vacuum chamber 1810 can be equipped with a metal and glass door. The door can be opened manually for sample introduction into the airlock. The airlock vacuum can be switch controlled from a front panel of the main chamber. The sample transfer from airlock to the main chamber is fully automated using motorized transfer rods, which are UHV compatible. The airlock is self-pumped by the turbo pump and the vacuum is controlled by a dedicated gauge. The airlock allows the introduction of a predefined sample. The sample is bakeable due to a radiant heater in order to desorb water off it before introduction. The housing can be comprised of steel, which provides UHV capability, good vibrational damping, and machinability for customization.

Also visible in FIG. 18 is the spectral energy detector 1820 and an energy beam generator 1822. The sixth hexapod motor 1830 is also shown in FIG. 18. Within the vacuum chamber 1810, the spectral energy detector 1820 and the energy beam generator 1822 are positioned proximate the sample holder 1510. The sample holder 1510 is mounted on the sample holder mount 1620 and is laterally above the sample holder mount 1620 within the vacuum chamber 1810. The sample holder mount 1620 is mounted on, and positioned laterally above, the reference cylinder 1714. As will be appreciated in light of the present disclosure, the reference cylinder 1714 provides a precision surface to be tracked by the capacitive sensors (not visible in FIG. 18, but positioned within the vacuum chamber 1810), and the interferometer tower 1530, including the portion of the interferometer tower holding the three upward looking interferometers on the central interferometer tower 1650 to verify the position of the motion system. The reference cylinder 1714 is positioned laterally above the fine motion 6-axis stage 1514 within the vacuum chamber 1810. The fine motion 6-axis stage 1514 is mounted laterally above the base 1635. In some embodiments, the fine motion 6-axis stage 1514 is mounted directly on the base 1635, or can be mounted indirectly to the base 1635 through appropriate hardware and/or fasteners. The base 1635 has the upper portion of hexapod motors (1646, 1648, and 1830 visible in FIG. 18) secured to a lower surface of the base 1635. The lower portions of the hexapod motors are secured to the coarse motion 6-axis hexapod 1520. The hexapod motors may be secured directly to the coarse motion 6-axis hexapod 1520, or indirectly through appropriate hardware, fasteners, or other intermediate components.

To ensure vacuum compatibility and minimal interference with system operation (e.g., magnetism), some customization of the vacuum chamber 1810 and internal components may occur without affecting the overall operation of the system. Any ferrous steel in the vacuum chamber housing should be replaced with non-magnetic materials, such as aluminum or titanium. It is also desirable to mitigate heat generated from the actuator motors used to drive each motion stage. Thus, the hexapod motors can include a power-off, self-lock function when not in use. In other words, after the hexapod motors move the sample to a new location for fine scanning, the individual drive axes of the hexapod can be designed to hold in a stable position when power is cut off, thus eliminating the self-heating that would otherwise occur.

FIGS. 19-21 are graphical diagrams illustrating the various degrees-of-freedom afforded by the motion system, according to an embodiment of the present disclosure. FIG. 19 is a graphical diagram illustrating the first degree-of-freedom afforded by the rotation stage, allowing for rotation along $\Theta_Z$. FIG. 20 is a graphical diagram illustrating the second, third, fourth, fifth, sixth, and seventh degrees-of-freedom afforded for the motion system by the fine motion stage, including, respectively, movement along $X_F$, movement along $Y_F$, movement along $Z_F$, rotation along $\Theta_{XF}$, rotation along $\Theta_{YF}$, and rotation along $\Theta_{ZF}$. The $Y_F$ direction of movement is parallel to the $X_F$ direction of movement. The $Z_F$ direction of movement is parallel to both the $X_F$ direction of movement and the $Y_F$ direction of movement. FIG. 21 is a graphical diagram illustrating the eighth, ninth, tenth, eleventh, twelfth, and thirteenth degrees-of-freedom afforded for the motion system by the coarse motion stage. The eighth degree-of-freedom is movement along the $X_C$ axis of movement, the ninth degree-of-freedom is movement along the $Y_C$ axis of movement, the tenth degree-of-freedom is movement along the $Z_C$ axis of movement, the eleventh degree-of-freedom is rotation along $\Theta_{XC}$, the twelfth degree-of-freedom is rotation along $\Theta_{YC}$, and the thirteenth degree-of-freedom is rotation along $\Theta_{ZC}$. The $Y_C$ direction of movement is parallel to the $X_C$ direction of movement. The $Z_C$ direction of movement is parallel to both the $X_C$ direction of movement and the $Y_C$ direction of movement.

FIG. 22 is a perspective view illustrating a bottom surface of the capacitive sensor housing 1630 and the reference cylinder 1714 of the motion system, according to an embodiment of the present disclosure. The capacitive sensor housing 1630 includes capacitive sensors mounted at capacitive sensor mount 1612 and capacitive sensor mount 2205. The capacitive sensors at capacitive sensor mount 1612 and capacitive sensor mount 2205 are used to verify the position of the motion system (refer, for example, to capacitive sensors 2320, 2322, shown in FIG. 23). The output 1632 provides a connection point for coupling the capacitive sensors to an appropriate output. As shown in FIG. 22, the interferometer tower 1530 includes feedback sensors 2210, 2212, and 2214, which provide feedback information regarding the position of the motion system. The central interferometer tower 1650 includes sensors 2216, 2217, and 2218. The sensors 2216, 2217, and 2218 interface with mirrors 2220, 2221, and 2222, respectively, on the reference cylinder 1714.

By positioning interferometers to interface with the top of the sample holder and the base of the rotation stage, the only errors that must be measured in an open loop are X and Z translational runout errors from the rotation stage. These errors are measured using the capacitive sensors. All other errors are included within the closed loop correction system and are thus corrected during measurement, as will be appreciated in light of the present disclosure. Refer to FIG. 26 showing an example closed loop correction technique that implements the interferometric sensors to correct errors in the system.

Figure 28:
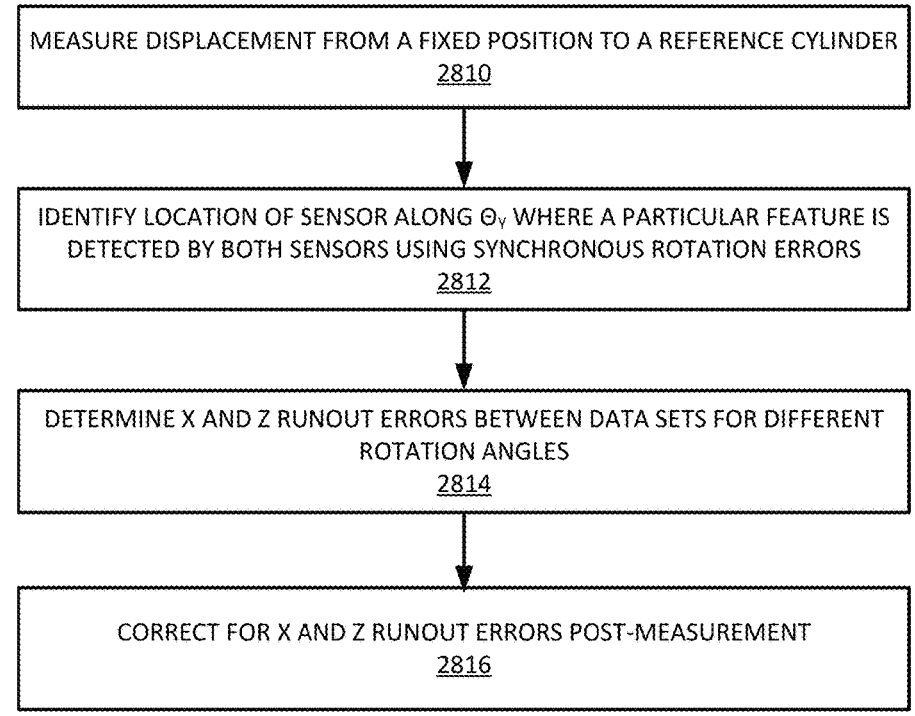
FIG. 28 is a flowchart illustrating a method for performing open loop correction post-measurement, according to an embodiment of the present disclosure.
Figure 29:
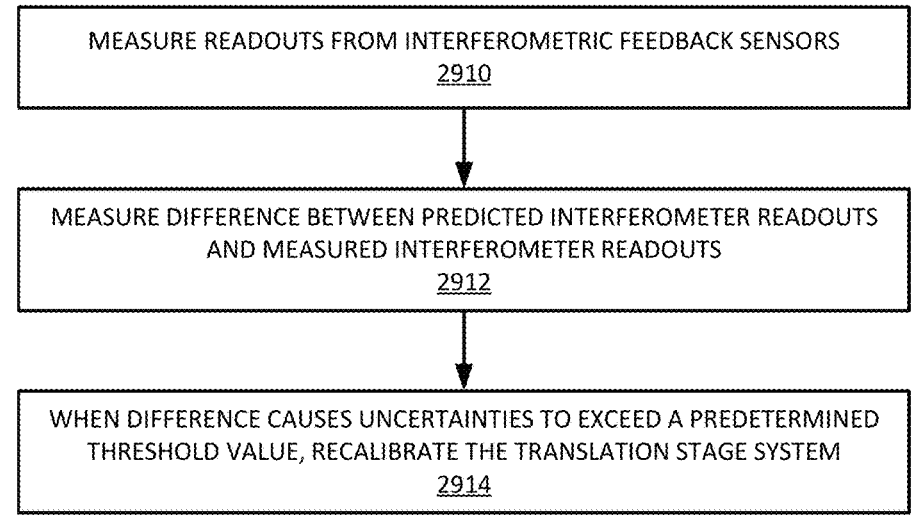
FIG. 29 is a flowchart illustrating a method for performing drift monitoring and correction post-measurement, according to an embodiment of the present disclosure.

FIG. 23 is a perspective view illustrating a bottom surface of the reference cylinder 1714 and showing the interferometric sensors 2210, 2212, 2214, 2216, 2217, 2218 and capacitive sensors 2320, 2322, with the capacitive sensor mount removed for illustrative purposes, according to an embodiment of the present disclosure. The capacitive sensors 2320, 2322 are clearly visible in FIG. 23. The capacitive sensors 2320, 2322 can be mounted either directly on the mount, or indirectly by appropriate fasteners, hardware, or other intermediate components. Refer, for example, to FIG. 28 showing a flowchart of a method for correction using the capacitive sensors 2320, 2322. Refer, for example, to FIG. 29 showing a flowchart of a method for drift monitoring and correction using the interferometric feedback sensors 2210, 2212, 2214, 2216, 2217, 2218.

Figure 24:
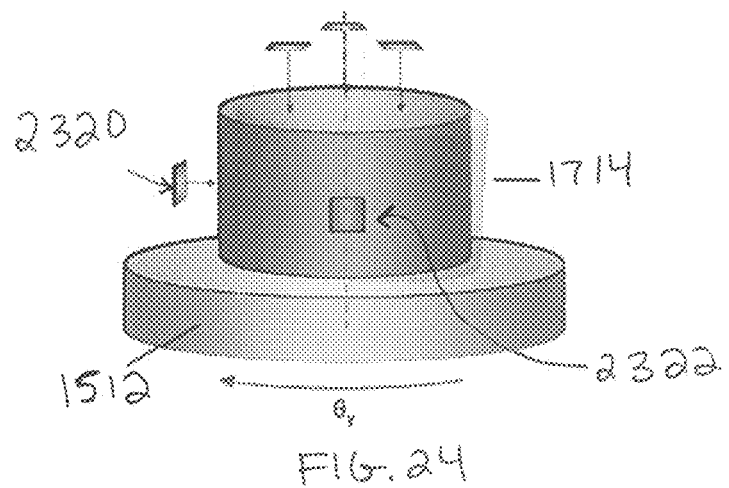
FIG. 24 is a perspective view illustrating the reference cylinder and the rotation stage of the motion system, according to an embodiment of the present disclosure.

FIG. 24 is a perspective view illustrating the reference cylinder 1714 and the rotation stage 1512 of the motion system, according to an embodiment of the present disclosure. As shown in FIG. 24, the capacitive sensors 2320, 2322 use the reference cylinder 1714 to determine the actual position of the rotation stage 1512. The reference cylinder 1714 allows for the position to be estimated so that any errors between the actual position and the estimated (nominal) position can be accounted for. The nominal position refers to the position where the system believes that it is located, which is compared to its actual position for correction as needed. Refer, for example, to FIG. 28 showing a flowchart for open loop correction using the capacitive sensors 2320, 2322.

Figures 25A, 25B:
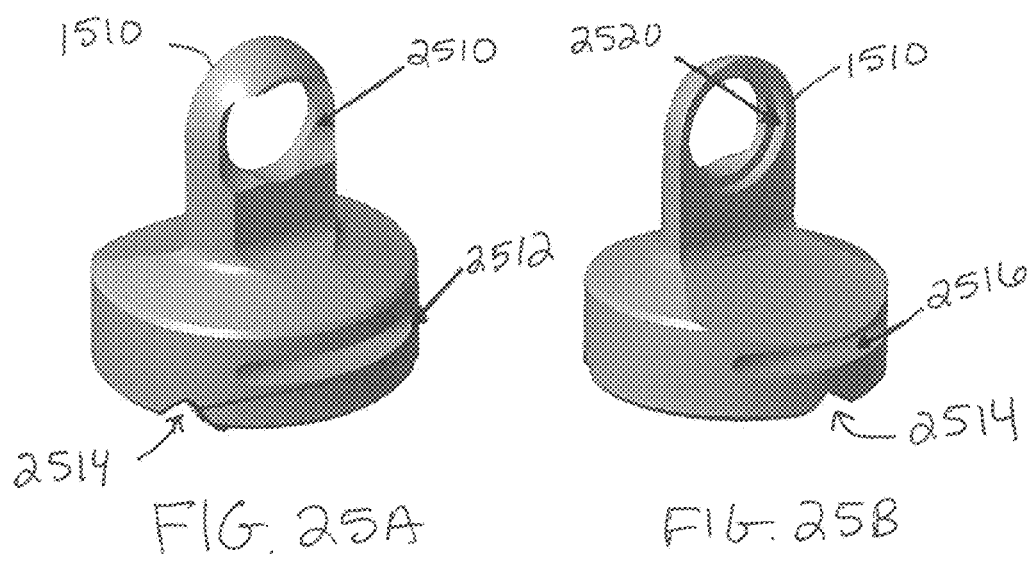
FIG. 25A is a perspective view illustrating a first side of the sample holder of the motion system, according to an embodiment of the present disclosure.
FIG. 25B is a perspective view illustrating a second side of the sample holder of the motion system, according to an embodiment of the present disclosure.

FIG. 25A is a perspective view illustrating a first side of the sample holder 1510 of the motion system, according to an embodiment of the present disclosure. FIG. 25B is a perspective view illustrating a second side of the sample holder 1510 of the motion system, according to an embodiment of the present disclosure. The second side of the sample holder 1510 is opposite the first side of the sample holder 1510.

The sample holder 1510 is for securely mounting the target (when used) and sample to the motion system. As shown in FIG. 25B, the sample holder 1510 includes a pocket 2520 for receiving the sample and target. The pocket 2520 can, for example, be 1 cm by 1 cm in size, or may be a circular opening having a diameter of approximately 1 cm. The portion of the sample holder 1510 that includes the pocket 2520 is elongated to ensure the sample holder base will not collide with the electron beam generator column at large rotation angles. In some embodiments, additional features may be incorporated into the sample holder 1510 to accommodate correction features, accessibility, and mounting attachment. For example, the sample holder 1510 includes a bevel 2510 to not obscure X-rays (for example, when at a large rotation angle). The sample holder 1510 includes a kinematic locator groove 2514. This can interface with a surface of the sample holder mount (for example, sample holder mount 1620 shown in FIGS. 17-18). In an example, the kinematic locator groove 2514 can mate directly with a corresponding set of ball bearings attached to the top of the reference cylinder. The sample holder 1510 further includes load lock fork grooves 2512, 2516 for loading the sample holder 1510 onto the sample holder mount by an appropriate fork of the system. The load lock fork grooves 2512, 2516 may also be referred to as slots, and are used in the two-stage load-lock system to rapidly load and/or unload the sample without breaking vacuum within the central chamber (for example, vacuum chamber 1810). The semi-kinematic mounting system (kinematic locator groove 2514) can be used to attach the sample holder 1510 to the motion system to ensure a repeatable, high precision, and low stress attachment. This positive clamping system ensures the sample holder 1510 is securely fixed to the stage system.

The sample holder 1510 is likely manufactured from a low CTE material such as Invar or Zerodur. The electron beam generator can have an operating voltage of up to 20 keV, 30 keV, 40 keV, or 50 keV, and will deposit approximately as much as 1 mW, 3 mW, 5 mW, or 10 mW of power, which is approximately 0.001 Joules per second, 0.003 Joules per second, 0.005 Joules per second, or 0.010 Joules per second. In one particular implementation the electron beam generator has an operating voltage of 28 keV. Thus, the sample holder 1510 is constructed from materials having heat conductivity constants sufficient to conduct this heat away from the sample. The sample holder 1510 is mechanically rigid in order to minimize spatial distortion of the system during the data collection. X-rays generated in the target volume are produced isotropically, and the sample holder 1510 includes the bevel 2510 so as to not block them in either forward propagation or backward propagation. The bevel 2510 enhances angular range with respect to non-shadowing as well as sample rotation without collision. In some embodiments, it may be desirable during data collection to either replace the target with a different thickness target (perhaps multiple times) or to perform additional thin film deposition of the target material to obtain greater x-ray flux. In other embodiments, it may be desirable to introduce multi-element nanopatterning embedded in a target matrix material for higher resolution (smaller spot size for X-ray generation) imaging. The matrix material itself may also be used for source X-ray flux and imaging. Thus, the sample holder 1510 should be load-lock compatible, in that the components do not block the sample from being loaded and unloaded into the chamber. This is achieved by the load lock fork grooves 2512, 2516. The sample holder 1510 is a passive component (no wiring required).

The system components shown and described herein can implement one or more methods described herein to achieve imaging of a sample or error correction of the sample.

Methodology—Error Correction

To ensure accuracy of results when imaging the sample, it is sought to identify potential error sources that may occur during stage assembly and to account for these during measurement and post-measurement. For example, most motion systems will be assembled to within a 10 μm static tolerance, which is 10,000 nm. Given a target imaging accuracy of 10 nm or less, this static assembly tolerance greatly exceeds the resolution target. Further, the coarse motion stages can achieve a translational repeatability of 1,000 nm and will likely introduce crosstalk between all six degrees of motion for the coarse motion stage. Stage components are also subject to temporal drift errors, which is of particular issue in a vacuum environment where parasitic heat sources can easily lead to thermal expansion effects that exceed 1,000 nm along the dimensions of the stage system.

To overcome these and other error sources, a hybrid closed-loop and open-loop approach is implemented which actively corrects as many static errors as possible within the motion system. Errors that cannot be actively corrected will be measured and corrected post-measurement. Once the system is initially set up, coarse motion error will be corrected using a control loop and temporal drift errors will be monitored and corrected.

Figure 27:
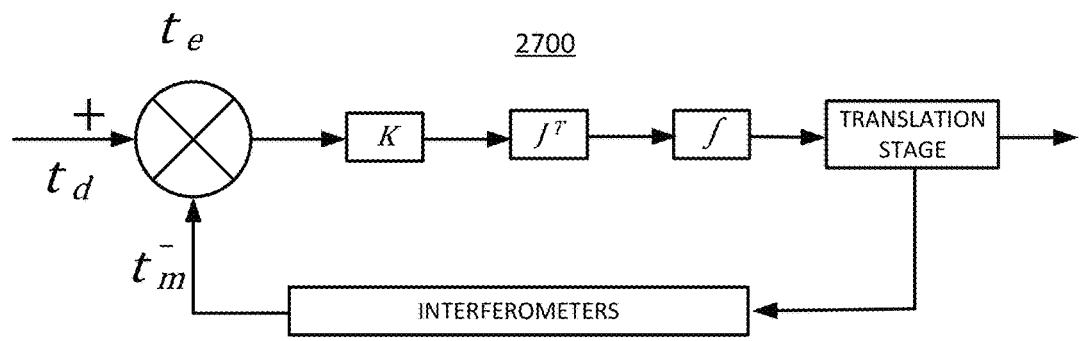
FIG. 27 is a flowchart illustrating a method for performing a control loop for correction of the coarse translation stage motion of the motion system, according to an embodiment of the present disclosure.

It will be appreciated in light of the present disclosure that the systems herein can implement one or more of the following example methods, and may implement further methods in addition to those disclosed herein. FIGS. 26 and 27 show example flowcharts of methods performed to correct errors in the system during measurement of data. FIGS. 28 and 29 show methods for correcting for errors post-measurement.

FIG. 26 is a flowchart illustrating a method 2600 for performing closed loop correction of the fine stage of the motion system, according to an embodiment of the present disclosure. As described in conjunction with FIGS. 22 and 23, the interferometric feedback sensors 2210, 2212, 2214 are used in performing the closed loop correction of the fine stage of the motion system. Referring back to FIG. 26, the method 2600 commences at 2610 by monitoring the motion along all axes, including translation and rotation. If static mounting errors are present in the stage system, these feedback sensors track stage motion that deviates from nominal motion input by a user. At 2612, the method measures the difference between the actual stage position and the nominal stage position. At 2614, the fine motion 6-axis stage is used to correct these static errors.

The closed loop system shown in FIG. 26 is formulated based on the minimization of the mean squared error between predicted interferometer readouts from a nominal stage system and measured interferometer readouts. For this minimization, static mounting errors in the nominal stage are treated as fitting parameters to be solved for. By solving for these static mounting errors, the fine axis stage control can be effectively mapped to the interferometer readouts. To generate sufficient data for this minimization to converge, the fine 6-axis stage is swept along all six axes of motion to create a unique set of independent data where for each position, the interferometer readouts are measured. To determine the corresponding set of predicted interferometer readouts, the motion system is modeled using a dual quaternion formulation. Dual quaternions provide a stable, compact, and computationally efficient formulation for translational and rotational transforms. The convenience of dual quaternions is the ability to chain multiple translation and rotation transforms through simple multiplication of dual quaternions representing these transforms. By modeling stage motion and static mounting errors with dual quaternions, a complete model of the motion can be created by multiplying dual quaternions in the order in which the motion is assembled while carefully including relevant errors at each stage interface. Using this formulation, the location and orientation of the reference mirrors used by the interferometers can be used. To then determine the interferometer readouts, the interferometers are modeled as a vector defined by two points modified by a dual quaternion representing mounting errors for the interferometers. Using standard plane-line intersection formulas, the predicted interferometer readouts are then derived.

FIG. 27 is a flowchart illustrating a method 2700 for performing a control loop for correction of the coarse motion of the motion system, according to an embodiment of the present disclosure. Once the static mounting errors are resolved within the closed loop system (according to the method 2600 shown in FIG. 26, for example), the fine 6-axis stage is fully mapped to the interferometric feedback sensors. However, when a coarse motion is used, further uncertainties in the direction of intended motion and crosstalk along all other axes can break this mapping. A control loop can be implemented, rather than a full system recalibration, in which the six additional unknowns that are introduced by the coarse motion system are corrected for. This enables minimal correction time, thereby maximizing time available for measurement and gathering of data. The control loop is shown in FIG. 27, and the fine motion stage is used to actively correct for these errors once determined by the least squares minimization routine. In the control loop, the desired output based on $\Theta(t_d)$, the measured output $(t_m)$ and the difference of $|t_d-t_m|(t_e)$ are put into a summing junction which is fed to Gain constant (K), and undergoes a Jacobian transpose $J^T$ to the motion. The interferometers are used to provide the measured output. The value of $\Theta$ for the fine stage includes the angle for each of the stage motors to provide the precise desired angle.

The control loop correction of coarse translation motion error shown in FIG. 27 continues until $t_e$, the difference of $|t_d-t_m|$, is below a predetermined threshold value. Once the difference is below the predetermined threshold value, it is no longer necessary to correct the coarse motion errors.

FIG. 28 is a flowchart illustrating a method 2800 for performing open loop correction post-measurement, according to an embodiment of the present disclosure. Any remaining static stage errors that are not captured in the closed loop system are measured in an open loop manner and corrected post-measurement. One possible source of errors can originate from the coarse $\Theta_Y$ rotation stage. The rotation stage can introduce X, Y, and Z, runout (translation), and $\Theta_X \Theta_Z$ wobble (tilt) errors. All tilt errors and Y runout errors will be included in the closed loop system. However, X and Z runout errors will not be included and are thus measured.

The method 2800 commences at 2810 by measuring X and Z runout errors from a fixed position to a reference cylinder. The capacitive sensors measure the displacement from a fixed position to a reference cylinder as the rotation stage rotates. The capacitive sensors can have a working distance of 20 to 100 μm. The reference cylinder can be diamond-turned to minimize eccentricity. The challenge of the open loop measurement is extracting relevant X and Z motion of the sample since the location of the capacitive sensors along $\Theta_Y$ is assumed to be unknown. At 2812, the synchronous rotation errors are used to identify the location of the sensor along $\Theta_Y$ where a particular feature is detected by both sensors. At 2814, once the sensor locations are found, X and Z runout errors between datasets for different rotation angles can be determined. At 2816, the X and Z runout errors that were determined are corrected for post-measurement.

FIG. 29 is a flowchart illustrating a method 2900 for performing drift monitoring and correction post-measurement, according to an embodiment of the present disclosure. Temporal drift is an inherently unavoidable source of error for the motion system. However, drift can be accounted for so long as there is a monitoring mechanism and correction procedure in place. To monitor the extent of drift within the motion, the interferometric feedback sensors are used. At 2910, the readouts from the interferometric feedback sensors can be measured. Initially, the readouts from the interferometric feedback sensors will match the predicted interferometer readouts using fitted error parameters. As the drift error increases, at 2912, a difference, $|t_e|$ between the predicted interferometer readouts and the measured interferometer readouts will arise. At 2914, when the difference causes positional uncertainties to exceed a predetermined threshold value (for example, 5 nm), the motion system is recalibrated according to the correction techniques described herein. This difference between the predicted interferometer readouts and the measured interferometer readouts is monitored and recorded as metadata. The drift errors measured by the capacitive sensors will be recorded as metadata and used for post-measurement correction.

It will be appreciated in light of the present disclosure that, although shown and described with reference to an IC sample, the techniques and systems herein are likewise applicable to imaging other samples, such as energy conversion and storage structures (e.g., batteries), nanoelectronics structures, and bodily structures (e.g., brain tissue). For example, a battery could be imaged using the techniques disclosed herein. Moreover, although described with reference to sub-micron or nanoscale structures such as ICs having an area of 1 centimeter or less, it will be appreciated in light of the present disclosure that the techniques are likewise applicable to larger samples, and can readily adapt to multiple resolutions as needed to image a wide variety of samples.

It will also be appreciated that the preceding are example methods, which may be modified, changed, or otherwise revised in accordance with the present disclosure, and also other methods can be implemented by the systems herein. Likewise, the example methods may be implemented by any appropriate system for imaging a sample that is within the scope of the present disclosure.

Further Example Embodiments

The following examples pertain to further embodiments, from which numerous permutations and configurations will be apparent.

Example 1 is a system for imaging an integrated circuit sample. The system comprises a sample holder configured to secure the integrated circuit sample. The system further comprises an electron beam generator configured to produce an electron beam within a vacuum chamber. The system further comprises an electron detector configured to measure electrons that have interacted with the integrated circuit sample. The system further comprises a spectral X-ray detector configured to measure first X-rays resulting from the electron beam interacting with the integrated circuit sample and second X-rays transmitted through the integrated circuit sample. The second X-rays result from the electron beam interacting with a target that is positioned between the electron beam generator and the sample holder. The system further comprises a memory device configured to store data generated by the electron detector and the spectral X-ray detector.

Example 2 is the system of Example 1, further comprising a processor configured to reconstruct the integrated circuit sample using the data stored in the memory device.

Example 3 is the system of Example 1, further comprising a processor configured to perform a three-dimensional reconstruction of the integrated circuit sample.

Example 4 is the system of Example 1, wherein the electron detector comprises at least one of (a) a backscattered electron detector configured to measure backscattered electrons resulting from the electron beam interacting with the integrated circuit sample; and (b) a secondary electron detector configured to measure secondary electrons resulting from the electron beam interacting with the integrated circuit sample.

Example 5 is the system of Example 1, further comprising a movable platform that supports the sample holder.

Example 6 is the system of Example 5, wherein the movable platform provides translational and rotational movement of the integrated circuit sample.

Example 7 is the system of Example 5, further comprising an interferometric tower and at least one interferometric sensor positioned on the movable platform. Data collected by the at least one interferometric sensor enables a position estimation of the movable platform to be performed.

Example 8 is the system of Example 5, further comprising one or more capacitive sensors on the movable platform. Data collected by the one or more capacitive sensors enables a position estimation of the movable platform to be performed.

Example 9 is the system of Example 5, further comprising a motor configured to provide translational and rotational movement of the movable platform.

Example 10 is the system of Example 1, wherein the spectral X-ray detector comprises a silicon drift detector that positioned adjacent to the electron beam generator.

Example 11 is the system of Example 1, wherein the spectral X-ray detector comprises a transition edge sensor camera.

Example 12 is the system of Example 1, wherein the electron beam generator that produces the electron beam is a scanning electron microscope.

Example 13 is a system for imaging a sample. The system comprises a sample holder configured to secure the sample. The system further comprises an electron beam generator configured to produce an electron beam within a vacuum chamber. The system further comprises a first spectral X-ray detector, positioned adjacent to the electron beam generator, that is configured to measure first X-rays resulting from the electron beam interacting with the sample. The system further comprises a second spectral X-ray detector, spaced apart from the electron beam generator and the first spectral X-ray detector, that is configured to measure second X-rays resulting from the electron beam interacting with a target that is positioned between the electron beam generator and the sample holder. The system further comprises a processor configured to receive data generated by the first spectral X-ray detector and the second spectral X-ray detector. The processor is further configured to perform a three-dimensional reconstruction of the sample.

Example 14 is the system of Example 13, further comprising a backscattered electron detector configured to measure backscattered electrons resulting from the electron beam interacting with the sample. The system further comprises a secondary electron detector configured to measure secondary electrons resulting from the electron beam interacting with the sample.

Example 15 is the system of Example 13, further comprising a movable platform that supports the sample holder, and that provides translational and rotational movement of the sample.

Example 16 is the system of Example 15, further comprising an optical light source within the vacuum chamber. The system further comprises at least one interferometric sensor positioned on the movable platform. Data collected by the at least one interferometric sensor enables a position estimation of the movable platform to be performed.

Example 17 is the system of Example 16, further comprising one or more capacitive sensors. Data collected by the one or more capacitive sensors enables a supplemental position estimation of the movable platform to be performed.

Example 18 is the system of Example 15, further comprising a motor configured to provide translational and rotational movement of the movable platform.

Example 19 is the system of Example 13, wherein the first spectral X-ray detector and the second spectral X-ray detector each comprise a detector selected from a group consisting of a transition edge sensor camera and a silicon drift detector.

Example 20 is method for imaging a sample using a system having an electron beam generator that produces an electron beam that interacts with the sample. The method comprises acquiring first data over a first area of the sample in a first mode of operation by measuring backscattered electrons at two electron detectors. The backscattered electrons result from the electron beam interacting with the sample. The method further comprises acquiring second data over a second area of the in a second mode of operation by photon counting of X-rays with a forward direction of travel that is away from the electron beam generator. The counted X-rays result from the electron beam interacting with a target positioned between the electron beam generator and the sample. A spectral X-ray detector is used to acquire the second data. The method further comprises performing an inversion on the first data and the second data. The method further comprises acquiring one or more model priors for the sample. The method further comprises generating a reconstruction of the sample using the one or more model priors and the inverted first and second data.

Example 21 is the method of Example 20, wherein generating the reconstruction of the sample comprises generating a three-dimensional reconstruction of the sample.

Example 22 is the method of Example 20, further comprising comparing the reconstruction of the sample with a trusted standard. The method further comprises making a determination that discrepancies exist between the reconstruction of the sample and the trusted standard.

Example 23 is the method of Example 20, wherein the spectral X-ray detector is selected from a transition edge sensor camera array and a silicon drift detector. Acquiring the first data in the first mode of operation comprises collecting secondary electrons at a secondary electron detector and collecting the backscattered electrons at the secondary electron detector and a backscattered electron detector.

Example 24 is the method of Example 20, wherein the spectral X-ray detector comprises a transition edge sensor camera. Acquiring the second data in the second mode of operation comprises collecting the X-rays at the transition edge sensor camera and collecting metadata about the target using the transition edge sensor camera.

Example 25 is the method of Example 20, further comprising defining an optimal data acquisition strategy by assessing output from the inversion and identifying regions of the sample where convergence has not been met. The method further comprises acquiring third data in the second mode of operation using a multiresolution sampling strategy at the spectral X-ray detector. The third data comprises X-ray transmission spectra corresponding to pixels of the spectral X-ray detector. The method further comprises performing multiscale inversions on the X-ray transmission spectra.

Example 26 is the method of Example 20, wherein the sample is an integrated circuit sample. Generating the reconstruction of the sample comprises generating a three-dimensional reconstruction of the integrated circuit sample. The method further comprises converting the three-dimensional reconstruction of the integrated circuit sample into a GDSII binary format.

Example 27 is a system for imaging a sample. The system comprises a sample holder configured to secure the sample within a vacuum chamber. The system further comprises an electron beam generator configured to produce an electron beam within the vacuum chamber. The system further comprises an electron detector configured to measure electrons from the electron beam that have interacted with the sample. The system further comprises a spectral energy detector configured to measure fluorescent X-rays resulting from the electron beam interacting with at least one of (a) the sample and (b) a target positioned between the sample and the electron beam generator. The system further comprises a coarse motion stage capable of moving the sample holder along and around each of an x-axis, a y-axis, and a z-axis, thereby providing the sample holder with a first set of six degrees-of-freedom. The system further comprises a fine motion stage that is coupled to the coarse motion stage, and that is also capable of moving the sample holder along and around the x-axis, the y-axis, and the z-axis, thereby providing the sample holder with a second set of six degrees-of-freedom. The fine motion stage has a higher resolution of movement than the course motion stage. The system further comprises a controller that is communicatively coupled with the electron beam generator, the electron detector, the spectral energy detector, the fine motion stage, and the coarse motion stage. The system further comprises a processor configured to receive data from the electron detector and the spectral energy detector. The processor is further configured to generate control instructions that, when implemented by the controller, result in movement of at least one of the fine motion stage and the coarse motion stage.

Example 28 is the system of Example 27, further comprising a rotation stage that is within the vacuum chamber and that is coupled to the fine motion stage. The rotation stage provides the sample holder with a thirteenth degree-of-freedom, in addition to the first and second sets of six degrees-of-freedom.

Example 29 is the system of Example 27, wherein the electron detector is a backscattered electron detector.

Example 30 is the system of Example 27, wherein the electron detector is a secondary electron detector.

Example 31 is the system of Example 27, further comprising a first spectral energy detector configured to measure fluorescent X-rays resulting from the electron beam penetrating the sample. The system further comprises a second spectral energy detector configured to measure X-rays resulting from the electron beam interacting with the target.

Example 32 is the system of Example 27, further comprising a rotation stage that is within the vacuum chamber and that is coupled to the fine motion stage. The rotation stage provides the sample holder with a thirteenth degree-of-freedom, in addition to the first and second sets of six degrees-of-freedom. The system further comprises a plurality of interferometric sensors positioned in an interferometer tower, including a first interferometric sensor in communication with a first reference mirror on the rotation stage, and a second interferometric sensor in communication with a second reference mirror on the sample holder.

Example 33 is the system of Example 27, further comprising a rotation stage that is within the vacuum chamber and that is coupled to the fine motion stage. The rotation stage provides the sample holder with a thirteenth degree-of-freedom, in addition to the first and second sets of six degrees-of-freedom. The system further comprises one or more capacitive sensors that are positioned on the rotation stage and configured to measure a position of the rotation stage.

Example 34 is a system for imaging a sample. The system comprises a sample holder configured to secure the sample within a vacuum chamber. The system further comprises an electron beam generator configured to produce an electron beam within the vacuum chamber. The system further comprises a coarse motion stage positioned within the vacuum chamber. The coarse motion stage provides movement along a first axis that provides a first degree-of-freedom. The coarse motion stage also provides movement along a second axis perpendicular to the first axis that provides a second degree-of-freedom. The coarse motion stage also provides movement along a third axis perpendicular to the first and second axes that provides a third degree-of-freedom. The coarse motion stage also provides rotation around the first axis that provides a fourth degree-of-freedom. The coarse motion stage also provides rotation around the second axis that provides a fifth degree-of-freedom. The coarse motion stage also provides rotation around the third axis that provides a sixth degree-of-freedom. The system further comprises a fine motion stage positioned within the vacuum chamber laterally above the coarse motion stage. The fine motion stage provides movement along a fourth axis that provides a seventh degree-of-freedom. The fine motion stage also provides movement along a fifth axis perpendicular to the fourth axis that provides an eighth degree-of-freedom. The fine motion stage also provides movement along a sixth axis perpendicular to the fourth and fifth axes that provides a ninth degree-of-freedom. The fine motion stage also provides rotation around the fourth axis that provides a tenth degree-of-freedom. The fine motion stage also provides rotation around the fifth axis that provides an eleventh degree-of-freedom. The fine motion stage also provides rotation around the sixth axis that provides a twelfth degree-of-freedom. The system further comprises a rotation stage positioned within the vacuum chamber laterally above the fine motion stage. The rotation stage provides rotation around a seventh axis that provides a thirteenth degree-of-freedom.

Example 35 is the system of Example 34, further comprising at least one of (a) a backscattered electron detector configured to measure backscattered electrons resulting from the electron beam interacting with the sample; and (b) a secondary electron detector configured to measure secondary electrons resulting from the electron beam interacting with the sample.

Example 36 is the system of Example 34, further comprising a first spectral energy detector configured to measure fluorescent X-rays resulting from the electron beam penetrating the sample. The system further comprises a second spectral energy detector configured to measure X-rays resulting from the electron beam interacting with a target positioned between the electron beam generator and the sample.

Example 37 is the system of Example 34, further comprising a controller configured to control movement of the rotation stage, the fine motion stage, and the coarse motion stage.

Example 38 is the system of Example 34, further comprising at least one interferometric sensor positioned on an interferometer tower.

Example 39 is the system of Example 38, wherein the at least one interferometric sensor is in communication with a reference mirror coupled to the rotation stage.

Example 40 is the system of Example 38, wherein the at least one interferometric sensor is in communication with a reference mirror coupled to the sample holder.

Example 41 is the system of Example 34, further comprising a capacitive sensor that is positioned on the rotation stage and that is configured to measure a position of the rotation stage.

Example 42 is a system for imaging a sample. The system comprises a sample holder configured to secure the sample within a vacuum chamber. The system further comprises an electron beam generator configured to produce an electron beam within the vacuum chamber. The system further comprises a moving platform having a rotation stage, a fine motion stage, and a coarse motion stage. The system further comprises one or more interferometric sensors that provide interferometric measurements. The system further comprises a fixture mounted at a base of the rotation stage that supports a first set of reference mirrors that are used in providing the interferometric measurements. The system further comprises a second set of reference mirrors that are mounted to the sample holder and that are used in providing the interferometric measurements.

Example 43 is the system of Example 42, further comprising a controller configured to control rotation of the rotation stage, movement of the fine motion stage, and movement of the coarse motion stage.

Example 44 is the system of Example 43, further comprising a processor configured to use the interferometric measurements to determine a difference between an actual stage position and a nominal stage position. The controller controls movement of the fine motion stage to reduce the difference.

Example 45 is the system of Example 42, wherein the one or more interferometric sensors are mounted onto a static tower that is mounted to a base of the vacuum chamber proximate the moving platform. The one or more interferometric sensors include a first interferometric sensor adjacent to the rotation stage and a second interferometric sensor adjacent to the sample holder.

Example 46 is the system of Example 42, further comprising one or more capacitive sensors that measure a displacement of the rotation stage with respect to a reference cylinder.

Example 47 is the system of Example 46, wherein the fixture includes mounts for the one or more capacitive sensors.

Example 48 is the system of Example 42, further comprising a controller that is communicatively coupled to the rotation stage, the fine motion stage, and the course motion stage.

The system further comprises a processor configured to measure a drift error of the moving platform and generate control instructions that, when implemented by the controller, cause the moving platform to be recalibrated.

Example 49 is the system of Example 42, wherein the first set of reference mirrors provide x-direction, y-direction, and $\Theta Y$ interferometric measurements for the rotation stage.

Example 50 is the system of Example 42, wherein the second set of reference mirrors provide y-direction, $\Theta X$, and $\Theta Z$ interferometric measurements for the sample holder.

The terms and expressions which have been employed herein are used as terms of description and not of limitation, and there is no intention, in the use of such terms and expressions, of excluding any equivalents of the features shown and described (or portions thereof), and it is recognized that various modifications are possible within the scope of the claims. Accordingly, the claims are intended to cover all such equivalents. In addition, various features, aspects, and embodiments have been described herein. The features, aspects, and embodiments are susceptible to combination with one another as well as to variation and modification, as will be understood by those having skill in the art. The present disclosure should, therefore, be considered to encompass such combinations, variations, and modifications. It is intended that the scope of the present disclosure be limited not by this detailed description, but rather by the claims appended hereto. Future filed applications claiming priority to this application may claim the disclosed subject matter in a different manner, and may generally include any set of one or more elements as variously disclosed or otherwise demonstrated herein.

What is claimed is:

1. A system for imaging an integrated circuit (IC) sample, the system comprising:
   a sample holder configured to secure the IC sample;
   an electron beam generator configured to produce an electron beam within a vacuum chamber;
   an electron detector configured to measure electrons that have interacted with the IC sample;
   a spectral X-ray detector configured to measure first X-rays resulting from the electron beam interacting with the IC sample and second X-rays transmitted through the IC sample, the second X-rays resulting from the electron beam interacting with a target that is positioned between the electron beam generator and the sample holder; and a memory device configured to store data generated by the electron detector and the spectral X-ray detector.

2. The system of claim 1, further comprising a processor configured to reconstruct the IC sample using the data stored in the memory device.

3. The system of claim 1, further comprising a processor configured to perform a three-dimensional reconstruction of the IC sample.

4. The system of claim 1, wherein the electron detector comprises at least one of:
a backscattered electron detector configured to measure backscattered electrons resulting from the electron beam interacting with the IC sample; and
a secondary electron detector configured to measure secondary electrons resulting from the electron beam interacting with the IC sample.

5. The system of claim 1, further comprising a movable platform that supports the sample holder.

6. The system of claim 5, wherein the movable platform provides translational and rotational movement of the IC sample.

7. The system of claim 5, further comprising an interferometric tower and at least one interferometric sensor positioned on the movable platform, wherein data collected by the at least one interferometric sensor enables a position estimation of the movable platform to be performed.

8. The system of claim 5, further comprising one or more capacitive sensors on the movable platform, wherein data collected by the one or more capacitive sensors enables a position estimation of the movable platform to be performed.

9. The system of claim 5, further comprising a motor configured to provide translational and rotational movement of the movable platform.

10. The system of claim 1, wherein the spectral X-ray detector comprises a silicon drift detector that positioned adjacent to the electron beam generator.

11. The system of claim 1, wherein the spectral X-ray detector comprises a transition edge sensor camera.

12. The system of claim 1, wherein the electron beam generator that produces the electron beam is a scanning electron microscope.

13. A system for imaging a sample, the system comprising:
a sample holder configured to secure the sample;
an electron beam generator configured to produce an electron beam within a vacuum chamber;
a first spectral X-ray detector, positioned adjacent to the electron beam generator, that is configured to measure first X-rays resulting from the electron beam interacting with the sample;
a second spectral X-ray detector, spaced apart from the electron beam generator and the first spectral X-ray detector, that is configured to measure second X-rays resulting from the electron beam interacting with a target that is positioned between the electron beam generator and the sample holder; and
a processor configured to receive data generated by the first spectral X-ray detector and the second spectral X-ray detector, and further configured to perform a three-dimensional reconstruction of the sample.

14. The system of claim 13, further comprising:
a backscattered electron detector configured to measure backscattered electrons resulting from the electron beam interacting with the sample; and
a secondary electron detector configured to measure secondary electrons resulting from the electron beam interacting with the sample.

15. The system of claim 13, further comprising a movable platform that supports the sample holder, and that provides translational and rotational movement of the sample.

16. The system of claim 15, further comprising:
an optical light source within the vacuum chamber; and
at least one interferometric sensor positioned on the movable platform, wherein data collected by the at least one interferometric sensor enables a position estimation of the movable platform to be performed.

17. The system of claim 16, further comprising one or more capacitive sensors, wherein data collected by the one or more capacitive sensors enables a supplemental position estimation of the movable platform to be performed.

18. The system of claim 15, further comprising a motor configured to provide translational and rotational movement of the movable platform.

19. The system of claim 13, wherein the first spectral X-ray detector and the second spectral X-ray detector each comprise a detector selected from a group consisting of a transition edge sensor camera and a silicon drift detector.

20. A method for imaging a sample comprising:
directing an electron beam from an electron beam generator toward the sample and a target positioned between the sample and the electron beam generator;
acquiring first data over a first area of the sample in a first mode of operation by measuring backscattered electrons by at least two electron detectors, the backscattered electrons resulting from the electron beam interacting with the sample;
acquiring second data over a second area of the sample in a second mode of operation by photon counting of X-rays from the target using a spectral X-ray detector;
performing an inversion on the first data and the second data;
acquiring one or more model priors for the sample; and
generating a reconstruction of the sample using the one or more model priors and the inverted first and second data.

21. The method of claim 20, wherein generating the reconstruction of the sample comprises generating a three-dimensional reconstruction of the sample.

22. The method of claim 20, further comprising:
comparing the reconstruction of the sample with a trusted standard; and
making a determination that discrepancies exist between the reconstruction of the sample and the trusted standard.

23. The method of claim 20, further comprising:
acquiring the first data in the first mode of operation by collecting secondary electrons at a secondary electron detector and collecting the backscattered electrons at the secondary electron detector and a backscattered electron detector.

24. The method of claim 20, further comprising:
acquiring the second data in the second mode of operation by collecting the X-rays at a transition edge sensor (TES) camera and collecting metadata about the target using the TES camera.

25. The method of claim 20, further comprising:
defining an optimal data acquisition strategy by assessing output from the inversion and identifying regions of the sample where convergence has not been met;
acquiring third data in the second mode of operation using a multiresolution sampling strategy at the spectral X-ray detector, wherein the third data comprises X-ray transmission spectra corresponding to pixels of the spectral X-ray detector; and
performing multiscale inversions on the X-ray transmission spectra.

26. The method of claim 20, wherein:
the sample is an integrated circuit (IC) sample;
generating the reconstruction of the sample comprises generating a three-dimensional reconstruction of the IC sample; and
converting the three-dimensional reconstruction of the IC sample into a GDSII binary format.

* * * * *